US009744236B2

(12) United States Patent
Yuste et al.

(10) Patent No.: US 9,744,236 B2
(45) Date of Patent: Aug. 29, 2017

(54) PHOTOLABILE COMPOUNDS

(75) Inventors: Rafael Yuste, New York, NY (US); Roberto Etchenique, Buenos Aires (AR); Luis Baraldo, Buenos Aires (AR)

(73) Assignees: The Trustees of Columbia University in the City of New York, New York, NY (US); Universidad de Buenos Aires, Autonoma de Buenos Aires (AR)

( * ) Notice: Subject to any disclaimer, the term of this patent is extended or adjusted under 35 U.S.C. 154(b) by 120 days.

(21) Appl. No.: 13/336,643

(22) Filed: Dec. 23, 2011

(65) Prior Publication Data

US 2012/0220922 A1    Aug. 30, 2012

Related U.S. Application Data

(63) Continuation-in-part of application No. PCT/US2010/040220, filed on Jun. 28, 2010.

(60) Provisional application No. 61/220,922, filed on Jun. 26, 2009.

(51) Int. Cl.
*C07F 15/00* (2006.01)
*A61K 31/555* (2006.01)
*A61K 41/00* (2006.01)
*A61K 31/4045* (2006.01)
*A61K 31/41* (2006.01)
*A61K 31/4409* (2006.01)
*A61K 31/465* (2006.01)
*A61K 31/198* (2006.01)
*A61K 31/675* (2006.01)
*A61K 47/48* (2006.01)
*A61N 5/06* (2006.01)
*B01J 19/12* (2006.01)
*A61N 5/067* (2006.01)

(52) U.S. Cl.
CPC ........ *A61K 41/0042* (2013.01); *A61K 31/198* (2013.01); *A61K 31/4045* (2013.01); *A61K 31/41* (2013.01); *A61K 31/4409* (2013.01); *A61K 31/465* (2013.01); *A61K 31/675* (2013.01); *A61K 47/48076* (2013.01); *A61N 5/062* (2013.01); *B01J 19/12* (2013.01); *C07F 15/0053* (2013.01); *A61N 2005/067* (2013.01); *A61N 2005/0657* (2013.01); *A61N 2005/0659* (2013.01); *A61N 2005/0661* (2013.01); *A61N 2005/0662* (2013.01); *B01J 2219/12* (2013.01)

(58) Field of Classification Search
USPC .............................................. 546/2; 514/188
See application file for complete search history.

(56) References Cited

U.S. PATENT DOCUMENTS 5,350,644 A    9/1994  Graetzel et al.
5,393,903 A    2/1995  Gratzel et al.
5,399,694 A    3/1995  Riess et al.
5,463,057 A    10/1995 Graetzel et al.
5,482,867 A    1/1996  Barrett et al.
5,514,710 A    5/1996  Haugland et al.
5,635,608 A    6/1997  Haugland et al.
5,789,592 A    8/1998  Gratzel et al.
5,872,243 A    2/1999  Gee et al.
5,888,829 A    3/1999  Gee
6,569,544 B1   5/2003  Alain et al.
6,750,357 B1   6/2004  Chiarello et al.
2002/0016472 A1  2/2002  Tsien et al.
2003/0198960 A1  10/2003  Fan et al.
2008/0176940 A1* 7/2008  Etchenique et al. .......... 514/492

FOREIGN PATENT DOCUMENTS

EP        0 414 730        12/1999
WO        WO-03/093236     11/2003
WO        WO 2005/065192 A2 * 7/2005    ............. C07F 15/00
WO        WO-2010/151879   12/2010

OTHER PUBLICATIONS

Zayat, L. et al.: A new inorganic photolabile protecting group for highly efficient visible light GABA uncaging. Chembiochem, vol. 8, pp. 2035-2038, 2007.*

Wright, D. et al.: Thermal control of photoreactivity: room-temperature photosubstitution vs 150 K electron transfer in [(dmb)2Ru(3-Br-py)2](PF6)2. Inorganic Chem., vol. 29, pp. 155-157, 1990.*

Haugland, Richard P., "Handbook of Fluorescent Probes and Research Chemicals", 6th edition, Molecular Probes 1996, table of contents, 6 pages.

Salierno, Marcelo, et al., "A fast ruthenium polypyridine cage complex photoreleases glutamate with visible or IR light in one and two photon regimes", J. Inorg. Biochem., 2010, vol. 104, No. 4, pp. 418-422.

Utzinger, Urs, et al., "Fiber optic probes for biomedical optical spectroscopy", J. Biomed. Optics, Jan. 2003, vol. 8, No. 1, pp. 121-147.

Strickler, James H., et al., "Three-dimensional optical data storage in refractive media two-photon point excitation", Optics Letters, Nov. 15, 1991, vol. 16, No. 22, pp. 1780-1782.

(Continued)

*Primary Examiner* — Charanjit Aulakh
(74) *Attorney, Agent, or Firm* — Wilmer Cutler Pickering Hale and Dore LLP

(57) ABSTRACT

The present invention describes Photolabile Compounds methods for use of the compounds. The Photolabile Compounds have a photoreleasable ligand, which can be biologically active, and which is photoreleased from the compound upon exposure to light. In some embodiments, the Photolabile Compounds comprise a light antenna, such as a labeling molecule or an active derivative thereof. In one embodiment, the light is visible light, which is not detrimental to the viability of biological samples, such as cells and tissues, in which the released organic molecule is bioactive and can have a therapeutic effect. In another embodiment, the photoreleasable ligand can be a labeling molecule, such as a fluorescent molecule.

76 Claims, 29 Drawing Sheets
(7 of 29 Drawing Sheet(s) Filed in Color)

(56) References Cited

OTHER PUBLICATIONS

Denk, Winfried, et al., "Two-Photon Laser Scanning Fluorescence Microscopy", Science, Apr. 6, 1990, vol. 248, pp. 73-76.

Denk, Winfried, "Two-photon scanning photochemical microscopy: Mapping ligand-gated ion channel distributions", Proc. Natl. Acad. Sci. USA, Jul. 1994, vol. 91, pp. 6629-6633.

Wu, George Y., et al., "Receptor-mediated in Vitro Gene Transformation by a Soluble DNA Carrier System", J. Biol. Chem, Apr. 5, 1987, vol. 262, No. 10, pp. 4429-4432.

Langer, Robert, "New Methods of Drug Delivery",Science, Sep. 28, 1990, vol. 249, pp. 1527-1533.

Lopez-Berestein, Gabriel, "Treatment of Systemic Fungal Infections with Liposomal-Amphotericin B", Liposomes in the Therapy of Infectious Disease and Cancer, Alan R. Liss, Inc., NY, 1989, pp. 317-327.

Sefton, Michael, "Implantable Pumps", CRC Crit. Rev. Biomed. Eng., 1987, vol. 14, No. 3, pp. 201-240.

Buchwald, Henry, et al., "Long-term, continuous intravenous heparin administration by an implantable infusion pump in ambulatory patients with recurrent venous thrombosis", Surgery, Oct. 1980, vol. 88, No. 4, pp. 507-516.

Saudek, Christopher D., et al., "A Preliminary Trial of the Programmable Implantable Medication System for Insulin Delivery", The New England Journal of Medicine, Aug. 31, 1989, vol. 321, No. 9, pp. 574-579.

Langer, Robert et al., "Medical Applications of Controlled Release", vol. I, CRC Press Inc., Boca Raton, FL, 1984, table of contents, 4 pages.

Smolen, Victor F., et al., "Controlled Drug Bioavailability: vol. 1 Drug Product Design and Performance", Wiley New York, 1984, table of contents, 3 pages.

Langer, Robert, et al., "Chemical and Physical Structure of Polymers as Carriers for Controlled Release of Bioactive Agents: A Review", J. Macromol. Sci. Rev. Macromol. Chem., 1983, vol. 23, pp. 61-126.

Levy, Robert J., et al., "Inhibition of Calcification of Bioprosthetic Heart Valves by Local Controlled-Release Diphosphonate", Science, Apr. 12, 1985, vol. 228, No. 4696, pp. 190-192.

During, Matthew J., et al., "Controlled Release of Dopamine from a Polymeric Brain Implant: In Vivo Characterization", Annals of Neurology, Apr. 1989, vol. 25, No. 4, pp. 351-356.

Howard, Matthew A., et al., "Intracerebral drug delivery in rats with lesion-induced memory deficits", J. Neurosurg. 1989, vol. 71, pp. 105-112.

Goodson, J. Max, "Dental Applications", 1984, Medical Applications of Controlled Release, Chapter 6, vol. 2, pp. 115-138.

Chun-Ying, Duan, et al., "Crystal Structure and Photochemistry of BIS(Bipyridine)-BIS(4-Aminopyridine)Ruthenium(II)", J. Coord. Chem. 1999, vol. 46, pp. 301-312.

Pinnick, David V., et al., "Photosubstitution Reactions of Ru(bpy)$_2$XY$^{n+}$ Complexes", Inorg. Chem. 1984, vol. 23, pp. 1440-1445.

Dodsworth, Elaine S., et al., "Correlations Between Electrochemical Potentials and Optical Charge Transfer Energies in Ruthenium Bipyridine Derivatives", Chem. Phys. Lett., Feb. 14, 1986, vol. 124, No. 2, pp. 152-158.

Schlue, W. R., et al., "Extracellular Potassium in Neuropile and Nerve Cell Body Region of the Leech Central Nervous System", J. Exp. Biol., 1980, vol. 87, pp. 23-43.

Viala, Christine, et al., "An expeditious route to cis-Ru(bpy)2Cl2 (bpy=2,2'-bypyridine) using carbohydrates as reduces", Inorg. Chim. Acta, 2006, vol. 359, pp. 984-989.

Adamczyk, Maciej, et al., "Efficient Synthesis of Rhodamine Conjugates Through the 2'-Position", J. Bioorg. Med. Chem. Lett., 2000, vol. 10, pp. 1539-1541.

European Search Report issued for corresponding EP application No. 10792793.1, mailed Dec. 5, 2012, 10 pages.

Zayat, Leonardo, et al., "A New Strategy for Neurochemical Photodelivery: Metal-Ligand Heterolytic Cleavage", Journal of the American Chemical Society, Jan. 1, 2003, vol. 125, No. 4, pp. 882-883.

Zayat, Leonardo, et al., "Ruthenium(II) Bipyridyl Complexes as Photolabile Caging Groups for Amines", Inorganic Chemistry, Feb. 1, 2006, vol. 45, No. 4, pp. 1728-1731.

Salierno, Marcelo, et al., "Caged Amino Acids for Visible-Light Photodelivery", European Journal of Inorganic Chemistry, Mar. 1, 2008, vol. 2008, No. 7, pp. 1125-1128.

Lebon, Emilie, et al., "X-ray structure, redox and spectroscopic properties of ruthenium phosphine complexes [Ru(tpy)(bpy)(PPh$_3$)]$^{2+}$ and [Ru(tpy)(bpy)(PCy$_3$)]$^{2+}$", Inorganica Chimica Acta, Jan. 21, 2007, vol. 360, No. 3, pp. 1235-1239.

Katz, Néstor, E., et al., "4-Cyanopyridine-Bridged Binuclear and Trinuclear Complexes of Ruthenium and Iron", Inorg. Chem., May 1, 1988, vol. 27, No. 10, pp. 1687-1694.

Bessel, Carol A., et al., "Steric Ligand Effects of Six Bidentate Bipyridyl Ligands", Inorg. Chem., Dec. 1, 1993, vol. 32, No. 25, pp. 5779-5784.

Marmion, Mary E., et al., "Ruthenium(IV)-Oxo Complexes: The Novel Utilization of Tertiary Pnictogen Ligands", J. Am. Chem. Soc., Mar. 1, 1988, vol. 110, No. 5, pp. 1472-1480.

Treat, Joseph, et al., "Liposome Encapsulated Doxorubicin Preliminary Results of Phase I and Phase II Trials", Liposomes in the Therapy of Infectious Disease and Cancer, Alan R. Liss, Inc., NY, 1989, pp. 353-365.

Fino, Elodie, et al., "RuBi-Glutamate: two-photon and visible-light photoactivation of neurons and dendritic spines", Frontiers in Neural Circuits, May 2009, vol. 3, Article 2, pp. 1-9.

International Search Report for corresponding International Application No. PCT/US10/40220, dated Jan. 18, 2011, 1 page.

PubChem Iodeosin, http://pubchem.ncbi.nlm.nih.gov/summary/summary.cgi?sid=458734&loc=es_rss#synonyms, Release date Oct. 2011, printed on Feb. 6, 2013, 2 pages.

Griffith, William. P., et al., "Ruthenate-catalysed dehydrogenation of primary amines to nitriles, and crystal structure of cis-[Ru(bipy)2(NH2CH2Ph)2-[PF6]2•0.5MeOH and cis-[Ru(bipy)2(NCPh)2][PF6]2CH2CL2", J. Chem. Soc., Dalton Trans., 1998, pp. 2819-2825.

Mines, G. A., et al., "Rates of heme oxidation and reduction in Ru(His33)cytochrome c at very high driving forces", J. Am. Chem. Soc., 1996, vol. 118, pp. 1961-1965.

Bosnich, B., et al., "Bis-1,10-Phenanthroline Complexes of Divalent Ruthenium", Aust. J. Chem., 1966, vol. 19, pp. 2229-2233.

Zoepf, T., "Photodynamic therapy of cholangiocarcinoma", HPB, Feb. 2008, vol. 10, pp. 161-163.

International Search Report and Written Opinion issued for PCT/US12/71370, dated Mar. 5, 2013, 11 pages.

Office Action from the Japanese Patent Office for Japanese Patent Application No. 2012-517826, 3 pages, mailed on Jul. 3, 2014.

Davia, K., et al., "A porphyrin-ruthenium photosensitizer as a potential photodynamic therapy agent," Inorganic Chemistry Communications, vol. 11, 4 pages (2008).

Sowinska, M., et al., "Photoluminescence of Ruthenium Complexes With Molecules Exhibiting Twisted Internal Charge Transfer States," Journal of Photochemistry, vol. 37, 12 pages (1987).

Fujimoto, James G., et al., "Photonic Materials, Devices and Systems", Laser Medicine and Medical Imaging Group, RLE Progress Report 144, pp. 27-1 to 27-35 (2001).

Litke, S. V., et al., "Photophysics of Mixed Ligand Complexes of Ruthenium(II) with 2,2'-bipyridyl and Phosphines," Optics and Spectroscopy, vol. 89, No. 6, pp. 847-853 (2000).

Garcia et al., "Sensitization of n-Type TiO$_2$ Electrode by a Novel Isoquinoline Ruthenium(II) Polypyridyl Complex," J. Braz. Chem. Soc. vol. 9, pp. 13-15 (1998).

Mines et al., "Electron Tunneling in Engineered Proteins," Adv. in Chem. Series, vol. 254, pp. 51-63 (1998).

Nagamura et al., "Photoinduced electron transfer between amphipathic Ruthenium (II) complex and N,N-dimethylaniline in synthetic bilayer membranes and phospholipid liposomes," Chem. Letters, vol. 5, pp. 503-506 (1980).

* cited by examiner (RS)-(Tetrazol-5-yl)glycine

A

B

PHOTOLABILE COMPOUNDS

CROSS-REFERENCE TO RELATED APPLICATIONS

This application is a continuation-in-part of International Patent Application No. PCT/US2010/40220, filed Jun. 28, 2010, which claims priority to U.S. Provisional Patent Application Ser. No. 61/220,922, filed Jun. 26, 2009, the entire disclosure of each is incorporated by reference herein. U.S. Pat. Pub. No. 2008-0176940 is also incorporated herein by reference in its entirety.

The work herein was supported in whole, or in part, by National Institute of Health Grant Nos. EY011787 and EY013237. Thus, the United States Government has certain rights to the invention. This invention was made with government support under NYSTAR Contract No. C000082 awarded by NYSTAR. The government has certain rights in the invention.

This patent disclosure contains material which is subject to copyright protection. The copyright owner has no objection to the facsimile reproduction by anyone of the patent document or the patent disclosure, as it appears in the U.S. Patent and Trademark Office patent file or records, but otherwise reserves any and all copyright rights.

FIELD OF THE INVENTION

The present invention relates generally to novel Photolabile Compounds and methods for uncaging an organic molecule, such as a bioactive molecule, which can have a variety of uses both in vitro and in vivo.

BACKGROUND OF THE INVENTION

Photolabile protecting groups, which are also called caging groups, are classes of protecting groups that are particularly useful in the biological sciences. Because light can be controlled with precision both spatially and temporally, cleaving a protecting group from a bioactive molecule allows release, or uncaging, of the molecule. Protecting groups typically mask or conceal charged (for example, carboxylate or phosphate) or polar (for example, amine, hydroxyl, or sulfhydryl) groups on the compounds. Frequently such functionalities increase the hydrophobicity and membrane permeability of the protected molecules. Prior to photolysis, the Photolabile Compounds are typically chemically or biologically inactive because at least one of the compounds' main functionalities is blocked. The activity of the molecule can be triggered by a pulse of light, thereby releasing the molecule from the photoreleasable compound. Thus, photolabile protecting groups can be removed from a protected compound by irradiation, for example, to control the release of the compound when and where desired, either in vivo or in vitro.

Commercially available Photolabile Compounds typically require ultraviolet (UV) light to remove the compounds from the cage. However, UV light can cause damage to organs, tissues and cells, thus making UV light detrimental for in vivo use. Thus, there is a need in the art to utilize new Photolabile Compounds having ligands that can be released using light other than UV light, particularly for in vivo applications. The present invention provides novel Photolabile Compounds and methods for using the compounds, which provide advantages over currently available compounds that are photolabile using only UV light.

SUMMARY OF THE INVENTION

It is an aspect of the present invention to provide novel Photolabile Compounds that protect an organic molecule, such as a bioactive molecule. Upon exposure to light, the organic molecule is released, and is useful in the methods described herein.

In one aspect, the present invention provides compounds of Formula I:

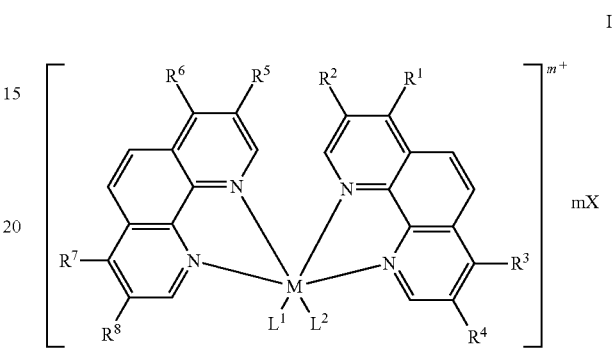

wherein M is Ru;
each $L^1$ is independently an organic molecule having:
(a) a 5-membered monocyclic aromatic ring, one of the ring's members being a nitrogen atom that forms a bond with M;
(b) a 6-membered monocyclic aromatic ring, one of the ring's members being a nitrogen atom that forms a bond with M;
(c) an 8-10-membered bicyclic ring, one of the bicyclic rings being aromatic and having a nitrogen atom member that forms a bond with M;
(d) an —$NH_2$ group whose nitrogen atom forms a bond with M;
(e) a —COOH group, one of whose oxygen atoms forms a bond with M; or
(f) a —CN group whose nitrogen atom forms a bond with M;
$L^2$ is $(R^9)_3P$, $(R^9O)_3P$, or $L^1$ and m is 2; or $L^2$ is —CN and m is 1; or $L^2$ is a labeling molecule or an active derivative thereof connected to M through the phosphorous atom of $(R^9)_2P$ or $(R^9O)_2P$ and m is 2; or $L^2$ is a labeling molecule or an active derivative thereof connected to M through the nitrogen atom of: $NHR^9$, $N(R^9)_2$, pyridyl, $C(R^9)$=NH, $C(R^9)$=$NR^9$ cyclic aliphatic amine group or nitrile and m is 2;
wherein each $R^9$ is independently —$C_1$-$C_{18}$ alkyl, —$C_3$-$C_8$ cycloalkyl, or phenyl;
$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and
X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In one embodiment of the compounds of Formula I, M is Ru;
each $L^1$ is independently an organic molecule having:
(a) a 5-membered monocyclic aromatic ring, one of the ring's members being a nitrogen atom that forms a bond with M;
(b) a 6-membered monocyclic aromatic ring, one of the ring's members being a nitrogen atom that forms a bond with M;

(c) an 8-10-membered bicyclic ring, one of the bicyclic rings being aromatic and having a nitrogen atom member that forms a bond with M;

(d) an —NH$_2$ group whose nitrogen atom forms a bond with M; or (e) a —COOH group, one of whose oxygen atoms forms a bond with M;

$L^2$ is $(R^9)_3P$, $(R^9O)_3P$, or $L^1$ and m is 2; or $L^2$ is —CN and m is 1; or $L^2$ is a labeling molecule or an active derivative thereof connected to M through the phosphorous atom of $(R^9)_2P$ or $(R^9O)_2P$ and m is 2; or $L^2$ is a labeling molecule or an active derivative thereof connected to M through the nitrogen atom of: NHR$^9$, N(R$^9$)$_2$, pyridyl, C(R$^9$)=NH, C(R$^9$)=NR$^9$ cyclic aliphatic amine group or nitrile and m is 2;

wherein each R$^9$ is independently —C$_1$-C$_{18}$ alkyl, —C$_3$-C$_8$ cycloalkyl, or phenyl;

R$^1$-R$^8$ are independently —H, —C$_1$-C$_{18}$ alkyl, —NH$_2$, —COOH, —(C$_1$-C$_{18}$ alkyl)-O—(C$_1$-C$_{18}$ alkyl), or —OC(O)(C$_1$-C$_{18}$ alkyl); and X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$.

In one embodiment of the compounds of Formula I, M is Ru;

each L$^1$ is independently an organic molecule having:

(a) a 5-membered monocyclic aromatic ring, one of the ring's members being a nitrogen atom that forms a bond with M;

(b) a 6-membered monocyclic aromatic ring, one of the ring's members being a nitrogen atom that forms a bond with M;

(c) an 8-10-membered bicyclic ring, one of the bicyclic rings being aromatic and having a nitrogen atom member that forms a bond with M;

(d) an —NH$_2$ group whose nitrogen atom forms a bond with M; or (e) a —COOH group, one of whose oxygen atoms forms a bond with M; or (f) a —CN group whose nitrogen atom forms a bond with M;

$L^2$ is $(R^9)_3P$, $(R^9O)_3P$, or $L^1$ and m is 2; or $L^2$ is —CN and m is 1;

R$^1$-R$^8$ are independently —H, —C$_1$-C$_{18}$ alkyl, —NH$_2$, —COOH, —(C$_1$-C$_{18}$ alkyl)-O—(C$_1$-C$_{18}$ alkyl), or —OC(O)(C$_1$-C$_{18}$ alkyl); and X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$.

In one embodiment of the compounds of Formula I, M is Ru;

each L$^1$ is independently an organic molecule having:

(a) a 5-membered monocyclic aromatic ring, one of the ring's members being a nitrogen atom that forms a bond with M;

(b) a 6-membered monocyclic aromatic ring, one of the ring's members being a nitrogen atom that forms a bond with M;

(c) an 8-10-membered bicyclic ring, one of the bicyclic rings being aromatic and having a nitrogen atom member that forms a bond with M;

(d) an —NH$_2$ group whose nitrogen atom forms a bond with M; or (e) a —COOH group, one of whose oxygen atoms forms a bond with M;

$L^2$ is $(R^9)_3P$, $(R^9O)_3P$, or $L^1$ and m is 2; or $L^2$ is —CN and m is 1;

R$^1$-R$^8$ are independently —H, —C$_1$-C$_{18}$ alkyl, —NH$_2$, —COOH, —(C$_1$-C$_{18}$ alkyl)-O—(C$_1$-C$_{18}$ alkyl), or —OC(O)(C$_1$-C$_{18}$ alkyl); and X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$.

In some embodiments of the compounds of Formula I, when L$^2$ is (R$^9$)$_3$P, each R$^9$ is different from each other.

In some embodiments of the compounds of Formula I, when L$^2$ is (R$^9$)$_3$P, two R$^9$ are the same and different from the remaining R$^9$.

In some embodiments of the compounds of Formula I, when L$^2$ is (Ph)$_3$P, each phenyl is not substituted with methyl.

In another aspect, the present invention provides compounds of Formula II:

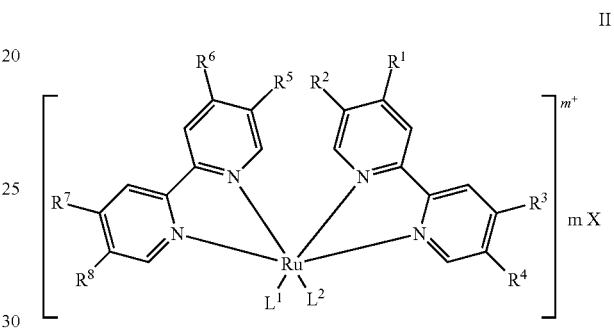

wherein:

each L$^1$ is independently an organic molecule having:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —NH$_2$ group whose nitrogen atom forms a bond with Ru;

(e) a —COOH group, one of whose oxygen atoms' forms a bond with Ru; or (f) a —CN group whose nitrogen atom forms a bond with Ru;

$L^2$ is $(R^9)_3P$, $(R^9O)_3P$, or L and m is 2; or $L^2$ is —CN and m is 1; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: NHR$^9$, N(R$^9$)$_2$, pyridyl, C(R$^9$)=NH, C(R$^9$)=NR$^9$ cyclic aliphatic amine group or nitrile and m is 2;

wherein each R$^9$ is independently —C$_1$-C$_{18}$ alkyl, —C$_3$-C$_8$ cycloalkyl, or phenyl;

R$^1$-R$^8$ are independently —H, —C$_1$-C$_{18}$ alkyl, —NH$_2$, —COOH, —(C$_1$-C$_{18}$ alkyl), or —OC(O)(C$_1$-C$_{18}$ alkyl); and X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$.

In one embodiment of the compounds of Formula II, each L$^1$ is independently an organic molecule having:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru; or (e) a —COOH group, one of whose oxygen atoms forms a bond with Ru;

$L^2$ is $(R^9)_3P$, $(R^9O)_3P$, or L and m is 2; or $L^2$ is —CN and m is 1; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)=NH$, $C(R^9)=NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In one embodiment of the compounds of Formula II, each $L^1$ is independently an organic molecule having:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru; or (e) a —COOH group, one of whose oxygen atoms forms a bond with Ru; or (f) a —CN group whose nitrogen atom forms a bond with Ru;

$L^2$ is $(R^9)_3P$, $(R^9O)_3P$, or $L^1$ and m is 2; or $L^2$ is —CN and m is 1;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In one embodiment of the compounds of Formula II, each $L^1$ is independently an organic molecule having:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru; or (e) a —COOH group, one of whose oxygen atoms forms a bond with Ru;

$L^2$ is $(R^9)_3P$, $(R^9O)_3P$, or $L^1$ and m is 2; or $L^2$ is —CN and m is 1;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$ or ($C_1$-$C_{18}$ alkyl)-$SO_3^-$.

In some embodiments of the compounds of Formula II, when $L^2$ is $(R^9)_3P$, each $R^9$ is different from each other.

In some embodiments of the compounds of Formula II, when $L^2$ is $(R^9)_3P$, two $R^9$ are the same and different from the remaining $R^9$.

In some embodiments of the compounds of Formula II, when $L^2$ is $(Ph)_3P$, each phenyl is not substituted with methyl.

In another aspect, the present invention provides compounds of Formula III:

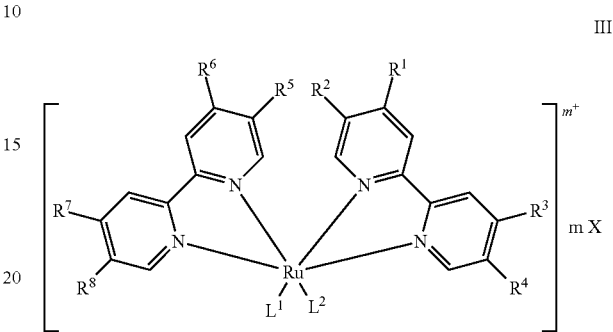

III wherein:

$L^1$ is 4-aminopyridine (4-AP), whose pyridyl nitrogen atom forms a bond with Ru;

$L^2$ is $(R^9)_3P$, $(R^9O)_3P$, or $L^1$ and m is 2; or $L^2$ is —CN and m is 1; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)=NH$, $C(R^9)=NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is a $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In one embodiment of the compounds of Formula III, $L^1$ is 4-aminopyridine (4-AP), whose pyridyl nitrogen atom forms a bond with Ru;

$L^2$ is $(R^9)_3P$, $(R^9O)_3P$, or $L^1$ and m is 2; or $L^2$ is —CN and m is 1;

$R^1$-$R^8$ are independently —H, —$C_1$-$C_{18}$ alkyl, —$NH_2$, —COOH, —($C_1$-$C_{18}$ alkyl)-O—($C_1$-$C_{18}$ alkyl), or —OC(O)($C_1$-$C_{18}$ alkyl); and X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$.

In some embodiments of the compounds of Formula III, when $L^2$ is $(R^9)_3P$, each $R^9$ is different from each other.

In some embodiments of the compounds of Formula III, when $L^2$ is $(R^9)_3P$, two $R^9$ are the same and different from the remaining $R^9$.

In some embodiments of the compounds of Formula III, when $L^2$ is $(Ph)_3P$, each phenyl is not substituted with methyl.

In another aspect, the present invention provides compounds of Formula IV:

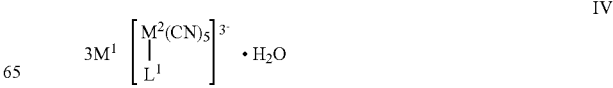

IV wherein:

$M^1$ is $Li^+$, $Na^+$, or $K^+$;

$M^2$ is Ru;

and $L^1$ is independently an organic molecule having:

(a) a 5-membered monocyclic aromatic ring, one of the ring's members being a nitrogen atom that forms a bond with $M^2$;

(b) a 6-membered monocyclic aromatic ring, one of the ring's members being a nitrogen atom that forms a bond with $M^2$;

(c) an 8-10-membered bicyclic ring, one of the bicyclic rings being aromatic and having a nitrogen atom member that forms a bond with $M^2$;

(d) an —$NH_2$ group whose nitrogen atom forms a bond with $M^2$;

(e) a —COOH group, one of whose oxygen atoms forms a bond with $M^2$; or (f) a —CN group whose nitrogen atom forms a bond with $M^2$.

In one embodiment of the compounds of Formula IV, $M^1$ is $Li^+$, $Na^+$, or $K^+$;

$M^2$ is Ru;

and $L^1$ is independently an organic molecule having:

(a) a 5-membered monocyclic aromatic ring, one of the ring's members being a nitrogen atom that forms a bond with $M^2$;

(b) a 6-membered monocyclic aromatic ring, one of the ring's members being a nitrogen atom that forms a bond with $M^2$;

(c) an 8-10-membered bicyclic ring, one of the bicyclic rings being aromatic and having a nitrogen atom member that forms a bond with $M^2$;

(d) an —$NH_2$ group whose nitrogen atom forms a bond with $M^2$; or (e) a —COOH group, one of whose oxygen atoms forms a bond with $M^2$.

In another aspect, the present invention provides compounds of Formula V:

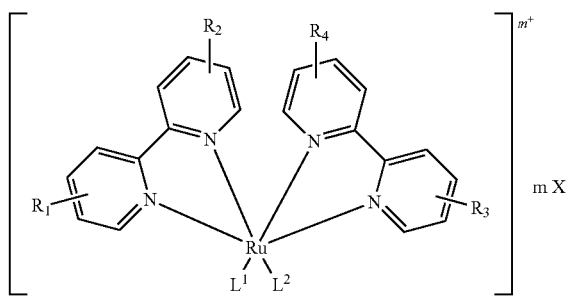

V wherein:

each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru;

$L^2$ is $(R^9)_3P$, $(R^9O)_3P$, or $L^1$ and m is 2; or $L^2$ is —CN and m is 1; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

wherein when $L^2$ is $P(phenyl)_3$ or a labeling molecule or an active derivative thereof connected to Ru through the phosphorous atom of $P(phenyl)_2$, each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH, and $R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

wherein when $L^2$ is not $P(phenyl)_3$, $R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula V:

each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

$L^2$ is $(R^9)_3P$, $(R^9O)_3P$, or $L^1$ and m is 2; or $L^2$ is —CN and m is 1; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

wherein when $L^2$ is $P(phenyl)_3$ or a labeling molecule or an active derivative thereof connected to Ru through the phosphorous atom of $P(phenyl)_2$, each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH, and $R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

wherein when $L^2$ is not $P(phenyl)_3$, $R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula V, each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru;

wherein when $L^2$ is $P(phenyl)_3$, each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH, and $R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

wherein when $L^2$ is not $P(phenyl)_3$, $R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula V, each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

wherein when $L^2$ is $P(phenyl)_3$, each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH, and $R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

wherein when $L^2$ is not $P(phenyl)_3$, $R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In some embodiments of the compounds of Formula V, when $L^2$ is $(R^9)_3P$, each $R^9$ is different from each other.

In some embodiments of the compounds of Formula V, when $L^2$ is $(R^9)_3P$, two $R^9$ are the same and different from the remaining $R^9$.

In some embodiments of the compounds of Formula V, when $L^2$ is $(Ph)_3P$, each phenyl is not substituted with methyl.

In another aspect, the present invention provides compounds of Formula VI:

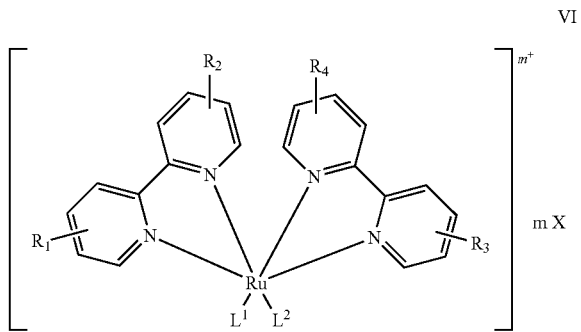

VI wherein:

each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru;

$L^2$ is P(phenyl)$_3$, wherein each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula VI:

each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

$L^2$ is P(phenyl)$_3$, wherein each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula VI, each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru;

$L^2$ is P(phenyl)$_3$, wherein each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2$Y, —C(=O)Y, —C(=O)$NY_2$, —$NH_2$, —$NO_2$, —OH, or —SH;

$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2$Y, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

X is Cl$^-$, F$^-$, Br$^-$, I$^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula VI, each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

$L^2$ is P(phenyl)$_3$, wherein each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2$Y, —C(=O)Y, —C(=O)$NY_2$, —$NH_2$, —$NO_2$, —OH, or —SH;

$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl-amino, —($C_1$-$C_{18}$ alkyl)-thio, —$CO_2$Y, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

X is Cl$^-$, F$^-$, Br$^-$, I$^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In some embodiments of the compounds of Formula VI, when $L^2$ is ($R^9$)$_3$P, each $R^9$ is different from each other.

In some embodiments of the compounds of Formula VI, when $L^2$ is ($R^9$)$_3$P, two $R^9$ are the same and different from the remaining $R^9$.

In some embodiments of the compounds of Formula VI, when $L^2$ is (Ph)$_3$P, each phenyl is not substituted with methyl.

In another aspect, the present invention provides compounds of Formula VII:

$$\left[ \begin{array}{c} \text{[Ru complex structure with two bipyridyl ligands bearing } R_1, R_2, R_3, R_4 \text{ substituents, and } L^1, L^2 \text{ ligands]} \end{array} \right]^{m+} \quad mX$$

VII wherein:

each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru;

$L^2$ is ($R^9$)$_3$P, ($R^9$O)$_3$P, or $L^1$, wherein each $R^5$ is independently —$C_1$-$C_{18}$ alkyl, —$C_3$-$C_8$ cycloalkyl, or phenyl, m is 2, and $L^2$ is not P(phenyl)$_3$; or $L^2$ is —CN and m is 1; or $L^2$ is a labeling molecule or an active derivative thereof connected to Ru through the phosphorous atom of ($R^9$)$_2$P or ($R^9$O)$_2$P and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2$Y, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is Cl$^-$, F$^-$, Br$^-$, I$^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula VII:

each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f), a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

$L^2$ is $(R^9)_3P$, $(R^9O)_3P$, or $L^1$, wherein each $R^5$ is independently —$C_1$-$C_{18}$ alkyl, —$C_3$-$C_8$ cycloalkyl, or phenyl, m is 2, and $L^2$ is not $P(phenyl)_3$; or $L^2$ is —CN and m is 1; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula VII, each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

(h) a —CN group whose nitrogen atom forms a bond with Ru;

$L^2$ is $(R^9)_3P$, $(R^9O)_3P$, or $L^1$, wherein each $R^5$ is independently —$C_1$-$C_{18}$ alkyl, —$C_3$-$C_8$ cycloalkyl, or phenyl, m is 2, and $L^2$ is not $P(phenyl)_3$; or $L^2$ is —CN and m is 1;

$R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of Formula VII, each $L^1$ is independently an organic molecule having:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl;

$L^2$ is $(R^9)_3P$, $(R^9O)_3P$, or $L^1$, wherein each $R^5$ is independently —$C_1$-$C_{18}$ alkyl, —$C_3$-$C_8$ cycloalkyl, or phenyl, m is 2, and $L^2$ is not $P(phenyl)_3$; or $L^2$ is —CN and m is 1;

$R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In some embodiments of the compounds of Formula VII, when $L^2$ is $(R^9)_3P$, each $R^9$ is different from each other.

In some embodiments of the compounds of Formula VII, when $L^2$ is $(R^9)_3P$, two $R^9$ are the same and different from the remaining $R^9$.

In some embodiments of the compounds of Formula VII, when $L^2$ is $(Ph)_3P$, each phenyl is not substituted with methyl.

In another aspect, the present invention provides compounds of Formula VIII:

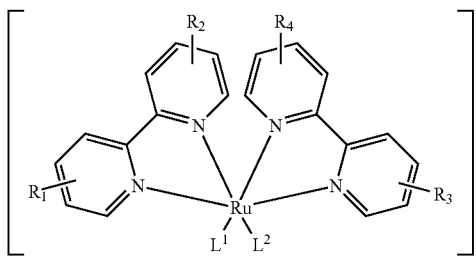

wherein:

each $L^1$ is independently a labeling molecule or an active derivative thereof connected to Ru through the phosphorous atom of $(R^9)_2P$ or $(R^9O)_2P$ and m is 2; or $L^1$ is a labeling molecule or an active derivative thereof connected to Ru through the nitrogen atom of: $NHR^9$, $N(R^9)_2$, pyridyl, $C(R^9)=NH$, $C(R^9)=NR^9$ cyclic aliphatic amine group or nitrile and m is 2;

wherein each $R^9$ is independently —$C_1$-$C_{18}$ alkyl, —$C_3$-$C_8$ cycloalkyl, or phenyl;

$L^2$ is Cl—, phosphine, $OH_2$, or pyridine and m is 2; or $L^2$ is —CN and m is 1;

$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In one embodiment of the compounds of formula VIII, each $L^1$ is independently a labeling molecule;
$L^2$ is Cl—, phosphine, $OH_2$, or pyridine and m is 2; or $L^2$ is —CN and m is 1;

$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;

X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

In some embodiments of the compounds of Formula I-III, $R^1$-$R^8$ are each hydrogen.

In some embodiments of the compounds of Formula V-VIII, $R^1$-$R^4$ are each hydrogen.

In some embodiments of the compounds of Formula VII-VIII, $L^1$ is methyl beta-D-1-thiogalactopyranoside. In some embodiments of the compounds of Formula VII-VIII, $L^1$ is methyl beta-D-1-thiogalactopyranoside and $L^2$ is $(R^9)_3P$. In some embodiments of the compounds of Formula VII-VIII, $L^1$ is methyl beta-D-1-thiogalactopyranoside, $L^2$ is $(Ph)_3P$.

In some embodiments of the compounds of Formula VII-VIII, $L^1$ is isopropyl beta-D-1-thiogalactopyranoside. In some embodiments of the compounds of Formula VII-VIII, $L^1$ is isopropyl beta-D-1-thiogalactopyranoside and $L^2$ is $(R^9)_3P$. In some embodiments of the compounds of Formula VII-VIII, $L^1$ is isopropyl beta-D-1-thiogalactopyranoside, $L^2$ is $(Ph)_3P$.

In some embodiments of the compounds of Formula VIII, when $L^2$ is $(R^9)_3P$, each $R^9$ is different from each other.

In some embodiments of the compounds of Formula VIII, when $L^2$ is $(R^9)_3P$, two $R^9$ are the same and different from the remaining $R^9$.

In some embodiments of the compounds of Formula VIII, when $L^2$ is $(Ph)_3P$, each phenyl is not substituted with methyl.

In some embodiments of the compounds of Formula I-III and V-VIII, $L^2$ is $(R^9)_3P$. In some embodiments of the compounds of Formula I-III and V-VIII, $L^2$ is $(R^9)_3P$, wherein each $R^9$ is independently —($C_1$-$C_{18}$)-alkyl. In some embodiments of the compounds of Formula I-III and V-VIII, $L^2$ is $(R^9)_3P$, wherein each $R^9$ is independently —($C_1$-$C_6$)-alkyl. In some embodiments of the compounds of Formula I-III and V-VIII, $L^2$ is $(R^9)_3P$, wherein each $R^9$ is independently —($C_1$-$C_3$)-alkyl. In some embodiments of the compounds of Formula I-III and V-VIII, $L^2$ is $(Me)_3P$.

In some embodiments of the compounds of Formula I-III and V-VIII, $L^2$ is Rhodamine B-Methylaminopropionitrile-amide (RhodB-MAPN). In some embodiments of the compounds of Formula I-III and V-VIII, $L^2$ is Rhodamine G-Methylaminopropionitrileamide (RhodG-MAPN).

In some embodiments of the compounds of Formula I-III and V-VIII, $L^2$ is:

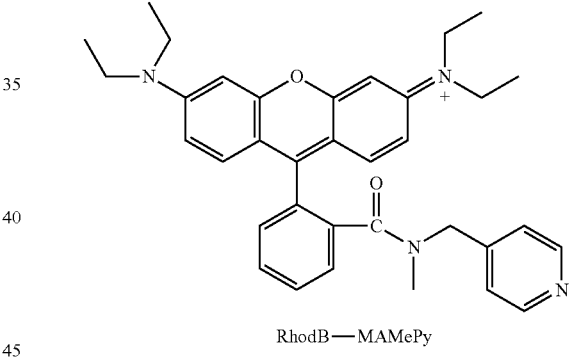

RhodB—MAMePy (RhodB-MAMePy) or a chloride salt thereof (RhodB-MAMePy-Cl).

In some embodiments of the compounds of Formula I-III and V-VIII, $L^2$ is:

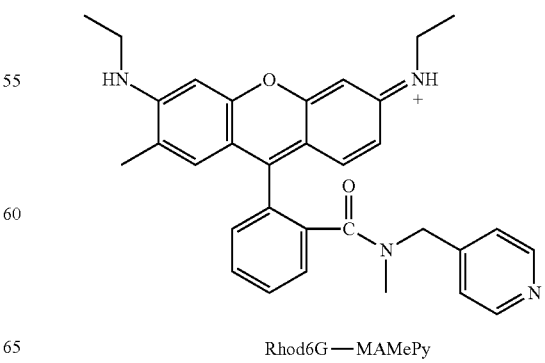

Rhod6G—MAMePy (Rhod6G-MAMePy) or a chloride salt thereof (Rhod6G-MAMePy-Cl).

In some embodiments of the compounds of Formula I-III and V-VIII, the labeling molecule is rhodamine B. In some embodiments of the compounds of Formula I-III and V-VIII, the labeling molecule is rhodamine 6G.

In some embodiments of the compounds of Formula I-III and V-VIII, the labeling molecule is selected from the group consisting of bodipy, dansyl, fluorescein, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, and arginine. A compound of Formula I-VIII ("a Photolabile Compound") releases $L^1$ upon exposure to light.

In another aspect, the present invention provides a composition comprising an effective amount of a Photolabile Compound and a physiologically acceptable carrier, vehicle, diluent, or excipient.

In another aspect, the present invention provides a vessel containing a Photolabile Compound.

In yet another of its aspects, the present invention provides a kit comprising a Photolabile Compound and instructions for use.

Another aspect of the present invention provides methods for releasing an organic molecule or a labeling molecule from a Photolabile Compound, comprising exposing a Photolabile Compound to light under conditions sufficient to release the organic molecule or labeling molecule.

In yet another aspect, the present invention provides a method for making an organic molecule bioavailable to a subject in need of the organic molecule, comprising administering a Photolabile Compound to the subject; and exposing the compound to light under conditions sufficient to release the organic molecule from the compound.

In another aspect, the present invention provides methods for treating diseases and disorders in a subject, comprising: (a) administering a Photolabile Compound to the subject; and (b) exposing the Photolabile Compound to light under conditions sufficient to release the organic molecule from the Photolabile Compound. In some embodiments, the diseases and disorders treated by the methods of the invention include neurological, neurophysiological, or neuromuscular diseases and conditions, such as epilepsy and multiple sclerosis; cancers; diaphoresis; and blood dyscrasias.

In another aspect, the present invention provides methods for assaying an organic molecule, comprising: (a) exposing a Photolabile Compound and a biological sample to light under conditions sufficient to release the organic molecule from the Photolabile Compound, and (b) determining an effect of the organic molecule on the biological sample.

In one aspect, the invention provides a compound selected from the group consisting of: [Ru(bpy)2(RhodB-MAPN)Cl]Cl, [Ru(bpy)2(Rhod6G-MAPN)Cl]Cl, [Ru(bpy)2(RhodB-MAMePy)Cl]Cl.

In another aspect, the invention provides a compound selected from the group consisting of: [Ru(bpy)2(RhodB-MAPN)Cl]Z, [Ru(bpy)2(Rhod6G-MAPN)Cl]Z, [Ru(bpy)2(RhodB-MAMePy)Cl]Z, wherein Z is an anion. In some embodiments, Z Cl⁻, F⁻, Br⁻ or I⁻.

Additional aspects, features and advantages afforded by the present invention will be apparent from the detailed description, figures, and exemplification hereinbelow.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 7A shows a recording of Retzius neuron voltage activity during perfusion of free 4AP on the leech ganglia. [4AP]=0, 10, 20 and 50 mM. Flow rate=1 ml/min. Carrier: saline solution, as described in Example 3. FIG. 7B shows the recording of Retzius neuron activity during exposure to a 0.1 msec flash of green light through the filter of FIG. 6. Flow rate=1 ml/min. Carrier: saline solution, as described in Example 3. Pulse energy: 0.5 J.

FIG. 8A: spectrum changes of [Ru(bpy)$_2$(4AP)$_2$]Cl$_2$ during irradiation with 473 nm laser light. Power: 6.39 mW continuous. Initial concentration of [Ru(bpy)$_2$(4AP)$_2$]Cl$_2$: 27.9 µM. A(473 nm)=0.18. FIG. 8B: Fraction of [Ru(bpy)$_2$(4AP)(H$_2$O)]$^{2+}$ as a function of irradiation time obtained from the spectra depicted in FIG. 8A.

FIG. 13A depicts the structure of TzGly. FIG. 13B demonstrates the spiking of a mouse cortical neuron caused by the addition of TzGly (1 µM) to neuron via perfusion. The measurement results were obtained by the whole-cell patch-clamp method, as known and used in the art.

FIGS. 14A, B and C show fluorescent-image micrographs of a neuron, including magnified views of dendritic spines. FIG. 14D shows the effect of laser irradiation (~40 mW) on the spiking of a single neuron in the presence of $[Ru(bpy)_2(TzGly)_2]Cl_2$. Concentration of $[Ru(bpy)_2(TzGly)_2]Cl_2=100$ μM; Pulse length: 10 ms; Power: 40 mW; Wavelength: 720 nm. FIGS. 14E-G relate to experiments carried out as controls to the experiments of FIGS. 14A-D. FIGS. 14E and F show magnified views of the dendritic spines of a neuron. FIG. 14G presents a plot showing the effect of laser irradiation on a control neuron in the absence of $[Ru(bpy)_2(TzGly)_2]Cl_2$. No increased activity is observed. Pulse length: 10 ms; Power: 40 mW; Wavelength: 720 nm.

FIG. 24A shows a handheld projector 3M (110 MPro) used to irradiate for 20 minutes an *E. coli* culture growing in a piece of 7 cm diameter whatman filter paper soaked in LB medium containing 1 mM $[(Ru(bpy)_2P (Me)_3(MTG)]^{+2}$ and 0.02% X-Gal.

DETAILED DESCRIPTION OF THE INVENTION

Figure 1:
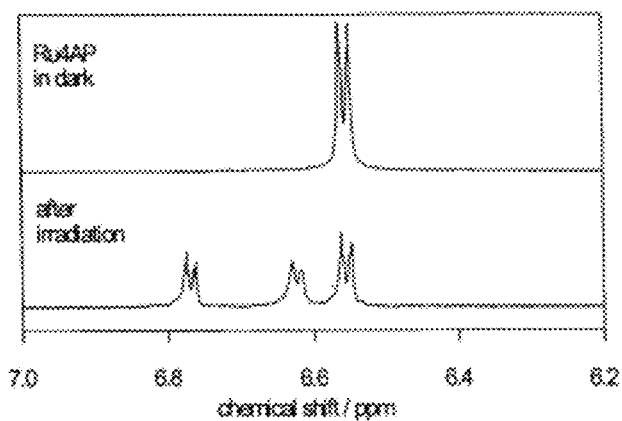
FIG. 1 depicts a partial $^1$H NMR spectra of [Ru(bpy)$_2$(4AP)$_2$]Cl$_2$, as described herein (Example 1), showing the signals corresponding to the 4-AP meta hydrogens. m1: in [Ru(bpy)$_2$(4AP)$_2$]$^{2+}$; m2: in [Ru(bpy)$_2$(H$_2$O)(4AP)$_2$]$^{2+}$; m3: in free ligand 4-AP.

The present invention relates generally to Photolabile Compounds comprising organic molecules or labeling molecules and methods for using the Photolabile Compounds. The organic molecules can be biologically active. In one embodiment of this invention, an organic molecule, e.g., a biologically active molecule, is protected and subsequently released upon exposure to light, advantageously, visible light.

In contrast to known methods, visible light, e.g., a visible light pulse, can be used to release an organic molecule or a labeling molecule from a Photolabile Compound. Thus, in the present methods, samples, e.g., organs, tissues or cells, or subjects to which a Photolabile Compound is administered, undergo only minimal, if any, exposure to UV radiation, which has detrimental effects on cellular components and, ultimately, on cell growth and viability.

In accordance with the present invention, and without wishing to be bound by theory, the Ru-organic molecule bond or Ru-labeling molecule bond is normally weaker than a covalent σ bond, and therefore can be broken using a lower energy irradiation. Further in accordance with this invention, and without wishing to be bound by theory, the energy required for the release of an organic molecule or a labeling molecule by exposure to light is relatively low. In the Photolabile Compounds of this invention, the organic molecule or labeling molecule is photoreleased by irradiation of the Photolabile Compound using light as described herein.

Also, according to this invention, photorelease can occur in vivo or in a biological sample, e.g., a body fluid, a body sample, such as an organ or tissue sample, in living cells and in the body. Thus, the Photolabile Compounds are especially valuable for in vivo biological applications, such as treatments for various diseases, conditions and disorders of the body. The use of Photolabile Compounds as described herein allows precise control of the onset of a bioactive function or a bioactivity in the body, for example, in living organs, tissues, and cells, i.e., within nanoseconds to milliseconds, with minimal harm to a biological sample, or to the body or its organ, tissue and cellular components. In addition, exposure of a biological sample to light can be localized to the site where an organic molecule is needed or desired. This is particularly beneficial for administration to a subject, particularly a human patient.

The Photolabile Compounds are also suitable for use in non-biological systems, such as in solar cells, photocells, or an optical memory, e.g., a three dimensional optical memory.

In one embodiment, the invention encompasses a compound of Formula I:

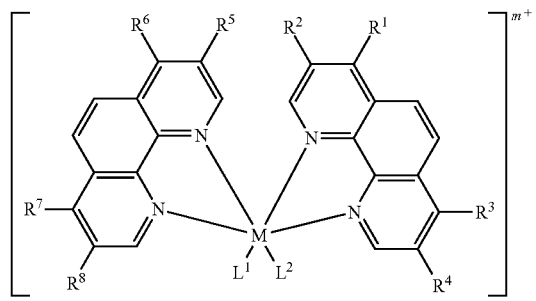

wherein:
$R^1$-$R^8$, $L^1$, $L^2$, X, M and m are as defined above for the compounds of Formula I.

In another embodiment, the invention encompasses a compound of Formula II:

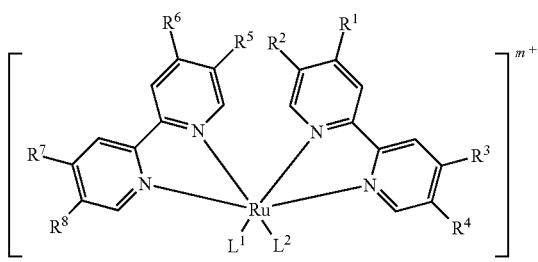

wherein:
$R^1$-$R^8$, $L^1$, $L^2$, X and m are as defined above for the compounds of Formula II.

In another embodiment, the invention encompasses a compound of Formula III:

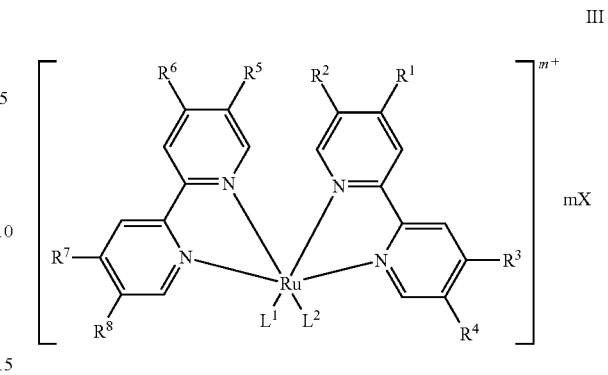

wherein:
$R^1$-$R^8$, $L^1$, $L^2$, X and m are as defined above for the compounds of Formula III.

In another embodiment, the invention encompasses a compound of Formula IV:

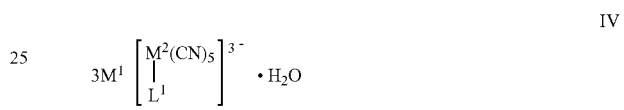

wherein $M^1$, $M^2$, and $L^1$ are as defined above for the compounds of Formula IV.

In one embodiment, the invention encompasses compounds of Formula V:

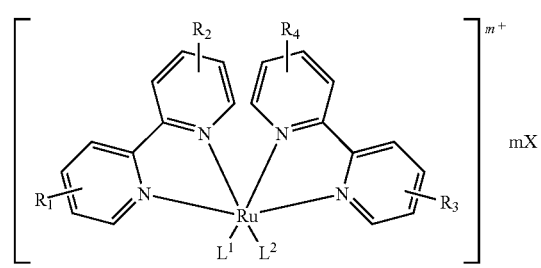

wherein:
$R^1$-$R^4$, $L^1$, $L^2$, X and m are as defined above for the compounds of Formula V.

In another embodiment, the invention encompasses a compound of Formula VI:

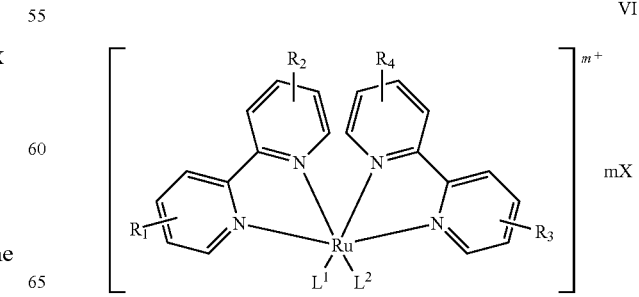

wherein:

$R^1$-$R^4$, $L^1$, $L^2$, X and m are as defined above for the compounds of Formula VI.

In an embodiment, the invention encompasses a compound of Formula VI, wherein $L^2$ is P(phenyl)$_3$ and each phenyl is independently substituted at the 3 or 4 position.

In another embodiment, the invention encompasses a compound of Formula VI, wherein $L^2$ is P(phenyl)$_3$ and at least one phenyl is substituted with —($C_1$-$C_{18}$ alkyl)-OH.

In another embodiment, the invention encompasses a compound of Formula VI, wherein $L^2$ is P(phenyl)$_3$ and each phenyl is substituted with —($C_1$-$C_{18}$ alkyl)-OH.

In another embodiment, the invention encompasses a compound of Formula VI, wherein $L^2$ is P(phenyl)$_3$ and at least one phenyl is substituted with —COOH.

In another embodiment, the invention encompasses a compound of Formula II, wherein $L^2$ is P(phenyl)$_3$ and each phenyl is substituted with —COOH.

In another embodiment, the invention encompasses a compound of Formula VI, wherein $L^2$ is P(phenyl)$_3$ and at least one phenyl is substituted with —OH.

In another embodiment, the invention encompasses a compound of Formula VI, wherein $L^2$ is P(phenyl)$_3$ and each phenyl is substituted with —OH.

In another embodiment, the invention encompasses a compound of Formula VI, wherein $L^2$ is P(phenyl)$_3$ and at least one phenyl is substituted with —NH$_2$.

In another embodiment, the invention encompasses a compound of Formula VI, wherein $L^2$ is P(phenyl)$_3$ and each phenyl is substituted with —NH$_2$.

In another embodiment, the invention encompasses a compound of Formula VI, wherein $L^2$ is P(phenyl)$_3$ and at least one phenyl is substituted with —NO$_2$.

In another embodiment, the invention encompasses a compound of Formula VI, wherein $L^2$ is P(phenyl)$_3$ and each phenyl is substituted with —NO$_2$.

In another embodiment, the invention encompasses a compound of Formula VI, wherein $L^1$ is an organic molecule comprising PMe$_2$ whose phosphorus atom forms a bond with Ru.

In another embodiment, the invention encompasses a compound of Formula VI, wherein $L^1$ is an organic molecule comprising P(phenyl)$_2$ whose phosphorus atom forms a bond with Ru.

In another embodiment, the invention encompasses a compound of Formula VII:

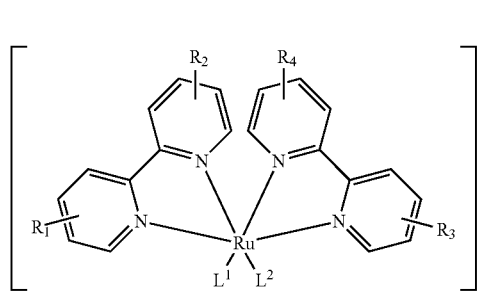

wherein:

$R^1$-$R^4$, $L^1$, $L^2$, X and m are as defined above for the compounds of Formula VII.

In another embodiment, the invention encompasses a compound of Formula VII, wherein $L^2$ is P(methyl)(phenyl)$_2$.

In another embodiment, the invention encompasses a compound of Formula VII, wherein $L^2$ is P(methyl)$_2$(phenyl).

In another embodiment, the invention encompasses a compound of Formula VII, wherein $L^1$ is an organic molecule comprising PMe$_2$ whose phosphorus atom forms a bond with Ru.

In another embodiment, the invention encompasses a compound of Formula VII, wherein $L^1$ is an organic molecule comprising P(phenyl)$_2$ whose phosphorus atom forms a bond with Ru.

In another embodiment, the invention encompasses a compound of Formula VIII:

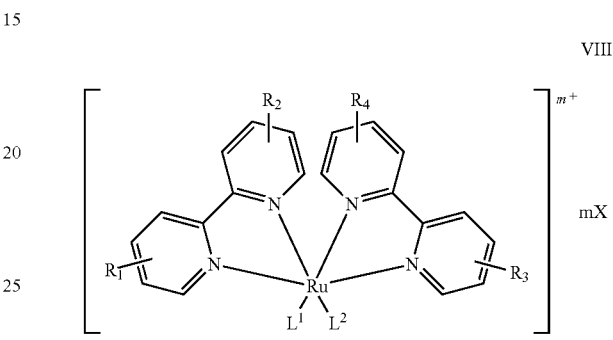

wherein:

$R^1$-$R^4$, $L^1$, $L^2$, X and m are as defined above for the compounds of Formula VIII.

The Photolabile Compounds of Formulas I-VIII can exist in a cis or trans configuration. Accordingly, Formulas I-VIII encompass both cis and trans forms of the Photolabile Compounds.

In the compounds of the present invention, the term "—($C_1$-$C_{18}$) alkyl" refers to a saturated straight or branched non-cyclic hydrocarbon having 1 to 18 carbon atoms. Representative saturated straight chain —($C_1$-$C_{18}$) alkyls include -methyl, -ethyl, -n-propyl, -n-butyl, -n-pentyl, -n-hexyl, -n-heptyl, -n-octyl, -n-nonyl, -n-decyl, -n-undecyl, -n-dodecyl, -n- tridecyl, -n-tetradecyl, -n-pentadecyl, -n-hexadecyl, -n-heptadecyl and -n-octadecyl. Representative saturated branched —($C_1$-$C_{18}$) alkyls include -isopropyl, -sec-butyl, -isobutyl, -tert-butyl, -isopentyl, -2-methylbutyl, -3-methylbutyl, -2,2-dimethylbutyl, -2,3-dimethylbutyl, -2-methylpentyl, -3-methylpentyl, -4-methylpentyl, -2-methylhexyl, -3-methylhexyl, -4-methylhexyl, -5-methylhexyl, -2,3-dimethylbutyl, -2,3-dimethylpentyl, -2,4-dimethylpentyl, -2,2-dimethylhexyl, -2,3-dimethylhexyl, -2,4-dimethylhexyl, -2,5-dimethylhexyl, -2,2-dimethylpentyl, -3,3-dimethylpentyl, -3,3-dimethylhexyl, -4,4-dimethylhexyl, -2-ethylpentyl, -3-ethylpentyl, -2-ethylhexyl, -3-ethylhexyl, -4-ethylhexyl, -2-methyl-2-ethylpentyl, -2-methyl-3-ethylpentyl, -2-methyl-4-ethylpentyl, -2-methyl-2-ethylhexyl, -2-methyl-3-ethylhexyl, -2-methyl-4-ethylhexyl, -2,2-dimethylpentyl, -3,3-diethylhexyl, -2,2-diethylhexyl, -3,3-diethylhexyl and the like.

In the compounds of the present invention, the term "—($C_3$-$C_8$) cycloalkyl" refers to a saturated cyclic hydrocarbon having from 3 to 8 carbon atoms. Representative —($C_3$-$C_8$) cycloalkyls include -cyclopropyl, -cyclobutyl, -cyclopentyl, -cyclohexyl, -cycloheptyl and -cyclooctyl hydrocarbons.

In the compounds of the present invention, the term "aryl" refers to an aromatic group containing 1 to 3 aromatic rings, either fused or linked.

In the compounds of the present invention, the term "heterocyclic group" or "heterocyclic" or "heterocyclyl" or "heterocyclo" as used herein refers to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached to the remainder of the molecule at any heteroatom or carbon atom of the ring or ring system. Exemplary heterocyclic groups include, but are not limited to, azepanyl, azetidinyl, aziridinyl, dioxolanyl, furanyl, furazanyl, homo piperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

The term "cyclic aliphatic amine" or "cyclic aliphatic amine group" as used herein refers to a non-aromatic secondary amine or tertiary cyclic amine group. Examples of cyclic aliphatic amines include, but are not limited to, aziridine and piperidine.

The term "active derivative" or "active derivative of a labeling molecule" as used herein refers to a chemical derivative of a labeling molecule, which retains the labeling function of the labeling molecule (e.g., its fluorescence properties). In some embodiments, such active derivative offers superior properties for attachment to Ru atom through a phosphine group, an aliphatic amine group, an imine group, a pyridyl group, or a nitrile group. A specific example of an active derivative of rhodamine (a labeling molecule) is B-Methylaminopropionitrileamide (RhodB-MAPN). A person of skill in the art can modify the labeling molecule to create a derivative thereof and then test the resultant derivative for activity in the same way that the activity of a labeling molecule is tested to determine whether the derivative is active.

An amino acid group, such as an α-amino acid, is an organic molecule having an amino group (—NH$_2$) and a carboxylic acid group. An amino acid can be one of the 20 common α-amino acids (Gly, Ala, Val, Leu, Ile, Ser, Thr, Asp, Asn, Lys, Glu, Gln, Arg, His, Phe, Cys, Trp, Tyr, Met and Pro), or another naturally occurring amino acid, such as norleucine, ethylglycine, ornithine, gamma-amino butyric acid, and phenylglycine. Other representative amino acids include α-amino-3-hydroxy-5-methyl-4-isoxazolepropionic acid (AMPA).

Examples of a 6-membered monocyclic aromatic ring, wherein one of the ring's members is a nitrogen atom, include a pyridyl, pyrimidinyl, pyridazinyl and pyrazinyl ring.

Examples of a 5-membered monocyclic aromatic ring, wherein one of the ring's members is a nitrogen atom, include a pyrrolyl, imidazolyl, pyrazolyl, triazolyl, tetrazolyl, oxazolyl, oxadiazolyl, thiazolyl and thiadiazolyl ring.

Examples of an 8-10-membered bicyclic aromatic ring, wherein one of the rings is aromatic and has a nitrogen atom member, include an indolizinyl, isoindolyl, 3H-indolyl, indolyl, indazolyl, purinyl, quinolyl, isoquinolyl, phthalazinyl, naphthyridinyl, quinoxalinyl, 1,3,7-trimethyl-2,6-dioxopurinyl, quinazolinyl, cinnolinyl, pteridinyl, 6-amino-1H-purinyl, 2-aminohypoxanthinyl, mercaptopurine, thioguanine, and temozolomide bicyclic aromatic ring.

In general terms, illustrative examples of organic molecules useful in the present Photolabile Compounds embrace a variety of agents, such as pharmaceutical agents, small molecules, drugs, neurochemicals, peptides, proteins, and chemotherapeutic agents, as nonlimiting examples.

Illustrative organic molecules can further include amino acids, luciferin, enzyme inhibitors, fatty acids (e.g., arachidonic acid), protein kinase C activators (e.g., dioctanoylglycerol), tubulin assembly promoters (e.g., paclitaxel), antibiotics (e.g., penicillins or A23187), neurotransmitters (e.g., L-glutamic acid, aspartic acid, carbamylcholine, dopamine, epinephrine, GABA, glutamic acid, glycine, haloperidol, isoproterenol, kainic acid, NMDA, NMDA receptor antagonist MK-801, norepinephrine, phenylephrine, propranolol), 4-aminopyridine (4AP), serotonin (5 hydroxytryptamine, 5HT), (RS)-(tetrazol-5-yl) glycine (TzGly), α-amino-3-hydroxy-5-methyl-4-isoxazoleproprionic acid (AMPA), tetrazolyl-α-amino-3-hydroxy-5-methyl-4-isoxazoleproprionic acid ((tetrazol-5-yl) AMPA), nicotine, nicotinic acid, isoxazole, and fluorescent dyes (e.g., fluorescein, HPTS, rhodamines, succinimidyl esters and sulfosuccinimidyl esters of carboxy-Q-rhodamine, or Rhodamine Green), nucleotides (e.g., ATP, ADP, cAMP, GDP, GTP, cGMP, GTP-γ-S, GDP-β, 8-substituted derivatives of cAMP or cGMP, e.g., 8-bromo-cAMP, 8-bromo-cGMP, 8-chloro-cAMP, 8-chloro-cGMP, 8-parachlorophenylthio (cCPT) cAMP or cGMP, phosphates (e.g., phosphates, phosphate esters), phenylphosphate (PPh$_3$), Py, nucleosides, nucleoside derivatives, nucleotide derivatives (e.g., cADP-ribose, 8-amino-cADP ribose, or 8-bromo-cADP-ribose), cyclitols (e.g., inositol), cyclitol phosphates (e.g., myo-inositol phosphate, myo-inositol-1,4,5-triphosphate, myo-inositol-1,3,4,5-tetrakisphosphate, or myo-inositol-3,4,5,6-tetrakisphosphate), NO (e.g., from the decomposable compound HON=N(O) (Net$_2$)), chelants (e.g., EDTA, EGTA), ionophores (e.g., nigericin), alkylthiogalactose derivatives (e.g., methylthiogalactose, isopropylthiogalactose), mercaptopurine, thioguanine, doxorubicin, cytarabin, temozolomide, gentamicin, and nitrile containing compounds. The organic molecule can be cell permeant, as described, for example, in Furuta et al., *Biochem. Biophys. Res. Commun.*, 228:193-198 (1996).

Other useful examples of organic molecules include adenosine 5'-diphosphate ADP; adenosine 5'-triphosphate ATP; adenosine 5'-monophosphate AMP; aminobutyric acid; L-glutamic acid; cyclic adenosine 5'-diphosphate ribose; adenosine 3',5'-cyclicmonophosphate; fluorescein; methyl-D-aspartic acid; tyramine; tryptophan; 4-aminopyridine (4AP); epinephrine; norepinephrine; dopamine; serotonin (5 hydroxytriptamine, 5HT); (RS)-(tetrazol-5-yl) glycine (TzGly), which is a potent N-methyl-D-aspartate receptor (NMDA) agonist; tetrazolyl-α-amino-3-hydroxy-5-methyl-4-isoxazoleproprionic acid ((tetrazol-5-yl) AMPA); caffeine and nicotine.

In accordance with this invention, the organic molecule ligands glutamate, gamma aminobutyric acid (GABA), alaninate, glycinate and the like have been demonstrated to photorelease from a Photolabile Compound after exposure to visible light; such Photolabile Compounds are stable in solutions in addition to water. Organic molecules having an —$NH_2$ group or an —COOH group may be released in solvents other than water, for example, alcohol (e.g., methanol, ethanol), acetone, etc.

The organic molecule of the invention include phosphorus derivatives with a —$PR_2$ group whose phosphorus atom forms a bond with Ru, wherein R is independently —H, —$C_1$-$C_{18}$ alkyl, or aryl. Exemplary phosphorus derivatives include dimethylphosphinyl, diethylphosphinyl, and diphenylphosphinyl.

The organic molecule of the invention include sulfur derivatives with an —SR group whose sulfur atom forms a bond with Ru, wherein R is independently —H, —$C_1$-$C_{18}$ alkyl, or aryl. Exemplary sulfur derivatives include methyl beta-D-1-thiogalactopyranoside (MTG), isopropyl beta-D-1-thiogalactopyranoside (IPTG), thioethers, thiolates, methylthio, ethylthio, and phenylthio.

The organic molecule of the invention include nitrile derivatives with a-CN group whose nitrogen atom forms a bond with Ru. Exemplary nitrile derivatives include alkyl nitriles, alkenyl nitriles (such as 3-butenenitrile), and aryl nitriles (such as benzonitrile or 2-cyanophenol). Other therapeutic agents containing nitrile groups can also be used as organic molecules.

In general terms, illustrative examples of labeling molecules useful in the present Photolabile Compounds embrace a variety of agents, such as molecules with a fluorescent, a bioluminescent, a chemiluminescent, a colorimetric or a radioactive group, as nonlimiting examples.

A fluorescent molecule can be selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenyl indole (DAPI), indopyra dyes, lucifer yellow, propidium iodide, porphyrins, arginine, and variants and derivatives thereof. For further information on fluorescent label moieties and fluorescence techniques, see, e.g., *Handbook of Fluorescent Probes and Research Chemicals*, by Richard P. Haughland, Sixth Edition, Molecular Probes, (1996), which is hereby incorporated by reference in its entirety.

The Photolabile Compounds of Formulas I-III and V-VIII where $L_2$ is other than $L_1$ can be made by allowing about a molar equivalent of Ru(bdt)$_2$Cl$_2$, where bdt is bipyridine or phenanthroline substituted with an $R_1$-$R_8$ group as defined in Formulas I-III or $R_1$-$R_4$ group as defined in Formulas V-VIII, to react with about a molar equivalent of an organic or labeling molecule in water, ethanol, methanol, isopropyl alcohol, ethylene glycol, acetone, methylene chloride or a mixture thereof at reflux under nitrogen. After about 4 to about 8 hours, the resultant solution is cooled and to it is added at least about an equivalent of $L_2$. The resultant mixture is heated at reflux for about 4 to about 20 h. After cooling to room temperature, the resultant solution is diluted with water, and to it is added excess NH$_4$PF$_6$. The resultant precipitate is filtered, purified via silica-gel chromatography, dried and dissolved in acetone. (n-Bu)$_4$NH$_4^+$ X, wherein X is defined in Formula I-III and V-VIII, is added to the acetone solution, and the resultant Photolabile Compound of Formula I-III and V-VIII where $L_2$ is other than $L_1$ is filtered.

The Photolabile Compounds of Formulas I-III and V-VIII where $L_2$ is $L_1$ can be made by allowing about a molar equivalent of Ru(bdt)$_2$Cl$_2$, where bdt is bipyridine or phenanthroline substituted with an $R_1$-$R_8$ group as defined in Formulas I-IIII or $R_1$-$R_4$ group as defined in Formulas V-VIII, to react with an excess amount of an organic or labeling molecule in water, ethanol, methanol, isopropyl alcohol, ethylene glycol, acetone, methylene chloride or a mixture thereof at reflux under nitrogen. After about 4 to about 8 hours, the resultant solution is cooled to room temperature. The resultant mixture is diluted with water, and to it is added excess NH$_4$PF$_6$. The resultant precipitate is filtered, purified via silica-gel chromatography, dried and dissolved in acetone. (n-Bu)$_4$NH$_4^+$ X, wherein X is defined in I-III and V-VIII, is added to the acetone solution, and the resultant Photolabile Compound of Formula I-III and V-VIII where $L_2$ is $L_1$ is filtered.

The Photolabile Compounds of Formula IV where $M^2$ is Ru can be obtained by dissolving about 1 molar equivalent of $(M^1)_3[M^2(CN)_5NH_3]$ 2H$_2$O, where $M^1$ is defined in Formula IV, in about 15 mL of argon-deoxygenated 1:1 ethanol:water containing about 10 molar equivalents of the organic molecule. The resultant mixture is maintained at about room temperature under argon for about 1 hour and concentrated in vacuo at about room temperature to a volume of about 1 mL. To the resultant concentrate is added a cold, saturated ethanol solution of $M^1$I, resulting in a precipitation of the Photolabile Compounds of Formula IV where $M^2$ is Ru, which are washed with ethanol and diethyl ether.

For the present invention, photorelease can generally occur rapidly, e.g., after about a few nanoseconds to about 500 milliseconds (See Salierno et al., *J Inorg Biochem.* 2010 104(4):418-22) following exposure to visible light of the appropriate wavelength. Suitable wavelengths of light for effective photorelease of an organic molecule or a labeling molecule from a Photolabile Compound range from about 300 to about 500 nm, or from about 300 to about 360 nm, or from about 450 to about 500 nm, e.g., 473 nm and may be extended up to 700 nm. Suitable light sources include those which are capable of irradiating light of the appropriate wavelengths, for example and without limitation, commercially available tungsten lamps (Cole-Parmer), arc lamps, xenon continuous lamps, lasers, e.g., blue or green lasers or photooptic light sources. Such light sources are commercially available (CrystaLaser, Reno, Nev.; Lasever, Jiangdong, Ningbo, China). Other forms of light, such as sunlight, infrared light, pulsed infrared light, or UV radiation can also be used for the invention, as necessary or desired.

Devices and systems suitable for exposing the Photolabile Compounds to light, particularly visible or infrared light, further include imaging probes, imaging catheters and fiber optic probes, particularly those containing gradient index, or graded-index, (GRIN) lenses, which are described in U. Utzinger et al., 2003, *J. Biomed. Optics,* 8(1):121-147; and Fujimoto et al., *Photonic Materials, Devices and Systems—Laser Medicine and Medical Imaging Group,* RLE Progress Report 144, pp 27-1 to 27-35, and which are commercially available. (Sp3 plus, UK). The light suitable for exposing the Photolabile Compounds to photorelease an organic molecule or a labeling molecule comprises a wavelength of about 300 to about 500 nm, or about 300 to about 360 nm, or about 450 to about 500 nm. Suitable light includes visible or infrared light.

Further in accordance with this invention, the organic molecules or labeling molecules can also be released from the Photolabile Compounds via one-photon or two-photon photolysis. Optical memories that utilize a two-photon excitation are described, for example, by Strickler and Webb, 1991, *Optics Letters*, 16:1780-1782. A feature of two-photon excitation is the elimination of out-of-focus background. (See, e.g., W. Denk et al., 1990, *Science*, 248:73-76). Thus, two-photon uncaging can release an organic molecule or a labeling molecule only in the plane of focus. (See, e.g., W. Denk et al., 1994, *Proc. Natl. Acad. Sci. USA*, 91:6629-6633).

In an embodiment, the present invention encompasses a compound of Formula I, wherein the organic molecule is 4-AP. In another embodiment, the invention encompasses a compound of Formula I, wherein the organic molecule is TzGly. In another embodiment, the invention encompasses a compound of Formula I, wherein the organic molecule is (tetrazol-5-yl) AMPA. In another embodiment, the invention encompasses a compound of Formula I, wherein the organic molecule is nicotine or caffeine. In another embodiment, the invention encompasses a compound of Formula I, wherein the organic molecule is serotonin, epinephrine, norepinephrine, or dopamine. In another embodiment, the present invention encompasses a compound of Formula I, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclicmonophosphate. In another embodiment, the invention encompasses a compound of Formula I wherein the organic molecule is aminobutyric acid or L-glutamic acid, or methyl-D-aspartic acid. In another embodiment, the invention encompasses a compound of Formula I wherein the organic molecule is methionine, methylthiogalactose or isopropylthiogalactose. In another embodiment, the invention encompasses a compound of Formula I wherein the organic molecule is methylthiogalactose or isopropylthiogalactose. In another embodiment, the invention encompasses a compound of Formula I wherein the organic molecule is mercaptopurine, thioguanine, doxorubicin, cytarabin, temozolomide, or gentamicin. In another embodiment, the invention encompasses a compound of Formula I wherein the organic molecule is mercaptopurine. In another embodiment, the invention encompasses a compound of Formula I wherein the organic molecule is thioguanine. In another embodiment, the invention encompasses a compound of Formula I wherein the organic molecule is doxorubicin. In another embodiment, the invention encompasses a compound of Formula I wherein the organic molecule is cytarabin. In another embodiment, the invention encompasses a compound of Formula I wherein the organic molecule is temozolomide. In another embodiment, the invention encompasses a compound of Formula I wherein the organic molecule is gentamicin. In another embodiment, the invention encompasses a compound of Formula I wherein the organic molecule is benzonitrile, 2-cyanophenol or 3-butenenitrile.

In an embodiment, the present invention encompasses a compound of Formula II or III, wherein the organic molecule is 4-AP. In another embodiment, the invention encompasses a compound of Formula II, wherein the organic molecule is TzGly. In another embodiment, the invention encompasses a compound of Formula II, wherein the organic molecule is (tetrazol-5-yl) AMPA. In another embodiment, the invention encompasses a compound of Formula II, wherein the organic molecule is nicotine or caffeine. In another embodiment, the invention encompasses a compound of Formula II, wherein the organic molecule is serotonin, epinephrine, norepinephrine, or dopamine. In another embodiment, the present invention encompasses a compound of Formula II, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclicmonophosphate. In another embodiment, the invention encompasses a compound of Formula II, wherein the organic molecule is aminobutyric acid or L-glutamic acid, or methyl-D-aspartic acid. In another embodiment, the invention encompasses a compound of Formula II wherein the organic molecule is methionine, methylthiogalactose or isopropylthiogalactose. In another embodiment, the invention encompasses a compound of Formula II wherein the organic molecule is methylthiogalactose or isopropylthiogalactose. In another embodiment, the invention encompasses a compound of Formula II wherein the organic molecule is mercaptopurine, thioguanine, doxorubicin, cytarabin, temozolomide, or gentamicin. In another embodiment, the invention encompasses a compound of Formula II wherein the organic molecule is mercaptopurine. In another embodiment, the invention encompasses a compound of Formula II wherein the organic molecule is thioguanine. In another embodiment, the invention encompasses a compound of Formula II wherein the organic molecule is doxorubicin. In another embodiment, the invention encompasses a compound of Formula II wherein the organic molecule is cytarabin. In another embodiment, the invention encompasses a compound of Formula II wherein the organic molecule is temozolomide. In another embodiment, the invention encompasses a compound of Formula II wherein the organic molecule is gentamicin. In another embodiment, the invention encompasses a compound of Formula II wherein the organic molecule is benzonitrile, 2-cyanophenol or 3-butenenitrile.

In an embodiment, the present invention encompasses a compound of Formula IV, wherein the organic molecule is 4-AP. In another embodiment, the invention encompasses a compound of Formula IV, wherein the organic molecule TzGly. In another embodiment, the invention encompasses a compound of Formula IV, wherein the organic molecule is (tetrazol-5-yl) AMPA. In another embodiment, the invention encompasses a compound of Formula IV, wherein the organic molecule is nicotine or caffeine. In another embodiment, the invention encompasses a compound of Formula IV, wherein the organic molecule is serotonin, epinephrine, norepinephrine, or dopamine. In another embodiment, the present invention encompasses a compound of Formula IV, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclicmonophosphate. In another embodiment, the invention encompasses a compound of Formula IV, wherein the organic molecule is aminobutyric acid or L-glutamic acid, or methyl-D-aspartic acid. In another embodiment, the invention encompasses a compound of Formula IV wherein the organic molecule is methionine, methylthiogalactose or isopropylthiogalactose. In another embodiment, the invention encompasses a compound of Formula IV wherein the organic molecule is methylthiogalactose or isopropylthiogalactose. In another embodiment, the invention encompasses a compound of Formula IV wherein the organic molecule is mercaptopurine, thioguanine, doxorubicin, cytarabin, temozolomide, or gentamicin. In another embodiment, the invention encompasses a compound of Formula IV wherein the organic molecule is mercaptopurine. In another embodiment, the invention encompasses a compound of Formula IV wherein the organic molecule is thioguanine. In another embodiment, the invention encompasses a compound of Formula IV wherein the organic molecule is doxorubicin. In another embodiment, the invention encompasses a compound of Formula IV wherein the organic molecule is cytarabin. In another embodiment, the invention encompasses a compound of Formula IV wherein the organic molecule is temozolomide. In another embodiment, the invention encompasses a compound of Formula IV wherein the organic molecule is gentamicin. In another embodiment, the invention encompasses a compound of Formula IV wherein the organic molecule is benzonitrile, 2-cyanophenol or 3-butenenitrile.

In an embodiment, the present invention encompasses a compound of Formula V, wherein the organic molecule 4-AP. In another embodiment, the invention encompasses a compound of Formula V, wherein the organic molecule is TzGly. In another embodiment, the invention encompasses a compound of Formula V, wherein the organic molecule is (tetrazol-5-yl) AMPA. In another embodiment, the invention encompasses a compound of Formula V, wherein the organic molecule is nicotine or caffeine. In another embodiment, the invention encompasses a compound of Formula V, wherein the organic molecule is serotonin, epinephrine, norepinephrine, or dopamine. In another embodiment, the present invention encompasses a compound of Formula V, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclicmonophosphate. In another embodiment, the invention encompasses a compound of Formula V wherein the organic molecule is aminobutyric acid or L-glutamic acid, or methyl-D-aspartic acid. In another embodiment, the invention encompasses a compound of Formula V wherein the organic molecule is methionine, methylthiogalactose or isopropylthiogalactose. In another embodiment, the invention encompasses a compound of Formula V wherein the organic molecule is methylthiogalactose or isopropylthiogalactose. In another embodiment, the invention encompasses a compound of Formula V wherein the organic molecule is mercaptopurine, thioguanine, doxorubicin, cytarabin, temozolomide, or gentamicin. In another embodiment, the invention encompasses a compound of Formula V wherein the organic molecule is mercaptopurine. In another embodiment, the invention encompasses a compound of Formula V wherein the organic molecule is thioguanine. In another embodiment, the invention encompasses a compound of Formula V wherein the organic molecule is doxorubicin. In another embodiment, the invention encompasses a compound of Formula V wherein the organic molecule is cytarabin. In another embodiment, the invention encompasses a compound of Formula V wherein the organic molecule is temozolomide. In another embodiment, the invention encompasses a compound of Formula V wherein the organic molecule is gentamicin. In another embodiment, the invention encompasses a compound of Formula V wherein the organic molecule is benzonitrile, 2-cyanophenol or 3-butenenitrile.

In an embodiment, the present invention encompasses a compound of Formula VI, wherein the organic molecule is 4-AP. In another embodiment, the invention encompasses a compound of Formula VI, wherein the organic molecule is TzGly. In another embodiment, the invention encompasses a compound of Formula VI, wherein the organic molecule is (tetrazol-5-yl) AMPA. In another embodiment, the invention encompasses a compound of Formula VI, wherein the organic molecule is nicotine or caffeine. In another embodiment, the invention encompasses a compound of Formula VI, wherein the organic molecule is serotonin, epinephrine, norepinephrine, or dopamine. In another embodiment, the present invention encompasses a compound of Formula VI, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclicmonophosphate. In another embodiment, the invention encompasses a compound of Formula VI wherein the organic molecule is aminobutyric acid or L-glutamic acid, or methyl-D-aspartic acid. In another embodiment, the invention encompasses a compound of Formula VI wherein the organic molecule is methionine, methylthiogalactose or isopropylthiogalactose. In another embodiment, the invention encompasses a compound of Formula VI wherein the organic molecule is methylthiogalactose or isopropylthiogalactose. In another embodiment, the invention encompasses a compound of Formula VI wherein the organic molecule is mercaptopurine, thioguanine, doxorubicin, cytarabin, temozolomide, or gentamicin. In another embodiment, the invention encompasses a compound of Formula VI wherein the organic molecule is mercaptopurine. In another embodiment, the invention encompasses a compound of Formula VI wherein the organic molecule is thioguanine. In another embodiment, the invention encompasses a compound of Formula VI wherein the organic molecule is doxorubicin. In another embodiment, the invention encompasses a compound of Formula VI wherein the organic molecule is cytarabin. In another embodiment, the invention encompasses a compound of Formula VI wherein the organic molecule is temozolomide. In another embodiment, the invention encompasses a compound of Formula VI wherein the organic molecule is gentamicin. In another embodiment, the invention encompasses a compound of Formula VI wherein the organic molecule is benzonitrile, 2-cyanophenol or 3-butenenitrile.

In an embodiment, the present invention encompasses a compound of Formula VII, wherein the organic molecule is 4-AP. In another embodiment, the invention encompasses a compound of Formula VII, wherein the organic molecule is TzGly. In another embodiment, the invention encompasses a compound of Formula VII, wherein the organic molecule is (tetrazol-5-yl) AMPA. In another embodiment, the invention encompasses a compound of Formula VII, wherein the organic molecule is nicotine or caffeine. In another embodiment, the invention encompasses a compound of Formula VII, wherein the organic molecule is serotonin, epinephrine, norepinephrine, or dopamine. In another embodiment, the present invention encompasses a compound of Formula VII, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclicmonophosphate. In another embodiment, the invention encompasses a compound of Formula VII wherein the organic molecule is aminobutyric acid or L-glutamic acid, or methyl-D-aspartic acid. In another embodiment, the invention encompasses a compound of Formula VII wherein the organic molecule is methionine, methylthiogalactose or isopropylthiogalactose. In another embodiment, the invention encompasses a compound of Formula VII wherein the organic molecule is methylthiogalactose or isopropylthiogalactose. In another embodiment, the invention encompasses a compound of Formula VII wherein the organic molecule is mercaptopurine, thioguanine, doxorubicin, cytarabin, temozolomide, or gentamicin. In another embodiment, the invention encompasses a compound of Formula VII wherein the organic molecule is mercaptopurine. In another embodiment, the invention encompasses a compound of Formula VII wherein the organic molecule is thioguanine. In another embodiment, the invention encompasses a compound of Formula VII wherein the organic molecule is doxorubicin. In another embodiment, the invention encompasses a compound of Formula VII wherein the organic molecule is cytarabin. In another embodiment, the invention encompasses a compound of Formula VII wherein the organic molecule is temozolomide. In another embodiment, the invention encompasses a compound of Formula VII wherein the organic molecule is gentamicin. In another embodiment, the invention encompasses a compound of Formula VII wherein the organic molecule is benzonitrile, 2-cyanophenol or 3-butenenitrile.

In an embodiment, the present invention encompasses a compound of Formulas I-III and V-VIII, wherein the labeling molecule is rhodamine. In another embodiment, the invention encompasses a compound of Formulas I-III and V-VIII, wherein the labeling molecule is fluorescein. In another embodiment, the invention encompasses a compound of Formulas I-III and V-VIII, wherein the labeling molecule is iodeosin. In another embodiment, the invention encompasses a compound of Formulas I-III and V-VIII, wherein the labeling molecule is a fluorescent molecule containing a —CN group whose nitrogen atom forms a bond with Ru. In another embodiment, the invention encompasses a compound of Formulas I-III and V-VIII, wherein the labeling molecule is a fluorescent molecule containing a pyridyl group whose nitrogen atom forms a bond with Ru. In another embodiment, the invention encompasses a compound of Formulas I-III and V-VIII, wherein the labeling molecule is a fluorescent molecule containing an amino group whose nitrogen atom forms a bond with Ru. In another embodiment, the invention encompasses a compound of Formulas I-III and V-VIII, wherein the labeling molecule is a fluorescent molecule containing a phosphine group whose nitrogen atom forms a bond with Ru.

In another embodiment, the invention encompasses a compound of Formulas I-III and V-VIII, wherein the labeling molecule is rhodamine containing a —CN group whose nitrogen atom forms a bond with Ru. In another embodiment, the invention encompasses a compound of Formulas I-III and V-VIII, wherein the labeling molecule is rhodamine containing a pyridyl group whose nitrogen atom forms a bond with Ru. In another embodiment, the invention encompasses a compound of Formulas I-III and V-VIII, wherein the labeling molecule is rhodamine containing an amino group whose nitrogen atom forms a bond with Ru. In another embodiment, the invention encompasses a compound of Formulas I-III and V-VIII, wherein the labeling molecule is rhodamine containing a phosphine group whose nitrogen atom forms a bond with Ru.

In some embodiments, of the compounds of Formula I-III and V-VIII, $L^2$ is:

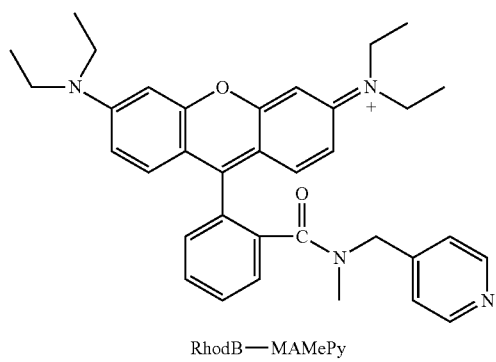

RhodB—MAMePy (RhodB-MAMePy) or a chloride salt thereof (RhodB-MAMePy-Cl).

In some embodiments of the compounds of Formula I-III and V-VIII, $L^2$ is:

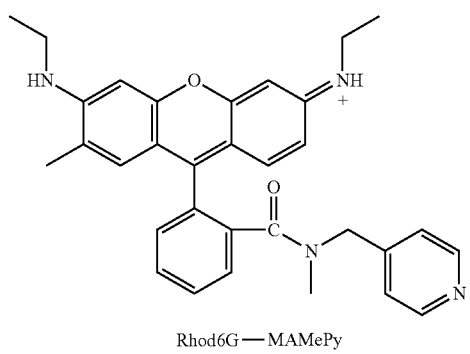

Rhod6G—MAMePy (Rhod6G-MAMePy) or a chloride salt thereof (Rhod6G-MAMePy-Cl).

In some embodiments, the labeling molecule or an active derivative thereof is bonded to Ru to Ru through other coordinating groups: —NH$_2$, pyridyl, or a phosphine group.

In some embodiments of Photolabile Compounds, $L^2$ comprises a labeling molecule or an active derivative thereof, which can serve as a light antenna and can transfer energy to the portion of the compound that effects photorelease of moiety $L^1$. This way the light gathering becomes dissociated from the chemical release step, enabling orthogonal chemical strategies for both processes. Thus, in some embodiments, a Photolabile Compound has a dual functionalization, one being a light antenna and second being a photorelease entity.

In one aspect, a Photolabile Compound can be used in combinatorial chemistry strategies. For example, one could generate a systematic series of derivatives in the photorelease part of the molecule and perform large-scale screening with them. Alternatively or in addition, one could fix the photorelease part of the molecule while derivatizing the light antenna moiety.

In another aspect, the magnetic and/or radio-opaque properties of a Photolabile Compound are used as a means of identifying it or manipulating it in living cells. In one such embodiment, Photolabile Compounds are used as MRI (Magnetic Resonance Imaging) contrast agents.

When $L^2$ comprises a labeling molecule such as a fluorophore or a derivative thereof, $L^2$ can servean antenna, to extend the irradiation spectrum to lower energies with very high absorption and efficiency. In specific embodiments, the fluorescent dye is linked through a derivatization using a non-releasable ligand, i.e., a phosphine (:P(R)$_2$-fluorophore). In these embodiments, the light is collected by the fluorescent moiety acting as an antenna, and transferred to the Ru center, populating the MLCT or d-d excited states. Once the excited state is reached, the other ligand (i.e., $L^1$, which can be a biomolecule or drug) is released.

The fact that in this case the active wavelength is not determined by the Ru center but by the high absorption of the fluorescent dye (~100,000 M$^{-1}$ cm$^{-1}$) allows the tuning of different complexes having different photouncageable drugs at different wavelengths, from 400 to 600 nm, providing orthogonality.

Use of a suitable organic dye coordinated to the ruthenium next to the coordinated fluorescent dye (i.e., a labeling molecule) permits the selective quenching of the fluorescence due to its proximity. In this case, the absorption of light via the Ru-bpy MLCT band (without antenna effect, the fluorescent being quenched by the nearby nonfluorescent dye), can photorelease either the fluorescent dye, increasing dramatically the fluorescence and "uncaging" the fluorophore, or the nonfluorescent quencher, with somewhat similar results (under some conditions, however, the presence of the metallic center can quench the fluorophore).

Further in accordance with the invention, the compounds of Formulas V-VIII, wherein $R^1$ and $R^2$ and/or $R^3$ and $R^4$ combine to form a carbocyclic ring substituted by one or more oxo groups, can attach to surfaces and are useful for the delivery of compounds to surfaces. For example, such compounds can bind to nanoparticles or nanopowders and be used to deliver biologically active organic molecules or labeling molecules. Nanoscale delivery systems have substantial applications in the controlled and targeted transport of drugs. Drugs can be carried selectively to targeted cells by means of nanoparticles with specific surface fictionalization. Nanoparticles can penetrate cell membranes and overcome physiological barriers in the organism, and nanoparticles can also improve the solubility and bio-availability of drugs.

In another embodiment, the invention provides a method for enhancing the solubility of an organic molecule, comprising complexing an organic molecule to a photolabile caging group to form a Photolabile Compound, such that exposing the compound to light under sufficient conditions releases the organic molecule from the compound. In an embodiment, the organic molecule has:

(i) a 5-membered monocyclic aromatic ring, one of the ring's members being a nitrogen atom that forms a bond with Ru;

(ii) a 6-membered monocyclic aromatic ring, one of the ring's members being a nitrogen atom that forms a bond with Ru;

(iii) an 8-10-membered bicyclic ring, one of the bicyclic rings being aromatic and having a nitrogen atom member that forms a bond with Ru;

(iv) an —$NH_2$ group whose nitrogen atom forms a bond with Ru;

(v) a —COOH group, one of whose oxygen atoms forms a bond with Ru;

(vi) a —$PR_2$ group whose phosphorus atom forms a bond with Ru, wherein R is independently —H, —$C_1$-$C_{18}$ alkyl, or aryl;

(vii) an —SR group whose sulfur atom forms a bond with Ru, wherein R is independently —H, —$C_1$-$C_{18}$ alkyl, or aryl; or (viii) a —CN group whose nitrogen atom forms a bond with Ru.

In another embodiment, the organic molecule has:

(i) a 5-membered monocyclic aromatic ring, one of the ring's members being a nitrogen atom that forms a bond with Ru;

(ii) a 6-membered monocyclic aromatic ring, one of the ring's members being a nitrogen atom that forms a bond with Ru;

(iii) an 8-10-membered bicyclic ring, one of the bicyclic rings being aromatic and having a nitrogen atom member that forms a bond with Ru;

(iv) an —$NH_2$ group whose nitrogen atom forms a bond with Ru;

(v) a —COOH group, one of whose oxygen atoms forms a bond with Ru;

(vi) a —$PR_2$ group whose phosphorus atom forms a bond with Ru, wherein R is independently —H, —$C_1$-$C_{18}$ alkyl, or aryl; or (vii) an —SR group whose sulfur atom forms a bond with Ru, wherein R is independently —H, —$C_1$-$C_{18}$ alkyl, or aryl.

In an embodiment, the present invention encompasses a composition comprising an effective amount of a Photolabile Compound and a physiologically acceptable carrier, vehicle, diluent, or excipient. Suitable carriers, vehicles, diluents, or excipients are known to those skilled in the art and include, without limitation, physiologically sterile saline and others as described herein.

In another embodiment, the present invention provides a vessel containing a Photolabile Compound. The vessel can further contain a biological sample, wherein the sample is, for example, hair, an organ specimen; a tissue or cell, for example, a neuronal tissue or cell; a tumor or cancer or neoplastic tissue or cell; or a tissue or cell removed from a patient or subject of interest. Tissue specimens sliced from microtomes, for example, are examples of suitable biological samples.

Any type of vessel that is capable of transmitting the wavelengths of light used for releasing the organic molecules or labeling molecules comprising the Photolabile Compounds, and that is inert to solvent in which a Photolabile Compound is suspended, is suitable for use. For example, the vessel can be made of glass, plastic, acrylic, quartz, a noble metal, etc. In addition, if the vessel is composed of, or encased in, metal, e.g., aluminum, titanium, or stainless steel, exposure to light is performed through the top of the vessel, or through a "window" or other light-penetrable opening in the vessel. For solid-like materials, acrylic plastic or acrylamide-bisacrylamide gel, etc., for example, can be used as media in which the Photolabile Compounds are contained. For example, an acrylic plastic coating formulated using a $CHCl_3$ solution of acrylic and a Ru(bpy) complex changed its spectrum following irradiation, thus allowing photorelease in a solid state. For such solid state aspects of the invention, the temperature may be kept at 4K.

Solvents suitable in which a Photolabile Compounds can be exposed to light include aqueous solvents; water; acetonitrile; alcohol, e.g., methanol, ethanol; acetone; chlorinated solvents such as $CH_2Cl_2$ and $CHCl_3$; or dimethylsulfoxide.

Suitable temperatures at which a Photolabile Compound is exposed to light range, in general, from about 0° C. to about 100-150° C.

In another embodiment, this invention encompasses a method for releasing an organic molecule or a labeling molecule from a Photolabile Compound. The method comprises exposing a Photolabile Compound to light under conditions sufficient to release the organic molecule or labeling molecule from the compound. In the method, the light comprises a wavelength of about 300 to about 500 nm, or about 300 to about 360 nm, or about 450 to about 500 nm. Further, the exposing can occur at a temperature from about 0° C. to about 150° C. In an embodiment, the methods of the invention comprise a Photolabile Compound, e.g., a compound of Formula I-VIII, light of a wavelength of about 300 nm to about 500 nm; $L^1$ being $L^2$, and a temperature of about 0° C. to about 150° C. In another embodiment, the methods comprise a Photolabile Compound, light of a wavelength of about 300 nm to about 360 nm; $L^1$ being $L^2$, and a temperature of about 0° C. to about 150° C. In another embodiment, the methods comprise a Photolabile Compound, light of a wavelength of about 450 nm to about 500 nm; $L^1$ being $L^2$, and a temperature of about 0° C. to about 150° C. In another embodiment, the methods comprise a Photolabile Compound, visible or infrared light; $L^1$ being $L^2$, and a temperature of about 0° C. to about 150° C.

In an embodiment, the invention encompasses a method for assaying an organic molecule, comprising exposing a Photolabile Compound and a biological sample to light under conditions sufficient to release the organic molecule from the Photolabile Compound, and (b) determining an effect of the organic molecule on the biological sample. The sample can be a biological sample, such as a sample excised, removed, or otherwise taken from a subject's body. The subject's biological sample can be, for example, a hair sample, an organ or tissue sample, e.g., from a biopsy or an autopsy, or a cell sample. In addition, the biological sample can be a body fluid sample. Body fluid samples include, without limitation, blood, serum, plasma, lymph, saliva, sputum, tears, semen, or urine. Biological samples can further include, without limitation, brain tissue, brain cells, muscle tissue, muscle cells, muscle fibers, fibroblasts, tissue slices, or fine tissue specimens, from any organ of the body, sarcoplasmic reticulum, skin tissue, membrane preparations or fragments, etc.

The light for exposing the compounds according to the methods of this invention can be sunlight, photo-optic light, or laser light. Advantageously, in the methods of this invention, the light for exposing the compound is other than UV radiation. Thus, for example, the light can be visible light or infrared light, including one-photon and two-photon light. The light can be emitted from a variety of sources, including without limitation, a laser light source, a tungsten light source, a photooptic light source, etc. Another advantage of visible light to expose or irradiate the compounds of the invention relates to the convenience and ability to use a visible light microscope, for example, to view a sample into which a compound is introduced and to microscopically visualize or monitor a photoreleased ligand from the compound after exposure to visible light. Because many microscopes do not transmit UV light, it is advantageous to be able to use a non-quartz microscope in accordance with this invention. Yet another advantage to the use of visible light is that it is not detrimental to living cells and tissues, making it beneficial for in vivo patient use. In addition, for patient use, the light can be specifically directed to an area where a Photolabile Compound is introduced or administered by the use of laser technology, fibers, probes, tubes, and the like. Such probes, fibers, or tubes can be directly inserted, for example, into a body cavity or opening, or under or through the skin, to expose the Photolabile Compound to light.

In another of its embodiments, the present invention includes a method of making an organic molecule bioavailable to a subject. The organic molecule can be made bioavailable to a localized body region or area of the subject, or systemically to the whole body. Local bioavailability of the Photolabile Compounds is achieved, for example, via delivery devices and methods that allow the compounds to be directly administered, for example, inserted into a body cavity, or opening, or through or into the skin. The method of this embodiment involves administering a Photolabile Compound to the subject, and exposing the compound to light under conditions sufficient to release the organic molecule from the compound, thereby making the organic molecule bioavailable to the subject, and/or to a body site or region of the subject. The exposure to light can comprise the use of probes, fibers, tubes, and the like, which allow the light to be specifically directed to the area of interest on or within the body. Alternatively, the Photolabile Compounds can be administered to the patient kept in the dark; for photorelease of the organic molecule, the patient can be moved to the light where exposure to light and photorelease occur. In an embodiment according to this method, the organic molecule has:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru.

In another embodiment according to this method, the organic molecule has:

(a) a 5-membered monocyclic aromatic ring, one of the ring's members being a nitrogen atom that forms a bond with Ru;

(b) a 6-membered monocyclic aromatic ring, one of the ring's members being a nitrogen atom that forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl.

In another embodiment, the organic molecule has:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl;

(g) an —SR group whose sulfur atom forms a bond with Ru, wherein R is independently —H, —$C_1$-$C_{18}$ alkyl, or aryl; or (h) a —CN group whose nitrogen atom forms a bond with Ru.

In another embodiment, the organic molecule has:

(a) a tetrazolyl group, one of its nitrogen atoms forming a bond with Ru;

(b) nicotine or caffeine, whose pyridyl nitrogen atom forms a bond with Ru;

(c) an 8-10-membered bicyclic ring, one of the bicyclic rings being aromatic and having a nitrogen atom member that forms a bond with Ru;

(d) an —$NH_2$ group whose nitrogen atom forms a bond with Ru;

(e) a —COOH group, one of whose oxygen atoms forms a bond with Ru;

(f) a —$PR_2$ group whose phosphorus atom forms a bond with Ru, wherein R is independently —H, —$C_1$-$C_{18}$ alkyl, or aryl; or (g) an —SR group whose sulfur atom forms a bond with Ru, wherein R is independently —H, —$C_1$-$C_{18}$ alkyl, or aryl.

In a related embodiment, the Photolabile Compounds are useful for releasing an organic molecule, such as a drug, pharmaceutical, small biologically active molecule, and the like as described above. Release of the organic molecule from the Photolabile Compound allows the organic molecule to become bioavailable to a subject, or patient, afflicted with a disease, disorder, pathology, or condition. The Photolabile Compounds and organic molecules are useful in veterinary and human medicine. Diseases, disorders, pathologies, or conditions for which making an organic molecule bioavailable would serve to treat, ameliorate, reduce, eliminate, abate, or prevent the disease, disorder, pathology, or condition are further described below and include, as nonlimiting examples, peripheral and central nervous system disorders, neurological disorders and disorders related thereto, neurodegenerative disorders and disorders related thereto, epilepsy, seizures, migraines, headaches, stroke, anxiety, depression, restricted brain function, addictive disorders, neuroses, psychoses, pruritic conditions, Parkinson's disease, Huntington's chorea, cognitive disorders, memory lapses, Alzheimer's disease, dementia, dyskinesia, muscle spasms, retinopathy, vomiting, cancers, neoplasms, tumors, vascular diseases, and cardiovascular diseases.

As further, yet non-limiting examples, the organic molecule is a neurochemical that blocks potassium channels for use, for example, in treating neurodegenerative, or neurological diseases or disorders. In a particular embodiment, the organic molecule is 4-AP, which is a calcium channel blocker. In another embodiment, the organic molecule is TzGly, which is an NMDA-receptor agonist that is more potent than NMDA. In one embodiment, for making an organic molecule of the invention bioavailable to a subject in need thereof, the exposure of the Photolabile Compound to light can occur at the site of the disease, disorder, pathology, or condition, such as a site of a tumor, neoplasm, or cancer lesion or growth, thereby releasing the organic molecule locally and more precisely at the needed location. In another embodiment, for making an organic molecule of the invention bioavailable to a subject in need thereof, the exposure of the Photolabile Compound to light can occur at the sight of a blood dyscrasia.

In other related embodiments, the present invention provides methods for treatment, therapy, and prophylaxis by administering an effective amount of a Photolabile Compound, or a physiologically acceptable composition comprising a Photolabile Compound to a subject, so as to make an organic molecule bioavailable to the subject. The Photolabile Compound can be substantially purified (e.g., substantially free from substances that limit its effect or produce undesired side-effects). Advantageously, for methods in which a Photolabile Compound is administered to a subject, the light, e.g., infrared, laser, or visible light, for photoreleasing the organic molecule to make it bioavailable to the subject can be directed to an internal site or region of interest by using photooptic devices, probes and fibers, such as are known in the art and described supra. Those having skill in the art can employ, manipulate, and internally direct the devices for exposing a Photolabile Compound to light after the Photolabile Compound is administered to a subject.

In the methods of the present invention involving subjects, and/or the treatment, therapy, or prophylaxis of a disease, disorder, pathology, or condition, the subject is preferably an animal, including but not limited to, mammals such as human and non-human primates, cows, pigs, horses, goats, sheep, rabbits, chickens, cats, dogs, guinea pigs, rats, mice, etc. The methods of the invention especially encompass human treatments.

Various delivery systems are known and can be used to administer a Photolabile Compound, e.g., in sterile solution, encapsulation in liposomes, microparticles, microcapsules, or receptor-mediated endocytosis (See, e.g., Wu and Wu, 1987, *J. Biol. Chem.*, 262:4429-4432). Methods of introduction include, but are not limited to, intradermal, intramuscular, intraperitoneal, intravenous, subcutaneous, intranasal, epidural, topical, transdermal, parenteral, intrathecal, vaginal, rectal, colorectal, oral, intracranial, retroorbital, intrasternal routes, or a combination thereof.

The Photolabile Compounds or compositions may be administered by any convenient route or mode, for example, by continuous infusion, non-continuous infusion, or bolus injection, by absorption through epithelial or mucocutaneous linings (e.g., oral mucosa, epidermis, rectal and intestinal mucosa, etc.) and may be administered together with other biologically active and/or therapeutic agents. Administration can be systemic or local. In addition, it may be desirable to introduce the Photolabile Compounds or compositions into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a particular embodiment, it may be desirable to administer the Photolabile Compounds or compositions locally to the area in need of treatment. This may be achieved, for example, by local infusion during surgery, topical application, e.g., in conjunction with a wound dressing after surgery, by injection, by means of a catheter, by means of a suppository, or by means of an implant, where the implant is a porous, non-porous, or gelatinous material, including membranes, such as sialastic membranes, or fibers.

In another embodiment involving topical administration, a transdermal patch can be used. In accordance with this embodiment, the Photolabile Compound remains unexposed to light until the patch is manipulated by a patient or medical provider so that all or a portion of the patch containing a Photolabile Compound is exposed to light. Accordingly, the patch can be opened and the bioactive molecule released, or "activated" from the compound after exposure to light, for example, by the patient's moving from a dark room to a lighted room, or from a dark area to a light area; by the patient's directly exposing the patch, or a portion thereof, to a suitable light source, or by the patient's exposing all or a portion of the patch to daylight. A variety of types of transdermal patches are known and used by the skilled practitioner in the art. Alternatively for topical administration, a Photolabile Compound can be formulated into a light-sensitive composition, which is contained in a dark, light-protected container, and applied topically to the area of interest, e.g., applied to or rubbed onto the skin of a subject, in the dark. Following topical application in the dark, the area of interest is exposed to light, or to an appropriate light source, or the subject moves into the light, thereby causing the organic molecule of the Photolabile Compound to be released.

In another embodiment, the Photolabile Compounds or compositions can be delivered in a vesicle, in particular a liposome (See, e.g., Langer, 1990, Science, 249:1527-1533; Treat et al., In: Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.) In yet another embodiment, the Photolabile Compounds or compositions can be delivered in a controlled-release system. For example, a pump may be used (see Langer, supra; Sefton, 1987, *CRC Crit. Ref. Biomed. Eng.* 14:201; Buchwald et al., 1980, *Surgery,* 88:507; Saudek et al., 1989, *NEJM, Med.* 321:574 (1989)), or polymeric materials can be used (See, e.g., Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.,* 23:61; Levy et al., 1985, *Science,* 228:190; During et al., 1989, *Neurol.,* 25:351; and Howard et al., 1989, *J. Neurosurg.,* 71:105). Moreover, a controlled-release system can be placed proximal to the therapeutic target, e.g., the brain, thus requiring only a fraction of the systemic dose (see, e.g., Goodson, 1984, In: Medical Applications of Controlled Release, Vol. 2, pp. 115-138). As further guidance, other controlled release systems are found in Langer, 1990, *Science,* 249:1527-1533.

The Photolabile Compounds are also provided in effective amounts in pharmaceutical compositions comprising a pharmaceutically acceptable carrier, diluent, excipient, or vehicle, for example, for use as therapeutics. In one embodiment, the term "pharmaceutically acceptable" refers to approval by a regulatory agency of the Federal or a state government, or listed in the U.S. Pharmacopeia or other generally recognized pharmacopeia for use in animals, and more particularly, in humans. The terms vehicle, carrier, or excipient refer to a diluent or adjuvant in or with which the therapeutic is administered. Such pharmaceutical carriers, vehicles, or excipients can be sterile liquids, such as water and oils, including those of petroleum, animal, vegetable or synthetic origin, e.g., peanut oil, soybean oil, mineral oil, sesame oil and the like. Water is a preferred carrier when a pharmaceutical composition is administered intravenously and is water soluble. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. If needed or desired, the composition of the invention can also contain minor amounts of wetting or emulsifying agents, or pH buffering agents.

The Photolabile Compounds and compositions of the present invention can be formulated as solutions, suspensions, emulsions, tablets, pills, capsules, powders, sustained-release formulations and the like. The compositions can be formulated as a suppository, with traditional binders and carriers such as triglycerides. Oral formulations can include standard carriers, such as pharmaceutical grades of mannitol, lactose, starch, magnesium stearate, sodium saccharine, cellulose, magnesium carbonate, etc. Examples of suitable pharmaceutical carriers and the like are described in the current edition of "Remington's Pharmaceutical Sciences" by E. W. Martin. Such compositions routinely contain a therapeutically effective amount of the Photolabile Compound, preferably in purified form, together with a suitable amount of carrier so as to provide the form for proper administration to a subject. The formulation should suit the mode of administration.

In another embodiment, a Photolabile Compound of the invention is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container, such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. Sterility for of a composition for therapeutic administration is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle. Therapeutics are typically stored in unit or multi-dose containers, for example, sealed ampoules or vials, as an aqueous solution or as a lyophilized formulation for reconstitution. Where necessary, the ampoule or vial is essentially impenetrable by light. As an example of a lyophilized therapeutic formulation, 10-ml vials are filled with 5 ml of sterile-filtered 1% (w/v) aqueous therapeutic solution, and the resulting mixture is lyophilized. The infusion solution is prepared by reconstituting the lyophilized therapeutic using bacteriostatic Water-for-Injection.

The amount of a Photolabile Compound which will be effective in the treatment, amelioration, reduction, elimination, inhibition, or prevention of a particular disease, condition, pathology, or disorder associated with the use and bioactivity of an organic molecule can be determined by standard clinical techniques. An "effective amount" or a "pharmaceutically effective amount" of a Photolabile Compound of this invention refers to an amount effective for treating, ameliorating, reducing, abating, eliminating, preventing, a disease, condition, pathology, or disorder for which the compound is being used. In particular embodiments, an effective amount is an amount effective for making an organic molecule of the invention bioavailable to a subject. If another therapeutic agent is used in conjunction with the Photolabile Compounds, the effective amount of the therapeutic agent refers to an amount effective for providing the therapeutic effect of the therapeutic agent. The precise dose to be employed in the formulation will also depend on the route of administration, as well as an individual patient's circumstances, such as age, health and vital statistics of the patient, and the severity of the disease, condition, or disorder. Dosing should be decided according to the judgment of the medical practitioner based on an evaluation of the patient and considerations of a patient's physiologic situation and medical history. In addition, in vitro assays may optionally be used to assist in determining optimal dosage ranges. Effective doses can be extrapolated from dose-response curves derived from in vitro or in vivo animal model test systems.

As general guidance, the total effective amount of a Photolabile Compound administered parenterally per dose will be in the range of about 1 µg/kg/day to 10 mg/kg/day of a subject's body weight, although, as noted above, this will be subject to discretion based on the subject's condition and the above-mentioned variables. A therapeutic dose can also be at least 0.01 mg/kg/day, or between about 0.01 and 1 mg/kg/day, with particular regard for human administration. If given continuously, a therapeutic is typically administered at a dose rate of about 1 µg/kg/hour to about 50 µg/kg/hour, either by 1 to 4 injections per day or by continuous subcutaneous infusions, e.g., using a mini-pump. An intravenous bag solution may also be employed. The length of treatment needed to observe changes and the interval following treatment for responses to occur will likely vary depending on the desired effect. In some embodiments, suitable effective dosage amounts range from about 10 µg to about 2500 mg about every 4 hours, although the amounts are typically about 100 mg or less. In one embodiment, the effective dosage of a Photolabile Compound ranges from about 0.01 mg to about 100 mg about every 4 hours. In another embodiment, the effective dosage of a compound of the invention ranges from about 0.020 mg to about 50 mg every 4 hours, and in another embodiment, about 0.025 mg to about 20 mg about every 4 hours. The effective dosage amounts refer to total amounts administered. Thus, if more than one of the Photolabile Compounds is administered, the effective dosage amounts correspond to the total amount administered.

In another embodiment, if a Photolabile Compound is contacted with a biological sample in vitro, an effective amount will typically range from about 0.01 µg/L to about 5 mg/L; in another embodiment from about 0.01 µg/L to about 2.5 mg/L; in another embodiment, from about 0.01 µg/L to about 0.5 mg/L; and in yet another embodiment, from about 0.01 µg/L to about 0.25 mg/L of a solution or suspension of a pharmaceutically acceptable carrier, diluent, or excipient. In an embodiment, the volume of solution or suspension is from about 1 µL to about 1 mL; in another embodiment, the volume of solution or suspension is about 200 µL.

Examples of neoplastic or hyperproliferative diseases, disorders, pathologies, or conditions that can be treated, ameliorated, reduced, abated, eliminated, inhibited, prevented, and/or diagnosed using the Photolabile Compounds and photoreleased organic molecules include, but are not limited to, neoplasms (cancers or tumors) located in the colon, abdomen, bone, breast, digestive system, esophagus, liver, pancreas, peritoneum, endocrine glands (adrenal, parathyroid, pituitary, testicles, ovaries, cervix, thymus, thyroid), eye, head and neck, nervous (central and peripheral), lymphatic system, pelvis, skin, soft tissue, spleen, thoracic areas, bladder, and urogenital system. Cancers that may be treatable using the Photolabile Compounds include follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer, or metastases thereof. Autoimmune diseases, disorders, or conditions may be treatable with the Photolabile Compounds and include multiple sclerosis, Sjogren's syndrome, Hashimoto's thyroiditis, biliary cirrhosis, Bechet's disease, Crohn's disease, polymyositis, systemic lupus erythematosus and immune-related glomerulonephritis, rheumatoid arthritis, ischemic injury (e.g., caused by myocardial infarction, stroke and reperfusion injury), liver injury (e.g., hepatitis related liver injury, ischemia/reperfusion injury, cholestosis (bile duct injury) and liver cancer); toxin-induced liver disease (e.g., caused by alcohol), septic shock, cachexia and anorexia. Viral infections (such as herpes viruses, pox viruses and adenoviruses), inflammation, graft versus host (GVH) disease, acute graft rejection, and chronic graft rejection may also be treatable with the Photolabile Compounds.

Additional diseases or conditions associated with abnormal and increased cell survival that may be treated, ameliorated, reduced, abated, eliminated, inhibited, prevented, and/or diagnosed using the Photolabile Compounds include, but are not limited to, progression and/or metastases of malignancies and related disorders such as leukemia (including acute leukemias (e.g., acute lymphocytic leukemia, acute myelocytic leukemia, including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In another embodiment, the Photolabile Compounds may be needed as therapeutics to stimulate epithelial cell proliferation and basal keratinocytes for the purpose of wound healing, and to stimulate hair follicle production and the healing of dermal wounds. The Photolabile Compounds of the invention may be clinically useful in stimulating wound healing, including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment using steroids, radiation therapy, anti-neoplastic drugs and anti-metabolites.

Other diseases, disorders, or conditions that may be treated, ameliorated, reduced, abated, eliminated, inhibited, prevented, and/or diagnosed with the Photolabile Compounds include AIDS; neurodegenerative diseases, disorders, and/or conditions (such as Alzheimer's disease, Parkinson's disease, amyotrophic lateral sclerosis (ALS), multiple sclerosis, Retinitis pigmentosa (RP), cerebellar degeneration and brain tumor or prior associated disease).

In one embodiment, diseases and conditions that are treatable using calcium channel blockers, e.g., 4AP, include without limitation, heart disease, hypertension, angina, chest pain, cardiovascular diseases, such as coronary artery disease, cardiomyopathies, valvular heart disease, renal disease, Peyronie's disease and neurological, neurophysiological, or neuromuscular diseases and conditions, e.g., amyotrophic lateral sclerosis (ALS), multiple sclerosis, and epilepsy.

In another embodiment, diseases that are treatable using NMDA receptor agonists or antagonists, e.g., TzGly, include without limitation, neurological, neurodegenerative, or neurophysiological diseases, disorders, and conditions, such as Alzheimer's disease, Parkinson's disease, Huntington's disease, and dyskinesias. In another embodiment, neurological, neurodegenerative, and neurophysiological diseases, e.g., Parkinson's disease, Alzheimer's disease, etc., are treatable using Tz-AMPA.

In another embodiment, the present invention relates to kits comprising a Photolabile Compound and instructions for use. A kit may be used in a diagnostic, screening, or testing assay. A kit may also be a pharmaceutical pack, particularly for use in treating or preventing a disease, disorder, pathology, or condition. A kit for pharmaceutical use is typically sterile and contains a Photolabile Compound in an amount effective to treat or prevent a disease, disorder, pathology, or condition, and a pharmaceutically acceptable carrier, diluent, or excipient. The kit, or a pharmaceutical pack, can comprise one or more vessels or containers filled with an effective amount, e.g., unit dosage form, of one or more of the Photolabile Compounds or compositions of the invention, and a pharmaceutically acceptable carrier, diluent, or excipient. The kit, or pharmaceutical pack, can further comprise a label. In addition, the kit, or pharmaceutical pack, can also include a unit dosage form of another therapeutic agent, for example, a container containing an effective amount of the other therapeutic agent. The kit, or pharmaceutical pack, may further optionally contain a notice in the form prescribed by a governmental agency regulating the manufacture, use, or sale of pharmaceuticals or biological products, reflecting approval by the agency of manufacture, use or sale for human administration. The kit, or pharmaceutical pack, can also contain a device useful for administering the unit dosage forms. Examples of such devices include, without limitation, a syringe, a drip bag, a patch, an inhaler, and an enema bag or container.

EXAMPLES

The examples described below are provided to illustrate the present invention and are not included for the purpose of limiting the invention.

Example 1

Synthesis of [Ru(bpy)$_2$(4AP)$_2$]Cl$_2$ 159 mg of Ru(bpy)$_2$Cl$_2$, where bpy=2,2'-bipyridine, were suspended in 7 mL of water at 85° C. under N$_2$. After dissolution, 66 mg of 4-aminopyridine ("4AP") were added, and the resultant solution was heated for about 20 minutes at about 50-80° C. or greater. A molar excess of NH$_4$PF$_6$, was added, and the resultant red solid was washed with water and dried. The red solid was dissolved in a minimal amount of acetone, and to the acetone solution was added tetraethylammonium chloride, precipitating [Ru(bpy)$_2$(4AP)$_2$]Cl$_2$ (79% yield).

Example 2

Synthesis of [Ru(bpy)$_2$(TzGly)$_2$]Cl$_2$

[Ru(bpy)$_2$(TzGly)$_2$]Cl$_2$ was made according to the procedure used to make [Ru(bpy)$_2$(4AP)$_2$]Cl$_2$ set forth in Example 1, except that (RS)-(tetrazol-5-yl)glycine ("TzGly") was used in place of 4AP.

Example 3

Synthesis of [Ru(bpy)$_2$(5HT)$_2$]Cl$_2$

[Ru(bpy)$_2$(5HT)$_2$]Cl$_2$ is made according to the procedure used to make [Ru(bpy)$_2$(4AP)$_2$]Cl$_2$ set forth in Example 1, except that serotonin ("5HT") is used in place of 4AP.

Example 4

Synthesis of [Ru(bpy)$_2$(4AP)(PPh$_3$)]Cl$_2$

Ru(bpy)$_2$Cl$_2$, where bpy=2,2'-bipyridine, was suspended in water at a concentration of 10 mg/mL at 85° C. under N$_2$. After dissolution, 1 equivalent of PPh$_3$ was added, and the resultant solution was heated for about 60 minutes at about 50-80° C. or greater. 1.1 Equivalents of 4AP were subsequently added, and heating continued for an additional 30 minutes. A molar excess of NH$_4$PF$_6$, was added, and the resultant orange solid was washed with water and dried. The orange was dissolved in a minimal amount of acetone, and to the acetone solution was added tetraethylammonium chloride, precipitating [Ru(bpy)$_2$(4AP)(PPh$_3$)]Cl$_2$.

Example 5

Synthesis of [Ru(bpy)$_2$(TzGly)(PPh$_3$)]Cl$_2$

[Ru(bpy)$_2$(TzGly)(PPh$_3$)]Cl$_2$ was made according to the procedure used to make [Ru(bpy)$_2$(4AP)(PPh$_3$)]Cl$_2$ set forth in Example 4, except that TzGly was used in place of 4AP.

Example 6

Synthesis of [Ru(bpy)$_2$(5HT)(PPh$_3$)]Cl$_2$

[Ru(bpy)$_2$(5HT)(PPh$_3$)]Cl$_2$ is made according to the procedure used to make [Ru(bpy)$_2$(4AP)(PPh$_3$)]Cl$_2$ set forth in Example 4, except that serotonin is used in place of 4AP.

Example 7

Synthesis of [Ru(bpy)$_2$(nicotine)(PPh$_3$)]Cl$_2$

[Ru(bpy)$_2$(nicotine)(PPh$_3$)]Cl$_2$ is made according to the procedure used to make [Ru(bpy)$_2$(4AP)(PPh$_3$)]Cl$_2$ set forth in Example 4, except that nicotine is used in place of 4AP.

Example 8

Synthesis of [Ru(bpy)$_2$(TzGly)(py)]Cl$_2$

[Ru(bpy)$_2$(TzGly)(py)]Cl$_2$, where py=pyridine, was made according to the procedure used to make [Ru(bpy)$_2$(4AP)(PPh$_3$)]Cl$_2$ set forth in Example 4, except that TzGly was used in place of 4AP and pyridine was used in place of PPh$_3$.

Example 9

Synthesis of [Ru(bpy)$_2$(4AP)(py)]Cl$_2$

[Ru(bpy)$_2$(4AP)(py)]Cl$_2$, where py=pyridine, is made according to the procedure used to make [Ru(bpy)$_2$(4AP)(PPh$_3$)]Cl$_2$ set forth in Example 4, except that pyridine is used in place of PPh$_3$.

Example 10

Synthesis of [Ru(bpy)$_2$(5HT)(py)]Cl$_2$

[Ru(bpy)$_2$(5HT)(py)]Cl$_2$, where py=pyridine, is made according to the procedure used to make [Ru(bpy)$_2$(4AP)(PPh$_3$)]Cl$_2$ set forth in Example 4, except that 5HT is used in place of 4AP and pyridine is used in place of PPh$_3$.

Example 11

Synthesis of [Ru(bpy)$_2$(nicotine)(py)]Cl$_2$

[Ru(bpy)$_2$(nicotine)(py)]Cl$_2$, where py=pyridine, is made according to the procedure used to make [Ru(bpy)$_2$(4AP)(PPh$_3$)]Cl$_2$ set forth in Example 4, except that nicotine is used in place of 4AP and pyridine is used in place of PPh$_3$.

Example 12

Synthesis of Co(DMG)$_2$(5HT)(Cl)

CoCl$_2$ was dissolved in a 1:1 v/v mixture of water/ethanol at a final concentration of about 0.2 M. Two equivalents of dimethylglyoxime ("DMG") were added, and the resultant mixture was allowed to stir under N$_2$ until dissolution. One equivalent of 5HT was added, air was bubbled into the resultant mixture for 6 hours and Co(DMG)$_2$(5HT)(Cl) precipitated. The precipitated product was filtered and washed.

Example 13

Photorelease of 4AP from [Ru(bpy)$_2$(4AP)$_2$]Cl$_2$

UV-vis spectra in water were obtained with an HP 8453 diode array spectrophotometer. RMN $^1$H spectra were obtained using a Bruker 500 MHz equipment. CV measurements were performed with a PAR 273A potentiostat. Irradiation was effected by means of a pulsed Xe lamp, (pulse energy ~0.5 J), with a low-pass filter at 480 nm. Irradiation using a 473 nm DPSS laser gave similar results.

[Ru(bpy)$_2$(4AP)$_2$]Cl$_2$ is very soluble in water and stable in the dark, while undergoing decomposition under irradiation with visible light in its metal-to-ligand charge transfer (MLCT) band, centered at 489 nm. (In CH$_3$CN solution, the absorption band is red-shifted to 492 nm, consistent with the lower polarity of the solvent, despite a previous characterization that reported 450 nm. However, light exposure of a CH$_3$CN solution of [Ru(bpy)$_2$(4AP)$_2$]Cl$_2$ produced a yellow compound with absorption maximum at 450 nm. This may correspond to the previously misinterpreted assignments for this compound (D. Chun-Ying et al., 1999, *J. Coord. Chem.*, 46:301-312), and the photoproduct is likely to be the complex [Ru(bpy)$_2$(4AP)CH$_3$CN]$^{2+}$). Several ruthenium polypyridyl complexes present this behavior. (D. V. Pinnick et al., 1984, *Inorg. Chem.*, 23:1440-1445).

Although at pH 7 the spectrum of the irradiated complex is very similar to that of the original complex, a diminished shoulder at 470 nm becomes evident. To determine the nature of the photoreaction, NMR spectra were taken before and after irradiation with visible light. FIG. 1 shows the signal assigned to the meta hydrogens [Ru(bpy)$_2$(4AP)$_2$]Cl$_2$ (m1). After irradiation, this signal decreased, and two new signals appeared at lower fields: one corresponding to the free ligand (m3), and the other corresponding to the aquo-4AP complex (m2), indicating photorelease of the 4AP. These two latter signals integrated for 0.30 and 0.27 of the initial signal, which corresponds to a photoreaction of 60%.

The redox potential of the couple $R^{III}/R^{II}$ for [Ru(bpy)$_2$(4AP)$_2$]Cl$_2$ measured in water is E=0.76 V versus Ag/AgCl, which is consistent with the higher basicity of 4AP compared with that of pyridine. Thus, the redox and the photochemistry of [Ru(bpy)$_2$(4AP)$_2$]Cl$_2$ is in total agreement with results obtained corresponding to the Ru(bpy)$_2$XY family, X and Y being monodentate ligands. (See, e.g., E. S. Dodsworth et al., 1986, *Chem. Phys. Lett.*, 124:152-158). The photoactivity of these compounds has been explained in terms of a reaction pathway that involves the transition between the MLCT state to a lower-energy d-d state, which promotes ligand release. There is a direct correspondence between the energy of the MLCT transition and the quantum yield of the photoreaction. For [Ru(bpy)$_2$(4AP)CH$_3$CN]$^{2+}$, the photoreaction yield is about $\phi_{PR}$=0.4. Since [Ru(bpy)$_2$(4AP)$_2$]Cl$_2$ presents a red-shifted band, a lower photoreaction yield is expected. An estimate based on early experiments leads to an estimate of $\phi_{PR} \cong 0.02$ at 473 nm.

Example 14

Neurophysiological Activity of 4AP Photoreleased from [Ru(bpy)$_2$(4AP)$_2$]Cl$_2$ A standard setup for intracellular voltage measurements was used, and the medicinal leech *Hirudo medicinalis* was used to demonstrate photoreleased 4AP's neurophysiological activity. *Hirudo medicinalis* has a central nerve cord with several ganglia, each one containing about 400 neurons arranged in a known pattern. (W.-R. Schlue et al., 1980, *J. Exp. Biol.*, 82:23-34). An entire ganglion was mounted on a dish. The transmembrane potential for a single cell (a neuron) in the ganglion was recorded by inserting inside the neuron a glass micropipet with a micrometer-sized end, filled with saturated aqueous KCl that acts as a luggin bridge for an Ag/AgCl electrode. Another Ag/AgCl electrode was used as a reference. The signal was taken with an AM-System 1600 amplifier, and the entire setup was covered with a Faraday cage. A 12 bit A/D acquisition card was used to digitize the data using an ad-hoc program written in QuickBasic.

Figure 2:
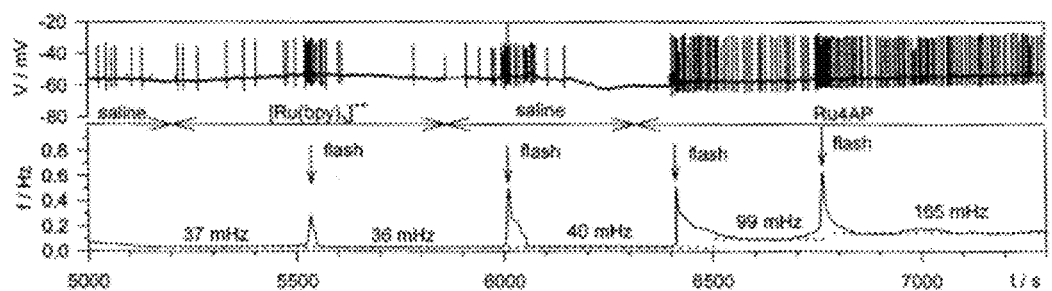
FIG. 2 (Top) shows action potentials (spikes) recorded in a medicinal leech (Hirudo medicinalis) neuron for saline and solutions of [Ru(bpy)$_3$]Cl$_2$ and [Ru(bpy)$_2$(4AP)$_2$]Cl$_2$ (Bottom): Frequency of the spikes. Arrows indicate irradiation with Xe flashlamp. (Middle): Composition of the extracellular medium.
Figure 3:
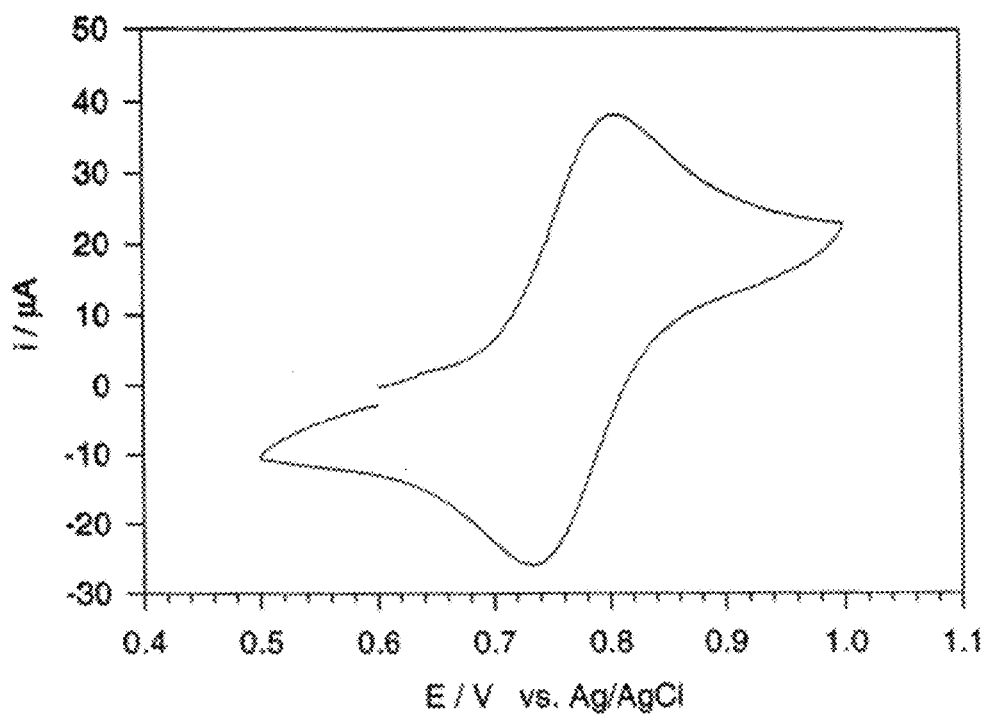
FIG. 3 shows cyclic voltammetry (CV) profile of [Ru(bpy)$_2$(4AP)$_2$]Cl$_2$ in water. The supporting electrolyte was KNO$_3$ (1 M). dE/dt=100 mV/s in glassy carbon electrode.
Figure 4A:
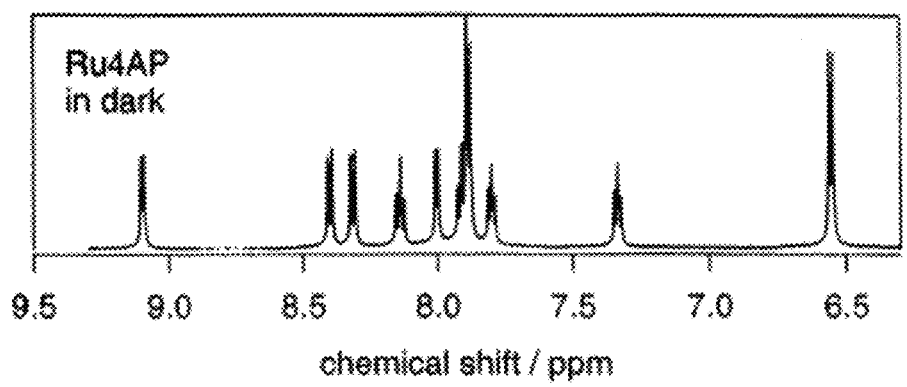
FIGS. 4A and 4B show NMR spectra of [Ru(bpy)$_2$(4AP)$_2$]Cl$_2$ in D$_2$O before (FIG. 4A) and after (FIG. 4B) irradiation. Bruker 500 MHz.
Figure 4B:
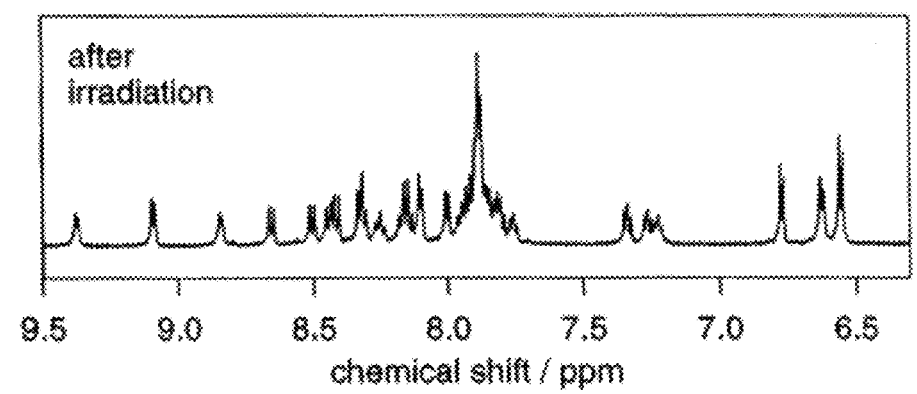
Figure 5:
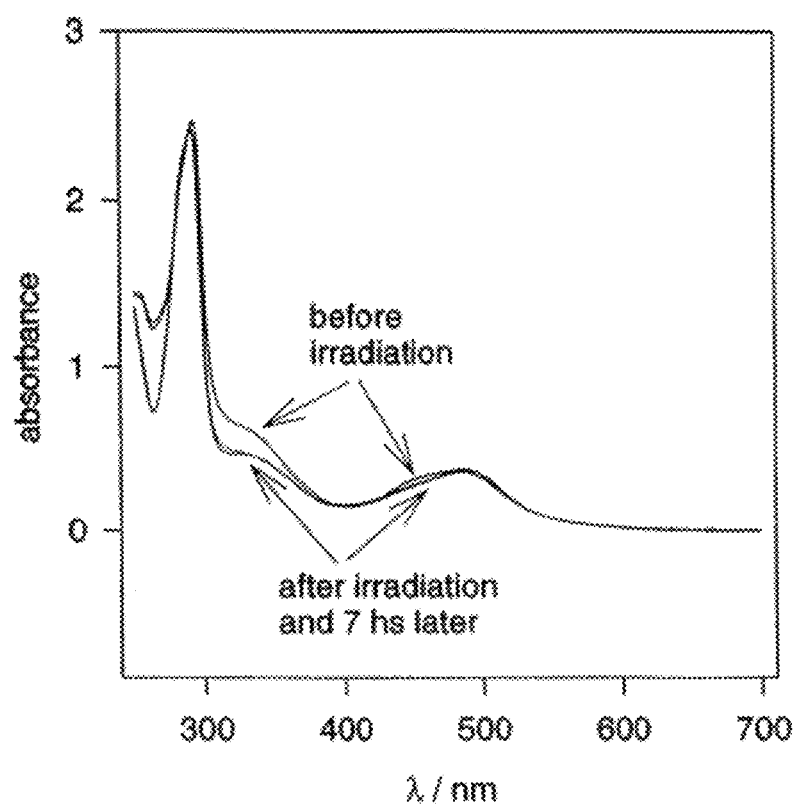
FIG. 5 shows the UV-visible (UV-vis) spectra of Ru(bpy)$_2$(4AP)$_2$ before and after complete photolysis. The photoproducts after exposure to light were Ru(bpy)$_2$(4AP)(H$_2$O) and free 4AP. The complex did not undergo dark decomposition for more than 20 hours. After 7 hours in the dark, the irradiated solution showed less than 4% of 4AP recombination.
Figure 6:
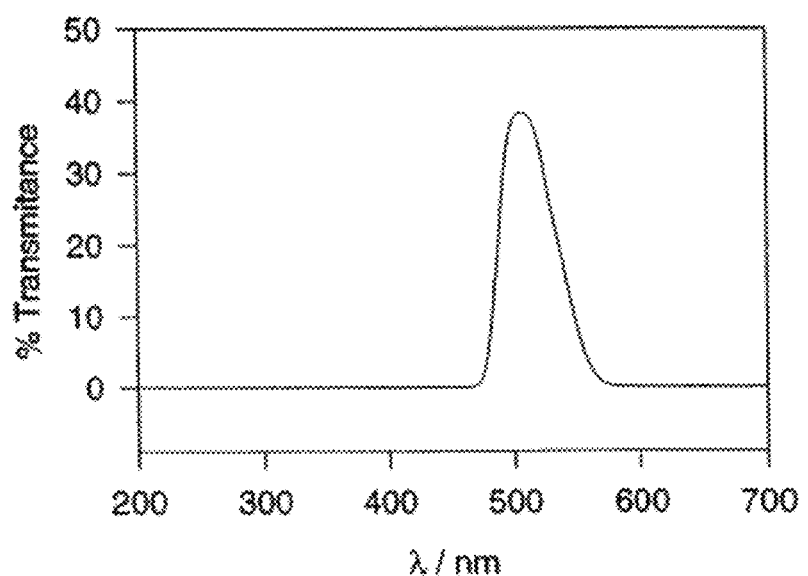
FIG. 6 shows a UV-vis spectrum of the filter used for the ganglion irradiation experiments as described in Example 3.
Figure 7A:
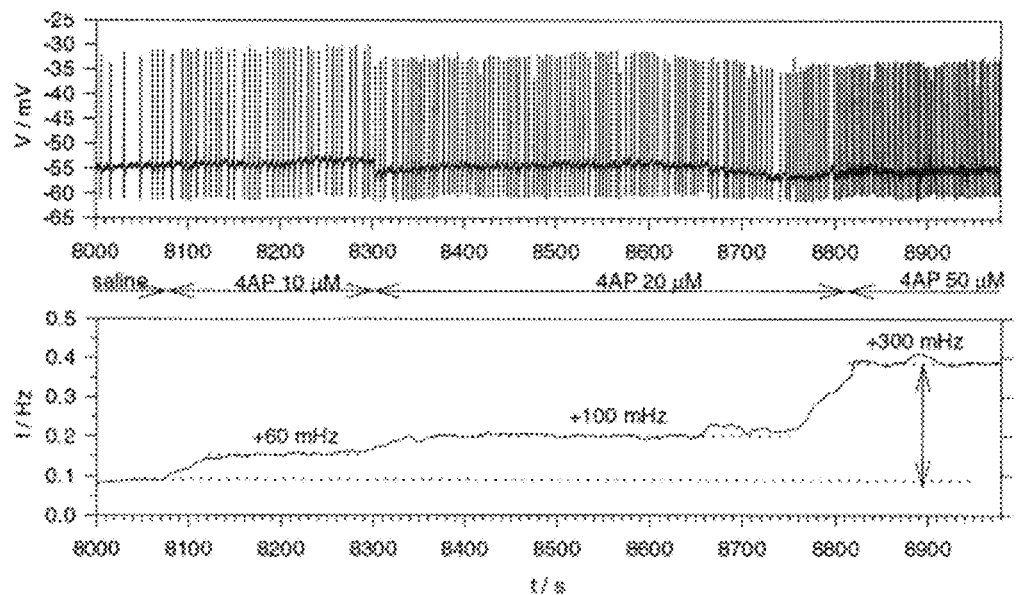
FIGS. 7A and 7B show action potentials and frequency of the spikes obtained in studies of medicinal leech (Hirudo medicinalis) ganglia.
Figure 7B:
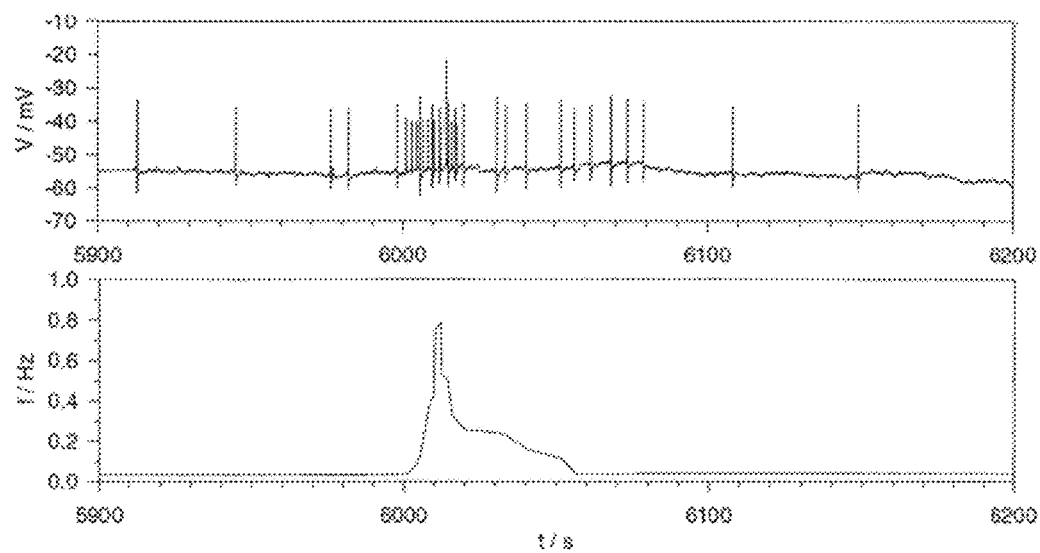
Figure 8A:
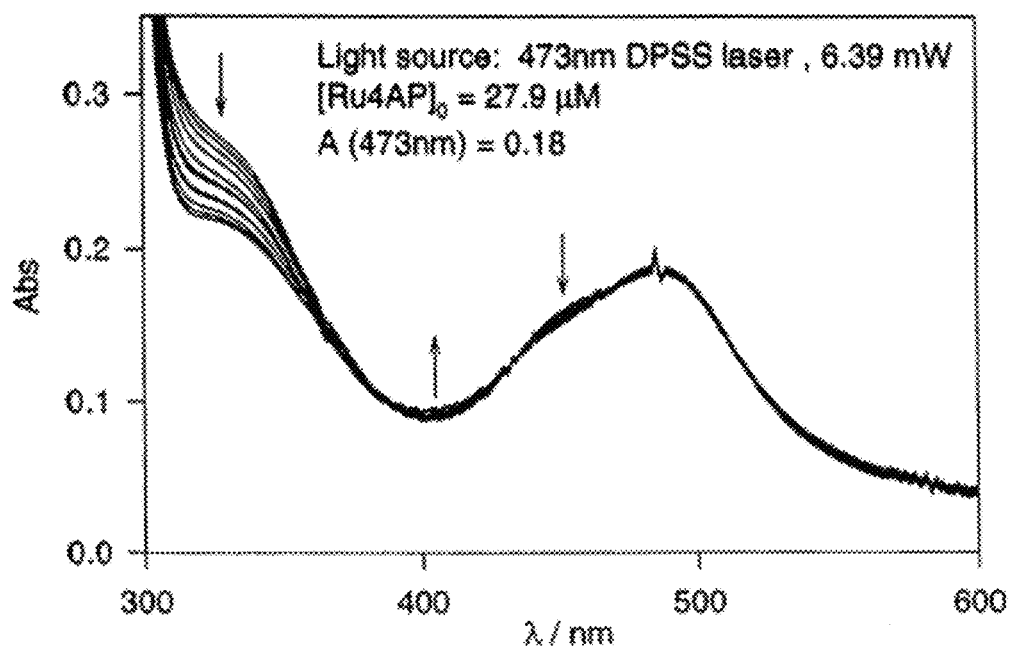
FIGS. 8A and 8B relate to spectra changes of [Ru(bpy)$_2$(4AP)$_2$]Cl$_2$ during exposure to light.
Figure 8B:
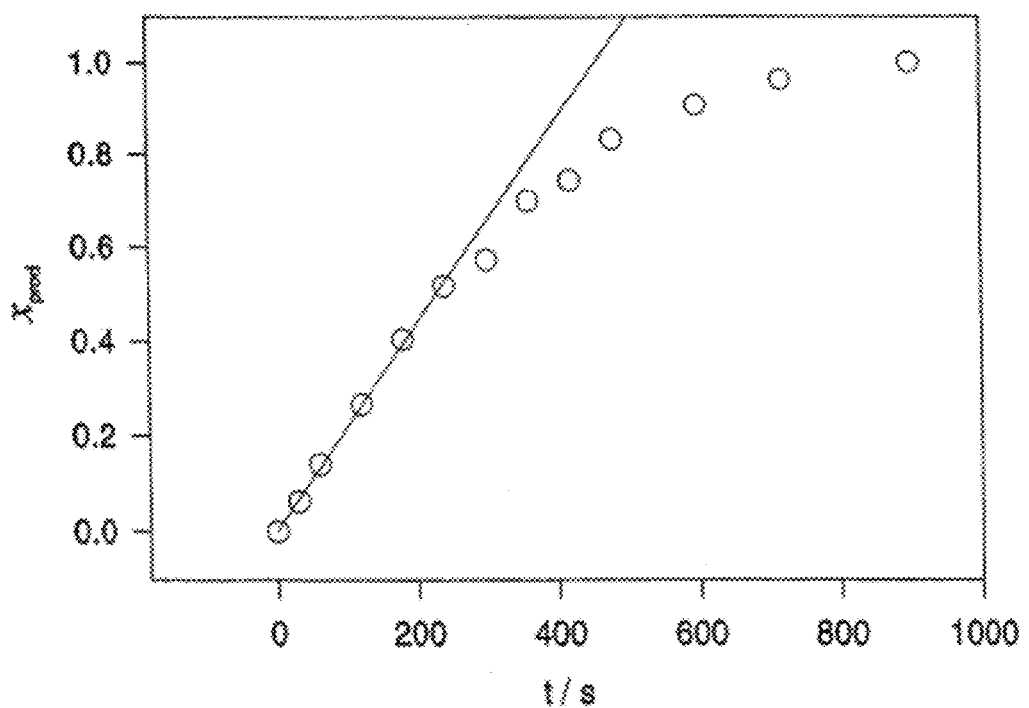
Figure 9:
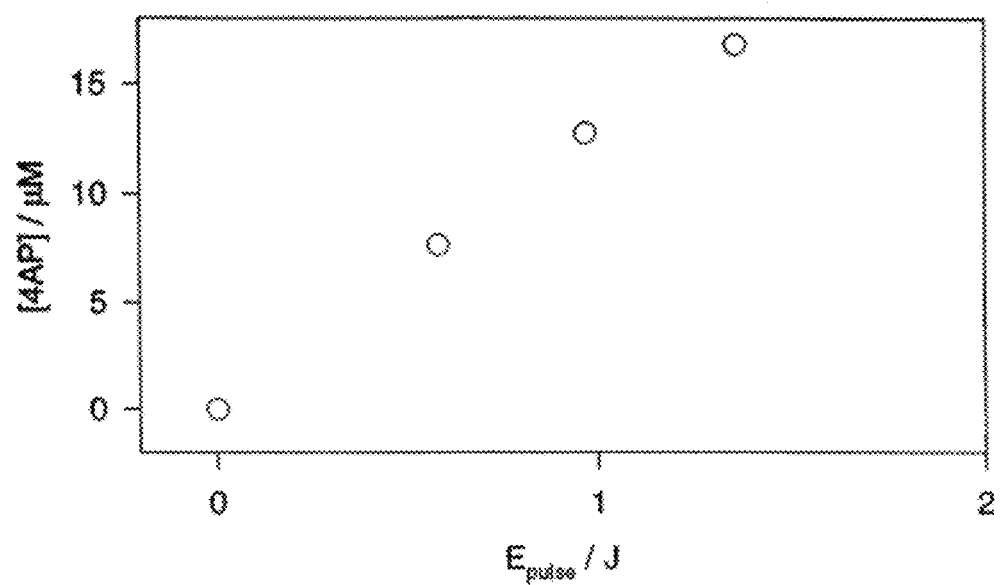
FIG. 9 shows a graph of photoreleased 4AP versus pulse energy. The light source was pulsed Xe lamp with a bandpass filter. [Ru(bpy)$_2$(4AP)$_2$]Cl$_2$=44 µM; Vol.=3 mL. The data were obtained from UV-vis spectra analysis.
Figure 10:
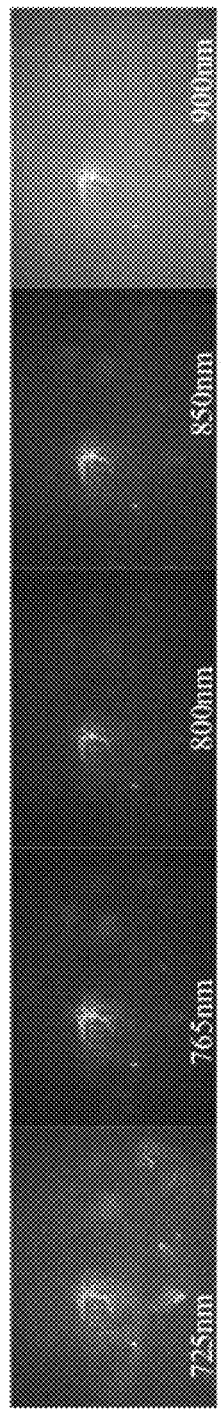
FIG. 10 shows several two-photon fluorescence images of [Ru(bpy)$_2$(TzGly)(py)]Cl$_2$ at different excitation wavelengths. (Magnification: ~20×).
Figure 13A:
FIGS. 13A and 13B.
Figure 13B:
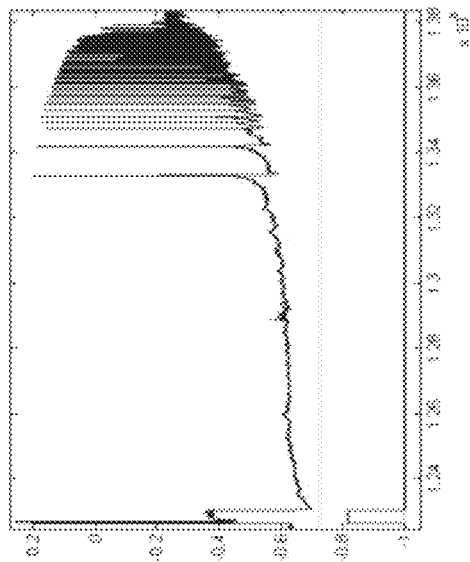
Figure 11:
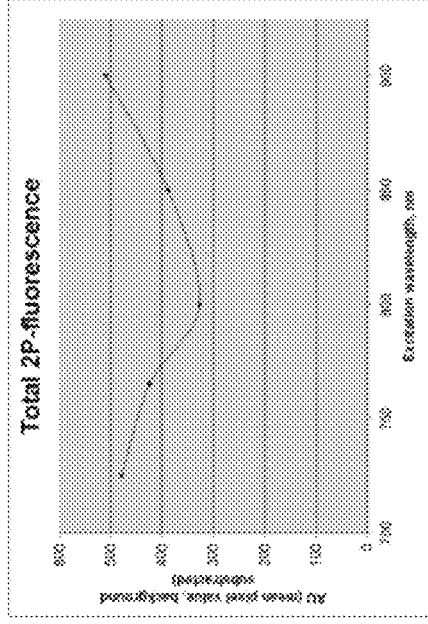
FIG. 11 depicts a graph of total two-photon fluorescence versus excitation wavelength of [Ru(bpy)$_2$(4AP)$_2$]Cl$_2$.
Figure 12:
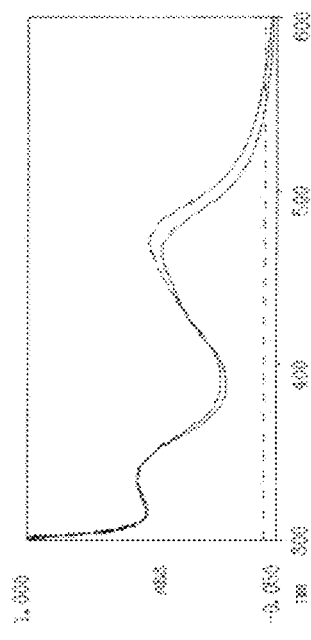
FIG. 12 presents a UV-vis spectrum of TzGly before and after irradiation with 400-600 nm light.
Figure 14A:
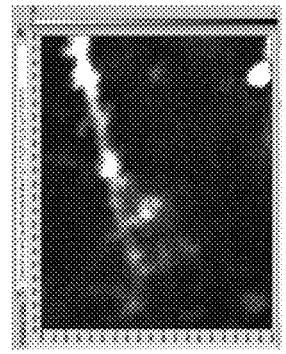
FIGS. 14A-G relate to experiments performed on neurons contacted with [Ru(bpy)$_2$(TzGly)(py)]Cl$_2$.
Figure 14B:
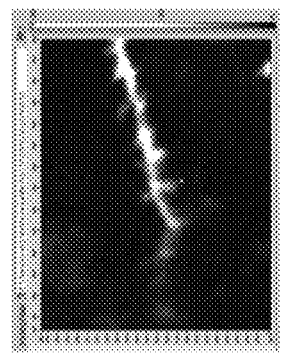
Figure 14C:
Figure 14D:
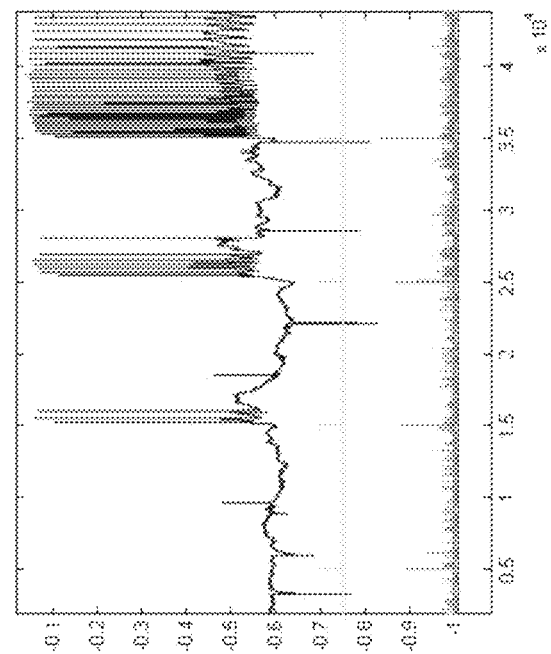
Figure 14G:
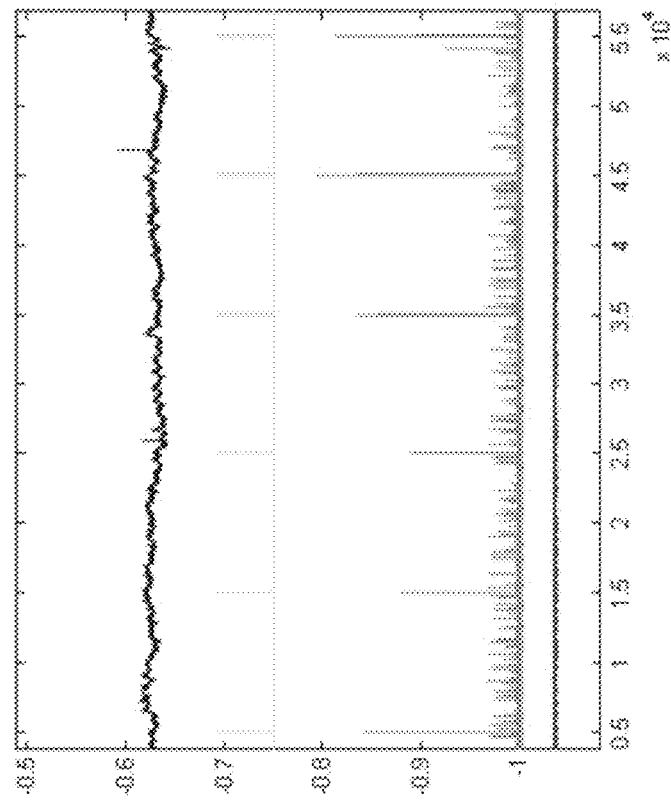
Figure 14E:
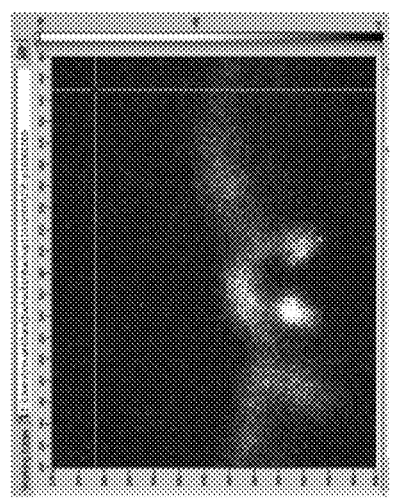
Figure 14F:
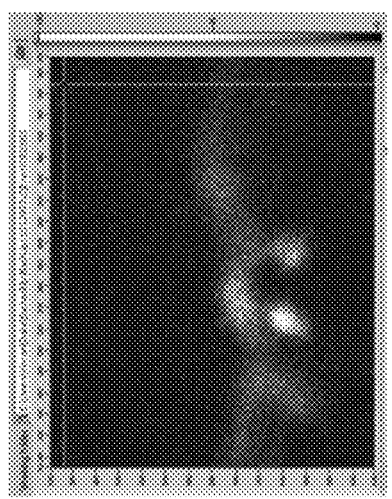

Low Ca$^{2+}$-high Mg$^{2+}$ saline solution (NaCl, 102 mM; KCl, 4 mM; CaCl$_2$: 1 mM; and MgCl$_2$: 10 mM; Tris base, pH 5.4 adjusted to 7.4) was perfused through the dish. [Ru(bpy)$_2$(4AP)$_2$]Cl$_2$ and the free ligand 4AP were injected in the mainstream at controlled times. A pulsed Xe lamp located under the dish was used to irradiate the solution. UV light was removed using a band-pass filter at 500 nm. FIG. 2 shows the behavior of the membrane potential recorded at one of the Retzius (Rz) cells in the ganglion. The upper graph in FIG. 2 shows the raw data, presenting periods of rest potential and very fast spikes (action potentials), produced by the changes in membrane ion permeabilities. The lower graph shows the instantaneous spiking frequency at each time.

After impaling the cell with an electrode, many experiments were performed on the same cell to ensure reproducibility. After 5000 seconds, the cell showed low activity, as can be seen at the left of the graph. At t=5200 s, ~100 µM $Ru(bpy)_3Cl_2$ was added to the saline solution, without significant changes in activity. 300 seconds later, at 5500 s, a light flash was directed to the ganglion. The sudden increase in the frequency of the action potentials is mainly due to the temperature pulse, but after a short time the activity decreased to the basal level. After washing by perfusion, further irradiation (t=6000 s) with a pulse showed a very similar pattern. At t=6250 s, ~100 µM $[Ru(bpy)_2(4AP)_2]Cl_2$ was added to the saline and the activity remained unchanged. However, after a new light flash (t=6400 s), sudden activity was recorded and it remained high after 300 s. A second light pulse at 6750 s promoted an even higher activity, which decreased only after cleaning perfusion with pure saline.

A similar frequency increase occurred when free 4AP was perfused onto the ganglion, thus demonstrating that the release of 4AP causes this maintained frequency increase. Calibration of the cell activity using solutions of 4AP showed that in each irradiation, 10-15 µM of 4AP were released from $[Ru(bpy)_2(4AP)_2]Cl_2$ during the previous experiments. Neither toxicity nor a deleterious effect was observed on the neuron during the experiments. These results show that a neuronal response can be stimulated using $[Ru(bpy)_2(4AP)_2]Cl_2$, an illustrative Photolabile Compound, to photorelease an organic molecule having neurophysiological activity.

Example 15

Photorelease of TzGly from $[Ru(bpy)_2(TzGly)(py)]Cl_2$

The procedure for the photorelease of TzGly from $[Ru(bpy)_2(TzGly)(py)]Cl_2$ is analogous to that used for photorelease of 4AP from $[Ru(bpy)_2(4AP)_2]Cl_2$ described above in Example 13, except that the irradiation light spot was very localized (diameter <1 micron). Irradiation of $[Ru(bpy)_2(TzGly)(py)]Cl_2$ at 470 nm photoreleased TzGly.

Example 16

Neurophysiological Activity of TzGly Photoreleased from $[Ru(bpy)_2(TzGly)(py)]Cl_2$ The neurophysiological activity of photoreleased TzGly was assessed by performing experiments similar to those as set forth above in Example 14. Accordingly, the standard setup for intracellular voltage measurements was used, and the medicinal leech *Hirudo medicinalis* was used to demonstrate photoreleased TzGly's neurophysiological activity in the leech ganglion.

Example 17

Synthesis of $[Ru(bpy)_2(PMe_3)Cl]PF_6$ 520 mg of $[Ru(bpy)_2Cl_2]$ were dissolved in 20 mL of a 1:1 mixture of methanol and water and refluxed under $N_2$. 1.2 mL of trimethylphosphine 1M in THF (Aldrich, 324108) were added with a syringe. The reaction was followed by UV-Vis spectroscopy. In some cases, more phosphine solution was added. Once the UV-Vis spectrum is stable, methanol and excess phosphine are distilled under vacuum with a rotavap. The resulting aqueous solution is filtered to remove any solids, and precipitated with excess of $KPF_6$ over ice. The dark orange solid is washed three times with cold water and dried.

Example 18

Synthesis of $[Ru(bpy)_2(PMe_3)GlutH_2](PF_6)_2$ 110 mg of $[Ru(bpy)_2(PMe_3)Cl]PF_6$ were dissolved in 2 mL of acetone. A suspension of 200 mg chloride-containing anionic exchange resin DOWEX 2×8 was added, and stirred during 10 minutes. The resulting $[Ru(bpy)_2(PMe_3)Cl]Cl$ solution was filtered. 500 mg of monosodium glutamate and 4.4 mL of NaOH 1M were added, and heated during 3 hours. 1 mL of saturated $KPF_6$ was added, and the resulting precipitate was discarded. The solution was cooled to 0° C. and acidified with HCl 5M to pH2. $[Ru(bpy)_2(PMe_3)GlutH_2](PF_6)_2$ precipitates upon addition of excess of $KPF_6$. The yellowish-orange solid is washed three times with cold water and dried.

Example 19

Figure 15:
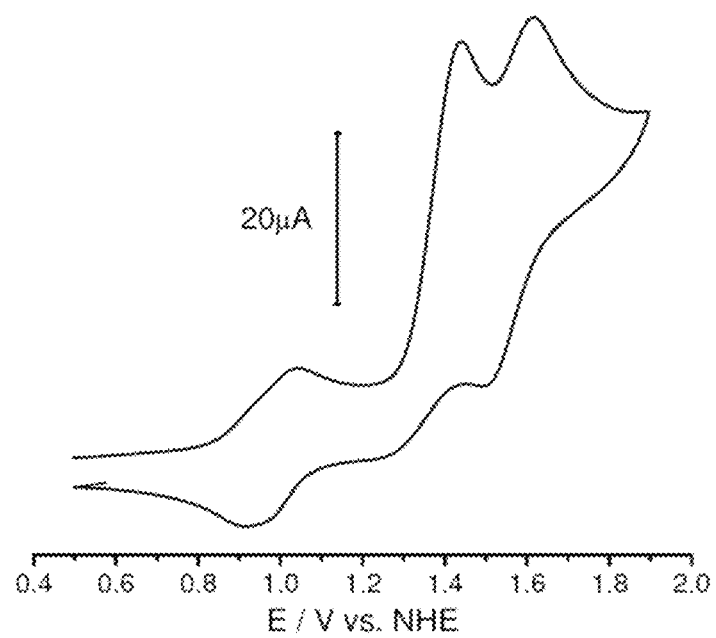
FIG. 15 depicts a cyclic voltammetry (CV) profile of native $[Ru(bpy)_2(PMe_3)Glu]$ at 100 mV/s on Pt wire electrode in $CH_3CN$ containing 100 mM $TBAPF_6$.

Photorelease of Glutamate from $[Ru(bpy)_2(PMe_3)GlutH_2](PF_6)_2$ $[Ru(bpy)_2(PMe_3)GlutH_2](PF_6)_2$ exhibits a bright orange color and presents a high solubility in water at pH>6 (as the deprotonated species $[Ru(bpy)_2(PMe3)Glu]$). Its aqueous solutions present a strong metal to ligand charge-transfer band (MLCT band) at 450 nm, characteristic of this family of Ru polypyridines. Cyclic voltammetry of the compound dissolved in acetonitrile (FIG. 15) shows three redox processes at 0.98, 1.46 and 1.56 V vs. NHE, corresponding respectively to a Ru(III)/Ru(II) couple of the original complex, and those of the complexes bearing oxidation products of glutamate.

Figure 16:
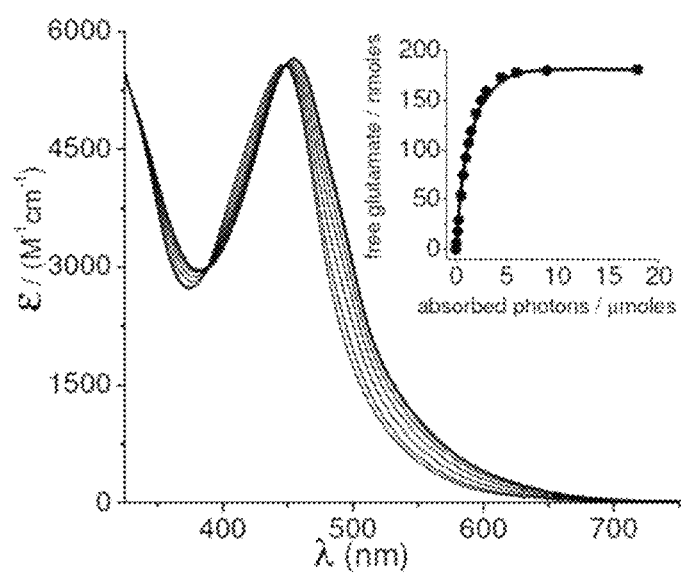
FIG. 16 shows (top) UV-Vis spectra of $[Ru(bpy)_2(PMe_3) Glu]$ 0.1 mM at pH=7 during 360 seconds irradiation using 450 nm light; (inset) amount of photoreleased glutamate derived from the experimental data (circles); fitting to the theoretical equation (line); (bottom) absorbance changes at 532 nm after flash photolysis of $[Ru(bpy)_2(PMe_3)Glu]$ 1 mM (10 ns/pulse, 256 pulses averaged).

FIG. 16 (top) shows the UV-Vis spectrum of the complex, at pH=7 during irradiation with a 450±20 nm LED. As the photoreaction proceeds, the generation of the aquo complex was recorded to reach completion in about 4 minutes. The presence of two isosbestic points as well as a factor analysis performed on the spectra indicate that just two colored species are present in the solution, according to what is expected in a single photoaquation process. The spectrum of the photoproduct was found identical to that of the complex $[Ru(bpy)_2(PMe_3)(H_2O)]_2^+$, which can be synthesized by refluxing the chloro complex in water. At pH=11 a similar behavior was observed, although in this case the product is the hydroxo complex $[Ru(bpy)_2(PMe_3)(OH)]^+$.

The inset in FIG. 16 (top) shows the yield of free glutamate generated by the photolysis obtained from the analysis of the spectra. The irradiance of the light source was calibrated using the known efficiency of the photolysis of $[Ru(bpy)(Py)_2]^{2+}$. The amount of photoreleased glutamate was fitted using a two-parameter single-exponential function: $y=a[1-\exp(-bx)]$ and the quantum yield (φPC) was obtained as a•b, adopting a value of 0.13 at pH=7 and 0.10 at pH=11.

In order to estimate the uncaging time, a flash photolysis experiment was performed on a basic aqueous solution of

[Ru(bpy)$_2$(PMe$_3$)Glu] using the second harmonic of a Nd-YAGlaser (532 nm, 10 ns pulse). The results are shown in FIG. 16 (bottom). The photocleavage occurs within the first 50 ns, being the fastest reported caged compound, to our knowledge. The fact that a tens of nanoseconds are required to complete the glutamate uncaging reaction is compatible with the observation that the excited state lifetime measured for a similar compound containing pyridine instead of glutamate is in the range of 10-100 ns.

Figure 17:
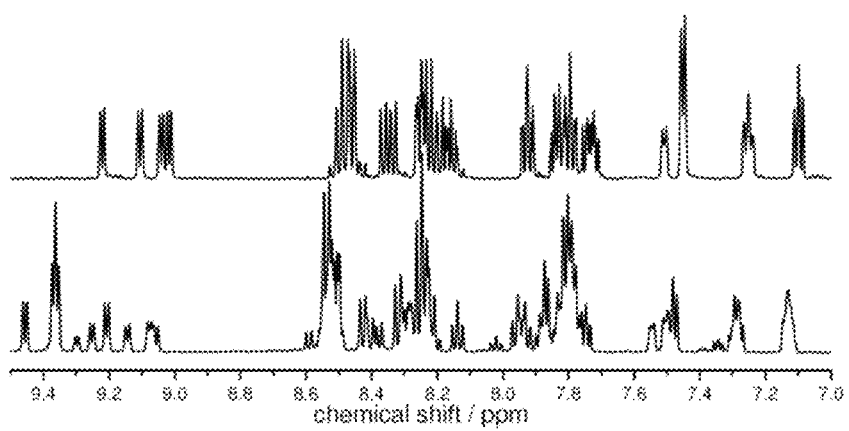
FIG. 17 shows the aromatic section of the $^1$H-NMR spectra of $[Ru(bpy)_2(PMe_3)Glu]$ in $D_2O$ before (upper trace) and after (lower trace) photolysis, showing the aromatics signals of $[Ru(bpy)_2(PMe_3)H_2O]^{2+}$.

The photoreaction was also followed by NMR spectroscopy. In the aromatic region of the 1H-NMR spectrum of the complex (FIG. 17) it is possible to distinguish 16 signals corresponding to the bpy protons, which are found duplicated because the obtained material is a roughly 1:1 mixture of diasteromeres, resulting from the coordination of L-glutamate with the racemic mixture of Λ and Δ Ru-bpy enantiomeres. No efforts were done to separate the diasteromeres and both the chemical and biological tests suggest a similar behavior.

Figure 18:
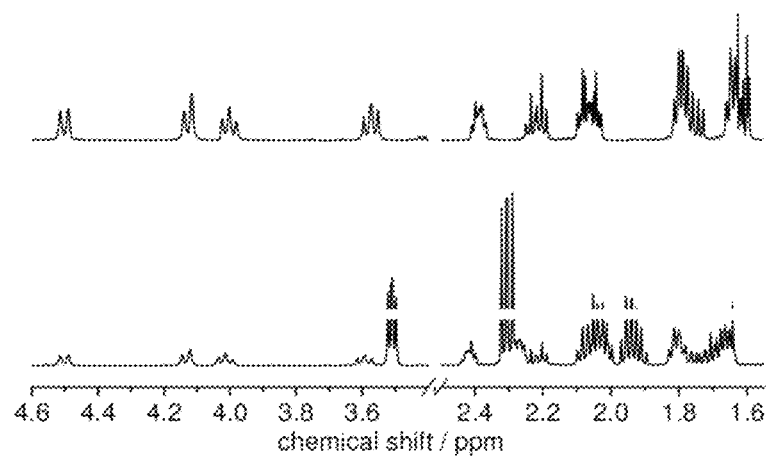
FIG. 18 shows the aliphatic section of the $^1$H-NMR spectrum of $[Ru(bpy)_2(PMe_3)Glu]$ in $D_2O$ before (upper trace) and after (lower trace) photolysis. In the last case, the signals at 3.50, 2.30, 2.04 and 1.94 ppm correspond to free glutamate.

The aliphatic region corresponding to the glutamate moiety is depicted in the upper trace of FIG. 18, where —NH$_2$ protons appear at 4.50, 4.12, 4.00 and 3.57 ppm. The presence of these signals in a D$_2$O solution, evidencing the absence of isotopic exchange in the complex, clearly indicates that the coordination of glutamate is done via the amine nitrogen, hampering further protonation. This behavior differs from that of free glutamate which, under the same conditions, exchanges rapidly D+ for H+. After 2 months in D$_2$O at room temperature, no exchange is seen, also demonstrating that the compound is indeed inert.

After photolysis, many new signals appear in the aromatic region which correspond to the aquo complexes. At the same time, the analysis of the aliphatic region (FIG. 18, bottom trace) clearly evidences the appearance of free glutamate signals. Coordinated —NH$_2$ signals diminish upon irradiation, and the characteristic signals of methylene protons of free glutamate appear at 3.50, 2.30 and 2.04 and 1.94 ppm.

Further addition of glutamate did not produce new signals, but only an intensity enhancement of the existent ones, which proves that the unique aliphatic photoproduct is glutamate.

Biocompatibility tests were performed to evaluate the potential toxicity of the complex. 350 μM [Ru(bpy)$_2$(PMe$_3$)Glu], a concentration used for two-photon uncaging experiments, was incubated with living neocortical pyramidal neurons in mouse brain slices, and carefully monitored the morphology and electrophysiological properties of the neurons using two-photon microscopy and whole-cell patch recordings. After 1 hour of incubation, no detectable effects were observed, and the neurons remained healthy. This indicates that the complex does not modify membrane integrity or has deleterious effect on living neurons.

All patent applications, published patent applications, issued and granted patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

Example 20

A Ruthenium-Rhodamine Complex as an Activatable Fluorescent Probe

This example describes a caged fluorescent probe based on a ruthenium-bipyridine core, bearing a modified rhodamine as an active derivative of a labeling molecule. This complex behaves as a caged fluorescent probe, increasing its fluorescence around 6-fold upon visible light excitation. Thus, this example demonstrates the advantages of Photolabile Compounds comprising a labeling molecule or an active derivative thereof in increasing fluorescence of fluorescent molecule or an active derivative thereof, such as, rhodamine B, rhodamine 6G, RhodB-MAPN, Rhod-6G-MAPN, RhodB-MAMePy and Rhod-6G-MAMePy.

All reagents were purchased from Sigma-Aldrich and used as received. Ru(bpy)$_2$Cl$_2$ was synthesized according to the literature using water as solvent (Viala, C.; Coudret, C. *Inorg. Chim. Acta* 2006, 359: 984-989). UV-vis spectra were taken with a HP8453 diode-array spectrometer. NMR spectra were obtained using a 500 MHz Bruker AM-500. Fluorescence emission measurements were made with a PTI Quantamaster spectrofluorometer, corrected for the instruments response function. Rhodamine B was used as fluorescence standard of emission quantum yield (φ=0.31 in aqueous solutions). Quantum yield of the complex was obtained directly from the ratio of the spectral areas, which present the same shape.

The photouncaging quantum yield measurements were performed with a Nd:YAG diode pumped solid state laser doubled to 473 nm with a constant power of 6.3 mW. The light was collimated and sent through an optical path of 1 cm into a fluorescence glass cuvette, with stirring. Total irradiation energy was measured using a Coherent Fieldmaster FM light meter with a visible light photodiode model SR45.

Microscopy of leech (*Hirudo medicinalis*) ganglia was performed in a custom-made setup for photoelectrophisiology equipped with a micromanipulator used to impale the neuron body with the ~1 μm tip diameter capillaries, and a CCD webcam as a registering device. An isolated leech ganglion from a segment between 7 and 14 was pinned down in a sylgard-coated, 35 mm Petri dish. Retzius cells were identified by their position, size, and firing behavior. Intracellular recordings were obtained with ~20 MΩ sharp capillary microelectrodes, a Neuroprobe 1600 (A-M Systems) amplifier and a A/D signal acquisition board at 1 kHz sampling rate and custom-made software. For iontophoretical injection of the dye the microelectrode was filled with recording solution to which 1 mM caged fluorescent dye (chloride form) was added. Square, biphasic pulses of 1 nA, 2 Hz were applied for less that 5 min.

Images of thin spectrophotometric flow cells and FIA capillaries were performed using a Nikon TS-100 with a fluorescence adapter. A consumer-electronics type compact digital camera (Casio Exilim EX-FC100) focusing through a normal eyepiece through a custom adapter were use to register the videos at ISO 800 sensitivity. Videos and image analysis were done using public access ImageJ software. Activation of fluorescence was performed with a 405 nm 6 mW laser diode was controlled with a pulse generator using a fast Reed relay to provide 20 ms light pulses. The laser beam was focused at the cell plane and monitored with an inverted microscope (Nikon TS100 w/fluorescence adapter).

Syntheses. Rhodamine B-Methylaminopropionitrile-amide (RhodB-MAPN). 550 mg of rhodamine B.HCl were dissolved into 10 mL of dry 1,2 dichloroethane. The system was purged with N$_2$ and 300 μL of phosphorus oxychloride were added. The mixture was refluxed during 5 h. The solvents were distilled under a vacuum and the solid was immediately dissolved in dry acetonitrile. 500 μL of triethylamine and 108 μL of N-methylaminepropionitrile were added, and the mixture was refluxed during 12 h. The solvent was removed under a vacuum, redissolved in water, filtered to eliminate any solids and precipitated by addition of excess $KPF_6$. The dark red solid was washed several times with distilled water and dried over silica gel. Exchange of Cl for $PF_6$ in order to have a water soluble ligand was performed by stirring overnight a 1:1 acetone-water solution of RhodB-MAPN.$PF_6$ with Dowex 22 anionic resin and lyophilizing the obtained solution. RhodB-MAPN chloride salt is somewhat hygroscopic and must be stored in a moisture free environment.

Overall yield: 55%. $^1$H NMR (Acetone-d6): 1H δ 1.37 (t, 12H), 2.37 (t, 2H), 3.16 (s, 3H), 3.53 (t, 2H), 3.80 (m, 8H), 6.98 (d, 2H), 7.20 (dd, 2H), 7.37 (dd, 2H), 7.62 (m, 1H), 7.77 (m, 1H), 7.82 (t, 2H).

[Ru(bpy)$_2$(L)Cl]$PF_6$. For L=Rhodamine B-Methylaminopropionitrileamide

Twenty mg of Ru(bpy)$_2$Cl$_2$ were suspended in 2 mL of a 2:1 EtOH/water mixture and the suspension was heated to 80° C. until total dissolution. The formation of the [Ru(bpy)$_2$(H$_2$O)Cl]$^+$ complex was determined by its absorption band at 490 nm (in water). After formation of the chloro-aquo complex, two equivalents of the RhodB-MAPN chloride salt were added, and the reaction was followed by TLC using silica plates and a mixture of 1:1:1 water/EtOH/nBuOH as eluent. The solution was heated at 80° C. during about 2 h, until no further TLC changes were observed. All the following procedures were done in darkness. The solution was filtered to remove any insoluble particles and the solvent was removed under a vacuum. The obtained oil was redissolved in 4 mL of a 3:1 acetone:methanol mixture and was precipitated by addition of excess THF.

The THF fraction containing unreacted ligand was discarded, and the precipitate was washed several times with THF, redissolved in water and precipitated with saturated $KPF_6$. Yield: 26%. NMR (Acetone-d6): 1H δ 1.35 (m, 12H), 2.98 (t, 2H), 3.10 (s, 3H), 3.40-3.55 (dm, 2H), 3.80 (m, 8H), 6.97 (d, 2H), 7.20-7.40 (m, 6H), 7.60 (d, 1H), 7.67 (t, 1H), 7.70-7.85 (m, 4H), 7.88-7.98 (m, 4H), 8.17 (t, 1H), 8.30 (t, 1H), 8.56 (dd, 2H), 8.69 (d, 1H), 8.72 (d, 1H), 9.55 (d, 1H), 10.08 (d, 1H).

For L=Vinylacetonitrile (VACN)

Twenty mg of Ru(bpy)$_2$Cl$_2$ were suspended in 2 mL of 96% EtOH, and the suspension was heated at 80° C. until total dissolution. The formation of the [Ru(bpy)$_2$(H$_2$O)Cl]$^+$ complex was determined by its band at 490 nm in water. 1.5 equivalents of VACN diluted in 4 mL of EtOH were added and the mixture was kept at 80° C. during 2 h. The solvent was removed by distilling under a vacuum, and the residue was redissolved in 2 mL of water, centrifuged to remove any solid, and precipitated with saturated $KPF_6$. Yield 66%.

NMR (Acetone-d6): 1H δ 3.65 (d, 2H), 5.13 (d, 2H), 5.75 (m, 1H), 7.29 (t, 1H), 7.32 (t, 1H), 7.70 (d, 1H), 7.81 (t, 1H), 7.92 (3t, 3H), 7.97 (d, 1H), 8.20 (t, 1H), 8.31 (t, 1H), 8.56 (d, 1H), 8.60 (d, 1H), 8.69 (d, 1H), 8.74 (d, 1H), 9.53 (d, 1H). 10.08 (d, 1H).

Rhodamines are useful fluorophores, due to their emission quantum yield approaching unity and their high resistance to photobleaching. They are comprised of a xanthene moiety that provides the fluorescence and a benzoic acid which modulates their spectral properties. Scheme 1A shows the structure of rhodamine B which was chosen as the starting point for this example.

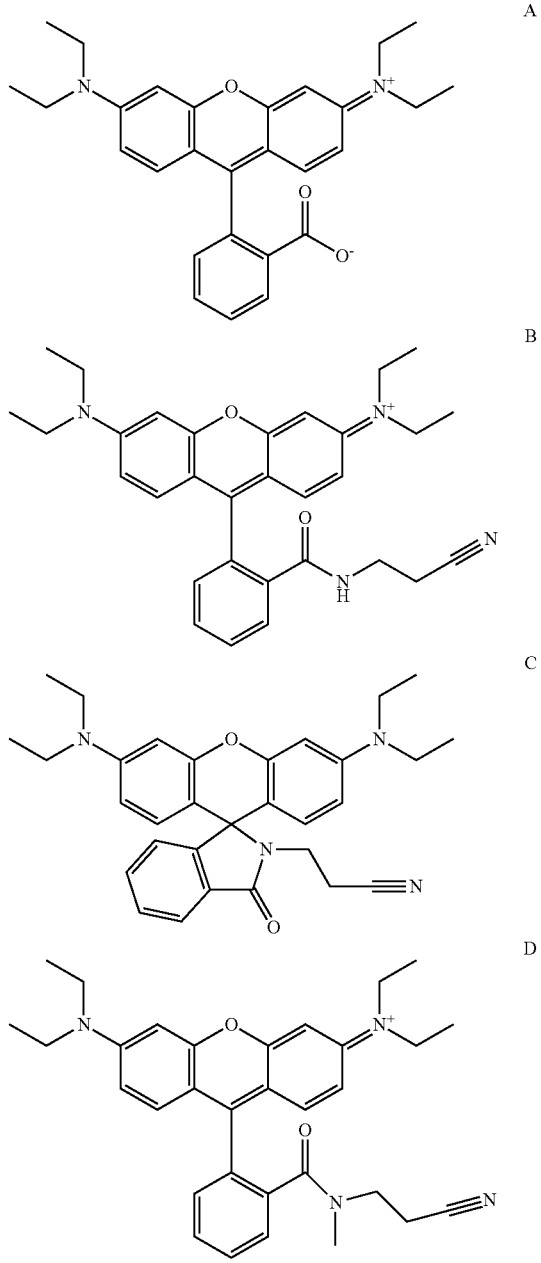

Scheme 1.

(A) Rhodamine B; (B) RhodB—APN, in its Fluorescent Form;
(C) RhodB—APN, in its Spyrolactame Nonfluorescent Form;
(D) RhodB—MAPN Ruthenium-bipyridyl complexes can easily be coordinated to donor nitrogens such as those of the aliphatic amines, pyridines, imines, and even nitriles, but not to those of anilines, not even primary ones. Diethylanilines of the rhodamine B do not form stable complexes with Ru centers and although carboxylates can be coordinated to Ru-bpy cores, such complexes are easily hydrolyzed in aqueous solutions at room temperature.

Given these properties, the chemical structure of rhodamine B was modified by adding a "sticky tail" in order to coordinate the fluorescent molecule to the metal center. In a first attempt to synthesize a modified rhodamine bearing a coordinating group, carboxylate was amidated with aminopropionitrile, using the Adamczyk procedure (Adamczyk, M. J. Bioorg. *Med. Chem. Lett.* 2000, 10: 1539-1541). The obtained compound is RhodB-APN, indicated in scheme 1B. However, although this ligand can be coordinated to Ru-bpy complexes through the nitrile, it undergoes isomerization to the cyclic spirolactame form at physiological pH (scheme 1C) becoming nonfluorescent. Rhodamine 6G can be modified similarly to the rhodamine B, described above.

A secondary amide cannot isomerize to the cyclic form, thus RhodB-MAPN, obtained through an amidation of rhodamine B acid chloride with aminopropionitrile (Scheme 1 D) presents a very high, yellow fluorescence while its terminal nitrile allows its coordination to a Ru-bpy center.

The complex cis-[Ru(bpy)$_2$(L)Cl]PF$_6$, L) RhodB-MAPN was obtained as a dark purple solid, slightly soluble in water and very soluble in acetone. Due to its very high molar absorptivity, its water solubility is high enough for most experimental situations. For the FIA imaging experiments it was used in this form. A much more soluble chloride salt, which is better for the biological experiments, was prepared by means of batch ion exchange with Dowex 22-Chloride resin in 1:1 acetone-water. The salt was used in biological experiments. The solutions of the complex present a weak yellowish fluorescence. Preliminary studies showed that the complex is light sensitive, increasing its fluorescence when irradiated in aqueous, ethanol or acetone solutions.

Figure 19:
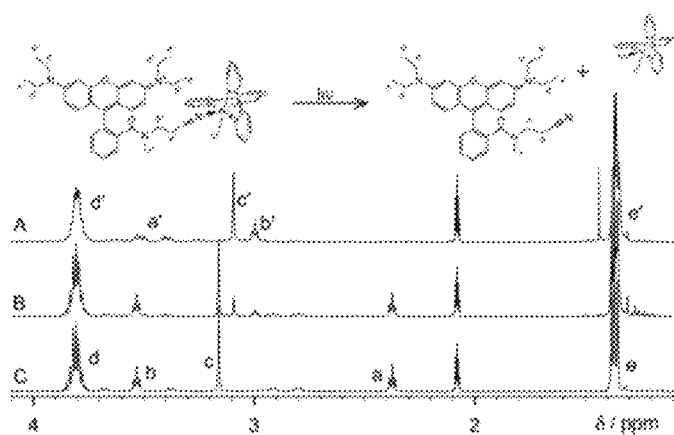
FIG. 19 shows $^1$H NMR aliphatic region spectra of the complex $[Ru(bpy)_2(RhodB-MAPN)Cl]^+$ (A) before irradiation. (B) after 5 min irradiation. (C) free RhodB-MAPN spectrum. Note in B that the signals of the free ligand a, b, and c are apparent, indicating its photorelease. The signals d and e, corresponding to the ethyl groups in RhodB-MAPN, are far from the coordination center and therefore do not suffer big changes. A photolysis reaction schematic is added for clarity.

FIG. 19 (top) shows the aliphatic region of the $^1$H NMR spectrum of the Ru complex bearing RhodB-MAPN as a ligand, showing the expected number of signals and integrations for a coordinate RhodB-MAPN. The double multiplet at 3.40-3.55 ppm (labeled a') corresponds to the methylene group closest to the coordination point. The triplet at 2.98 ppm (b') and the singlet at 3.10 ppm (c') correspond to the other methylene and the N-methyl group respectively. Similar signals were obtained if just the aminonitrile tail is coordinated to the Ru-bpy core. After 5 min of irradiation inside the NMR tube using a 450 nm LED (middle trace), new signals appear at 2.37, 3.16, and 3.53 ppm, due to the release of the RhodB-MAPN ligand. These three signals exactly match with those of the free ligand (labeled a, c, and b, respectively, bottom trace). The four ethyl groups of RhodB-MAPN are not totally equivalent, and they are seen as a multiplet (—CH$_2$—) or broad triplet (—CH$_3$) and present little change after irradiation since they are far from the coordination center.

In the aromatic region the expected number of signals and integrations for a nonsymmetric cis complex bearing RhodB-MAPN were obtained. After photolysis, the signals from the free RhodB-MAPN at 6.98, 7.20, 7.37, 7.62, 7.77, and 7.82 appear at the same chemical shifts as those from aquo-complex [Ru(bpy)$_2$(H$_2$O)Cl]$^+$.

Dilute aqueous solutions of [Ru(bpy)$_2$(RhodB-MAPN)Cl]$^+$ resent weak fluorescence with a maximum at 592 nm (excitation 518 nm).

Figure 20:
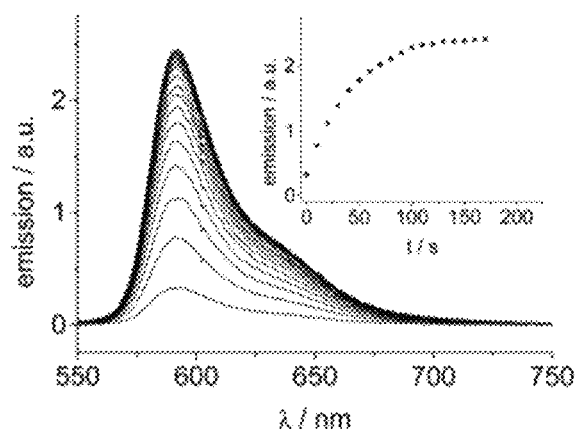
FIG. 20 shows emission spectra of a 10 μM aqueous solution of the complex $[Ru(bpy)_2(RhodB-MAPN)Cl]^+$ during irradiation of the cuvette with a 473 nm laser diode. A spectrum was measured every 10 s. Inset shows emission maxima during irradiation.

FIG. 20 depicts the emission spectra of the complex during irradiation. The maximum and the shape of the initial emission spectrum is the same as that of the free ligand RhodB-MAPN but the emission quantum yield is much lower, around pt=0.04. Quantum yields are easily calculated integrating the spectral areas. After irradiation with a 473 nm laser, RhodB-MAPN is released and the solution increases its fluorescence up to 6 fold, to ϕt=0.24. The inset shows the maxima of the spectra as a function of the irradiation time.

The quantum yield of rhodamine photorelease was calculated after the analysis of fluorescence emission data during photouncaging at 473 nm. A complete spectrum was obtained once per second. Absorption of light by the complex [Ru(bpy)$_2$(RhodB-MAPN)Cl]$^+$ yields the aquo complex [Ru(bpy)$_2$(H$_2$O)Cl]$^+$ and free RhodB-MAPN. In each irradiation period the amount of aquo complex and free RhodB-MAPN generated is given by the following:

$$\delta n = \delta t I \phi_{PU}(1-10^{-Abs_T})Abs_R/Abs_T$$

where δt is the irradiation period, I the light intensity in moles of photons per second, $\phi_{PU}$ is the quantum yield of photouncaging, $Abs_R$ is the absorbance of the photoactive species [Ru(bpy)$_2$(RhodB-MAPN)Cl]$^+$ at 473 nm and $Abs_T$ is the total absorbance of the irradiated solution. By means of finite element calculation of the former equation a photouncaging quantum yield of $\phi_{PU}$=0.12 at 25° C. was calculated. This value is in good agreement with the reported quantum yields for similar complexes.

The origin of this quenching can be attributed to the presence of the nearby ruthenium-bipyridine moiety, which presents an MLCT transition which overlaps with that of the rhodamine emission. However, direct inspection of the absorption bands of this complex at such a wavelength range is impossible, due to the very high molar extinction of the fluorescent ligand (ca., 105 M$^{-1}$ cm$^{-1}$), which obscures any absorption due to the metal center.

In order to measure this absorption, an analogous complex was synthesized using vinylacetonitrile (VACN) instead of RhodB-MAPN. It is recognized that the energy of the MLCT band of the Ru-bpy complexes are strongly dependent on the nature and basicity of the ligands near the Ru center but almost independent of the farther fragments. The complex [Ru(bpy)$_2$(VACN)Cl]$^+$ shows a typical MLCT band, which is centered around 460 nm and extends more than 100 nm to the low energy region, overlapping with the emission spectra of the rhodamine ligand. This absorption is enough to explain the observed quenching. This analog complex photoreleases VACN with even a higher quantum yield of $\phi_{PU}$=0.21.

This example provides an activatable fluorescent probe with surprising sensitivity in the visible light region. It increases its intrinsic fluorescence up to 6-fold after blue light irradiation. This probe is physiologically friendly and can be injected into living cells—even excitable ones like neurons—with no sign of acute toxicity in short-term (~2 h) experiments. The probe was used to image the laminar flow inside a thin spectrophotometric flow cell and to visualize the parabolic-shaped flow in a FIA capillary. This probe reveals not only the broadening of the plume, but also the memory effect due to accumulation of analyte near the walls, where the flow velocity approaches zero. In brief, the complex [Ru(bpy)$_2$(RhodB-MAPN)Cl]Cl is a surprisingly effective tool to image any kind of systems where manipulation of fluorescence is required.

[Ru(bpy)$_2$(Rhod6G-MAPN)Cl]Cl and [Ru(bpy)$_2$(RhodB-MAMePy)Cl] were made using the procedures described herein and exhibited results similar to those described herein for [Ru(bpy)$_2$(RhodB-MAPN)Cl]Cl, thus illustrating the applicability of the light antenna concept to the genus of Photolabile Compounds of Formulas I, II, III, V, VI, VII and VIII described herein, wherein L$^2$ comprises a labeling molecule or an active derivative thereof.

The same surprising properties demonstrated in this example for [Ru(bpy)$_2$(RhodB-MAPN)Cl]Cl are expected to apply to the Photolabile Compounds of Formulas I, II, III, V, VI, VII and VIII described herein, wherein L$^2$ comprises a labeling molecule or an active derivative thereof.

Example 21

Synthesis of [Ru(bpy)$_2$(PMe$_3$)(MTG)]$^{+2}$

A total of 67 mg of [Ru(bpy)$_2$(PMe$_3$)Cl]PF$_6$ were suspended in 4 ml acetone and 2 ml water, and were heated and stirred at 80° C. until dissolution. Evaporated acetone was gradually replaced with water or acetone to keep total volume constant but avoiding precipitation. All the following was performed under dim red light. 100 mg of D(+) methylthiogalactose were added and the mixture was kept at 80° C. for 5 hours: The reaction progress was followed by UV-Vis spectrophotometry until the aquo complex was no longer detectable. The solution was cooled in ice-cold water and saturated [BPh$_4$]$^-$ as sodium salt was added carefully. The pale yellow precipitate was washed six times in ice cold water by resuspending the precipitate and centrifugation. NMR spectra were taken in a 500 MHz Bruker Avance II spectrometer. Photolysis of the NMR sample was performed inside the unopened NMR tube, by means of a custom-built NMR photolysis device based in 10 high current (100 mA) LEDs with emission wavelength centered at 520+/−20 nm.

UV-Vis Absorption Spectrum of the Complex

Figure 21:
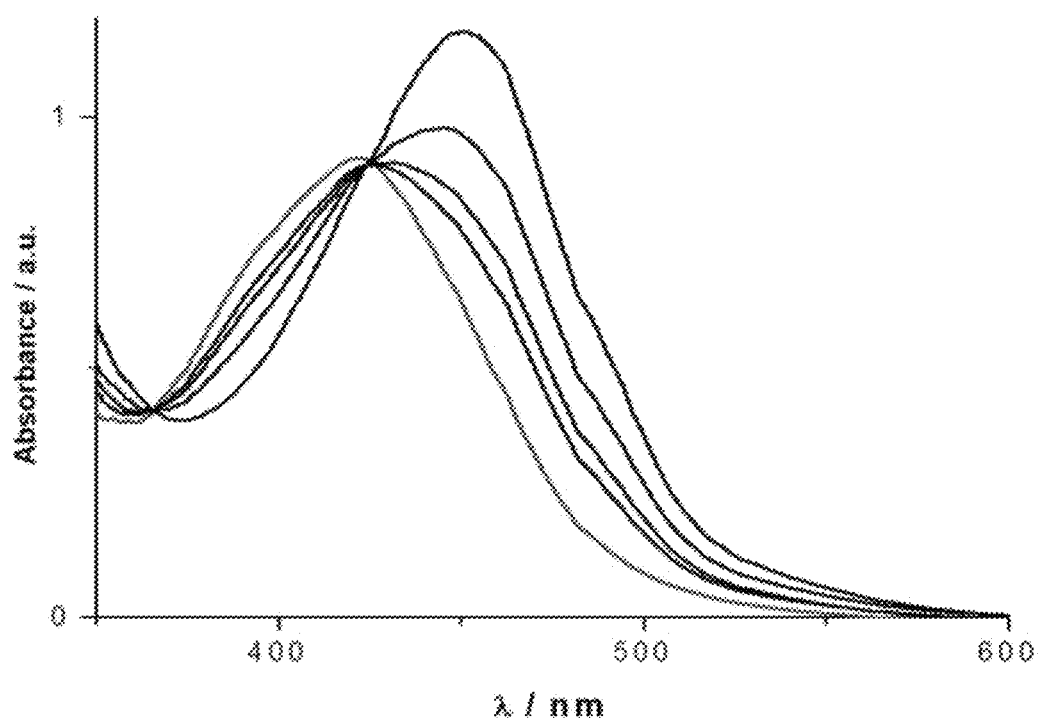
FIG. 21 shows the UV-Vis absorption spectrum of the complex $[Ru(bpy)_2(PMe_3)(MTG)]^{+2}$ as the red line. The complex has a molar absorptivity coefficient of ~3100 and a maximum absorption wavelength in the visible range at 422 nm. Photolysis quantum yield is 0.3. Successive photolysis products of the same sample are shown in black

[Ru(bpy)$_2$(PMe$_3$)(MTG)]$^{+2}$ is shown in FIG. 21 as the red line. The complex has a molar absorptivity coefficient of ~3100 and a maximum absorption wavelength in the visible range at 422 nm. Photolysis quantum yield is 0.3. Successive photolysis products of the same sample are shown in black (FIG. 21).

Figure 22:
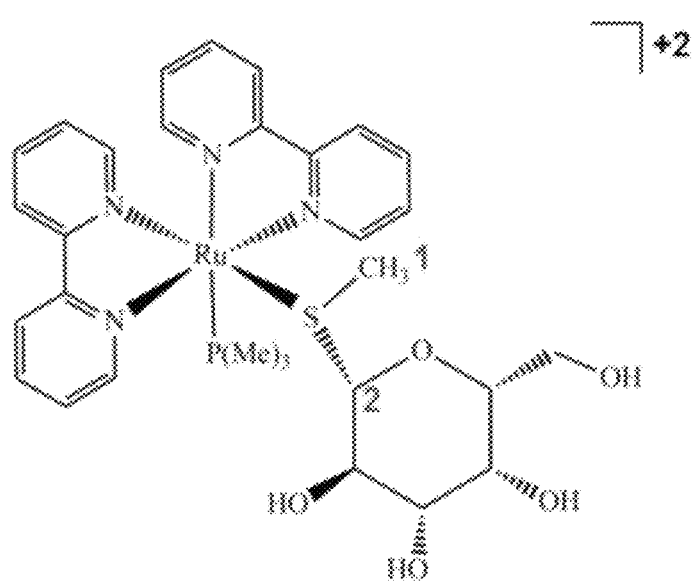
FIG. 22 shows a schematic drawing of $[(Ru(bpy)_2P (Me)_3(MTG)]^{+2}$. Protons in caged MTG numbered in red correspond to signals labeled in the NMR spectrum (as indicated in FIG. 23).
Figure 23:
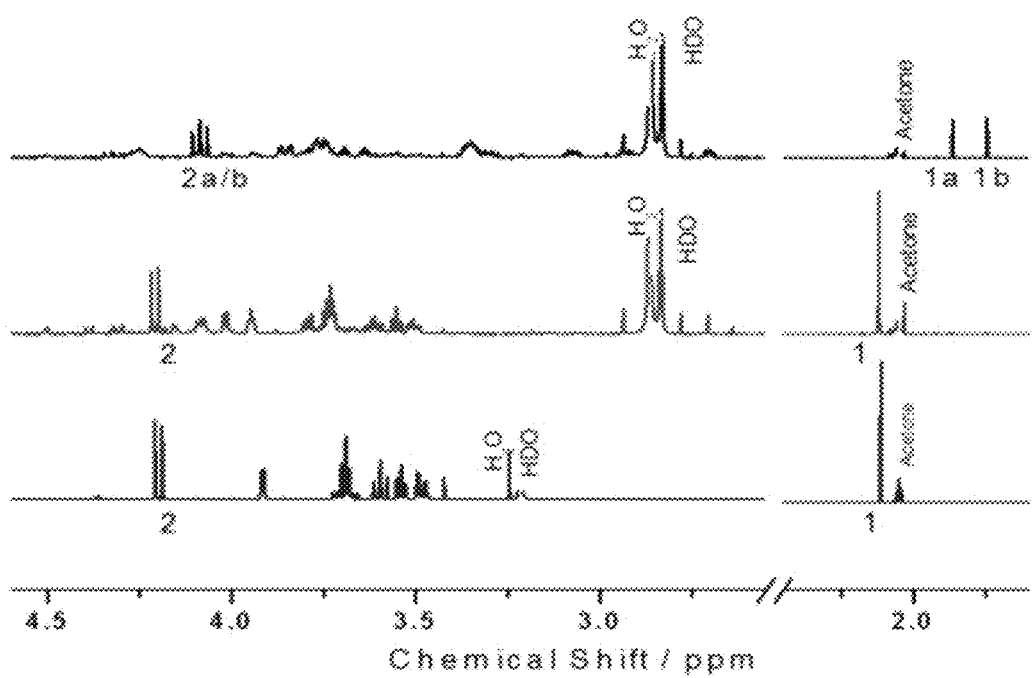
FIG. 23 shows the NMR spectrum of the complex $[Ru (bpy)_2(PMe_3)(MTG)]^{2+}$. The top trace shows the aliphatic signals of caged MTG. The middle trace corresponds to the photolysis product. The bottom trace shows free MTG.

Schematic drawing of [(Ru(bpy)$_2$P(Me)$_3$(MTG)]$^{+2}$ is shown in FIG. 22. Protons in caged MTG numbered in red correspond to signals labeled in the NMR spectrum (FIG. 23). The first (top) tracing shows the aliphatic signals of caged MTG. Middle trace corresponds to the photolysis product. Bottom trace shows free MTG. Signals below 2.5 ppm are shown multiplied by (¼). The "signature" CH$_3$ group labeled (1) in MTG, usually at 2.25 ppm in free MTG, appears as a pair of signals (Δ & Λ isomers) at 1.55 ppm and 1.48 ppm in the caged form. Also the proton labeled (2) appears as a pair of doublets at 4.07 ppm and 4.09 ppm in the complex, while in free MTG it appears as a doublet at 4.20 ppm. Solvent signals have been truncated for clarity.

Figure 24:
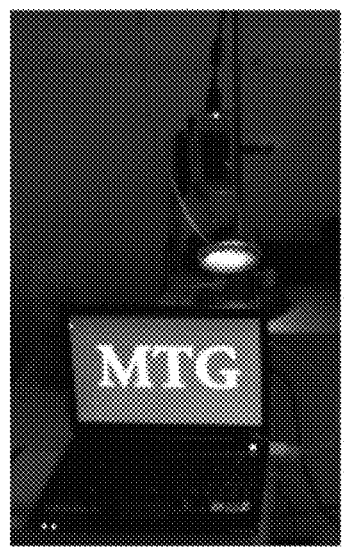
FIGS. 24A and B.
FIG. 24B shows that, after image projection, the culture is left at 37° C. until blue precipitate is noticed (~40 minutes).
Figure 24:
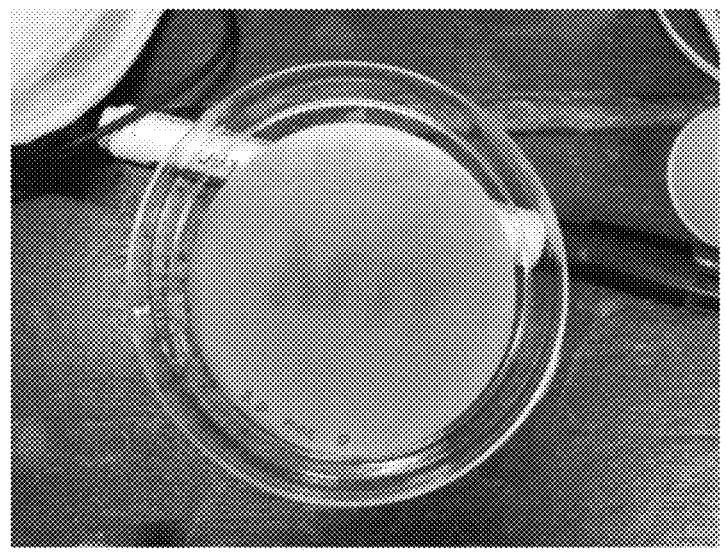

A handheld projector 3M (110 MPro) is used to irradiate for 20 minutes an *E. coli* culture growing in a piece of 7 cm diameter whatman filter paper soaked in LB medium containing 1 mM [(Ru(bpy)$_2$P(Me)$_3$(MTG)]$^{+2}$ and 0.02% X-Gal (FIG. 24A). After image projection, the culture is left at 37° C. for until blue precipitate is noticed (~40 minutes, FIG. 24B).

Example 22

Syntheses of Complexes of General Formula [Ru(Bpy)$_2$ L$^1$L$^2$]$^{+2}$

Figure 25:
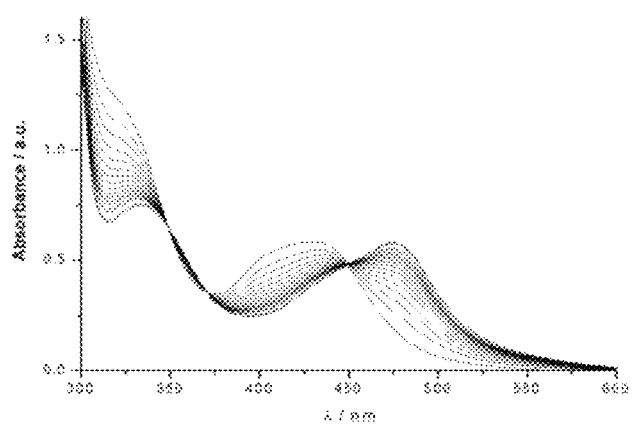
FIG. 25 shows the UV-Vis spectrum of the $[Ru(bpy)_2(4-methylpyridine)(benzonitrile)]^{2+}$ complex. The spectrum corresponding to zero photolysis is the one with the maximum absorption peak furthest to the left. Photolysis products have their maxima to the right of the original compound.

For L$^2$=4-methylpyridine; L$^1$=benzonitrile:

67 mg (130 μmoles) Ru(bpy)$_2$Cl$_2$ were suspended in 10 ml ethanol and 2 ml water, and were heated and stirred until dissolution. Under dim red light 20 μl of 4-methylpyridine (220 μmoles) were added and the mixture was refluxed for 3 hours. Volume was reduced in a rotary evaporator and the reaction product was cooled and precipitated by addition of 500 μl of 0.5 M KPF$_6$ solution in water. The precipitate was washed in cold water and dried in the dissicator overnight. This precipitate was dissolved in 5 ml of acetone and 10 ml of water, and 5 equivalents benzonitrile were added. The product was hot-precipitated by adding 1 ml 0.5 M of KPF$_6$ in water. The precipitate was filtered and washed with water and ether. $^1$H NMR (acetone-D$_6$) δ=9.91 (1H, d, (bpy)), 8.91 (1H, d, (bpy)), 8.88 (1H, d, (bpy)), 8.76 (1H, d, (bpy)), 8.75 (1H, d, (bpy)), 8.68 (1H, d, (bpy)), 8.62 (1H), 8.44 (1H, t, (bpy)), 8.36 (1H, t, (bpy)), 8.14-8.2 (3H, m), 8.09 (1H, d, (bpy)), 8.02 (1H, t, (bpy)), 7.94 (1H, t, (bpy)), 7.55-7.78 (3H, m), 7.55-7.61 (3H, m), 7.49 (1H, t, (bpy)), 7.37 (1H, d), 2.40 (3H, s, Me). The UV-vis spectrum of the [Ru(bpy)$_2$(4-methylpyridine)(benzonitrile)]$^{2+}$ complex is shown in FIG. 25. The spectrum corresponding to zero photolysis is the one with the maximum absorption peak furthest to the left. In this case, photolysis products have their maxima to the right of the original compound.

Figure 26:
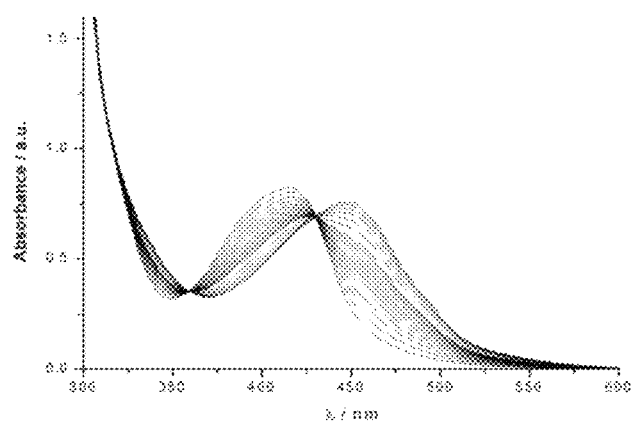
FIG. 26 shows the UV-Vis spectrum of the $[Ru(bpy)_2 (PMe_3)(3\text{-butenenitrile})]^{2+}$ complex. The spectrum corresponding to zero photolysis is the one with the maximum absorption peak furthest to the left. Photolysis products have their maxima to the right of the original compound.

For L$^2$=PMe$_3$; L$^1$=3-butenenitrile:

Starting from [Ru(bpy)$_2$(PMe$_3$)Cl]$^+$ 3 equivalents of 3-butenenitrile were added; the remaining of the reaction proceeded as for L$^2$=4-methylpyridine; L$^1$=benzonitrile. $^1$H NMR (acetone-D$_6$) δ=9.50 (1H, d, (bpy)), 9.40 (1H, d, (bpy)), 8.86 (1H, d, (bpy)), 8.83 (1H, d, (bpy)), 8.77 (1H, d, (bpy)), 8.68 (1H, d, (bpy)), 8.46-8.41 (2H, m), 8.23 (1H, t, (bpy)), 8.14 (1H, t, (bpy)), 8.07 (1H, d, (bpy)), 8.01 (1H, t, (bpy)), 7.97 (1H, t, (bpy)), 7.75 (1H, d, (bpy)), 7.58 (1H, t, (bpy)), 7.48 (1H, t, (bpy)), 5.78-5.71 (1H, m, H$_2$C=CH—), 5.14 (1H, d, J=10 Hz, H$\underline{H}_{cis}$C=CH—), 4.94 (1H, d, J=17 Hz, H$\underline{H}_{trans}$C=CH—), 3.66-3.79 (2H, m, —C$\underline{H}_2$—CN), 1.32 (9H, d, J$_{HP}$=9 Hz, PMe$_3$). The UV-vis spectrum of the [Ru(bpy)$_2$(PMe$_3$)(3-butenenitrile)]$^{2+}$ complex is shown in FIG. 26. The spectrum corresponding to zero photolysis is the one with the maximum absorption peak furthest to the left. In this case, photolysis products have their maxima to the right of the original compound.

Figure 27:
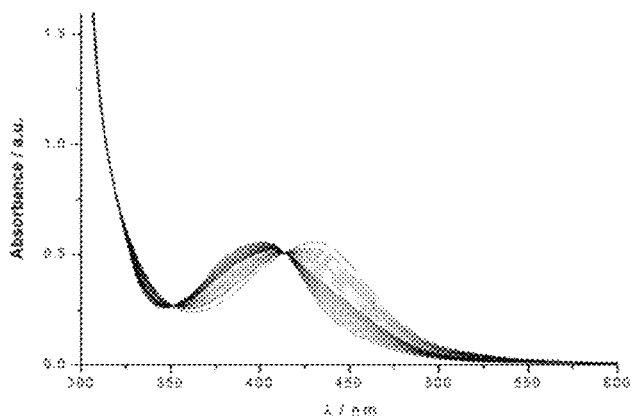
FIG. 27 shows the UV-Vis spectrum of the $[Ru(bpy)_2 (PPh_3)(3\text{-butenenitrile})]^{2+}$ complex. The spectrum corresponding to zero photolysis is the one with the maximum absorption peak furthest to the left. Photolysis products have their maxima to the right of the original compound.

For L$^2$=PPh$_3$; L$^1$=butenenitrile:

Starting from [Ru(bpy)$_2$(PPh$_3$)Cl]$^+$ 3 equivalents of 3-butenenitrile were added; the remaining of the reaction proceeded as for L$^2$=4-methylpyridine; L$^1$=benzonitrile. $^1$H NMR (acetone-D$_6$) δ=9.24 (1H, d, (bpy)), 8.92 (1H, d, (bpy)), 8.89 (1H, d, (bpy)), 8.82 (1H, d, (bpy)), 8.65 (1H, d, (bpy)), 8.63 (1H, d, (bpy)), 8.43 (1H, t, (bpy)), 8.27 (1H, t, (bpy)), 8.20 (1H, t, (bpy)), 8.10 (1H, t, (bpy)), 7.79 (1H, t, (bpy)), 7.55-7.63 (3H, m), 7.47-7.53 (4H, m), 7.29-7.39 (12H, m), 7.26 (1H, t, (bpy)), 5.63-5.73 (1H, m, H$_2$C=C$\underline{H}$—), 5.16 (1H, d, J=10.5 Hz, H$\underline{H}_{cis}$C=CH—), 4.97 (1H, d, J=17 Hz, H$\underline{H}_{trans}$C=CH—), 3.71-3.75 (2H, m, —C$\underline{H}_2$—CN). The UV-vis spectrum of the [Ru(bpy)$_2$(PPh$_3$)(3-butenenitrile)]$^{2+}$ complex is shown in FIG. 27. The spectrum corresponding to zero photolysis is the one with the maximum absorption peak furthest to the left. In this case, photolysis products have their maxima to the right of the original compound.

Figure 28:
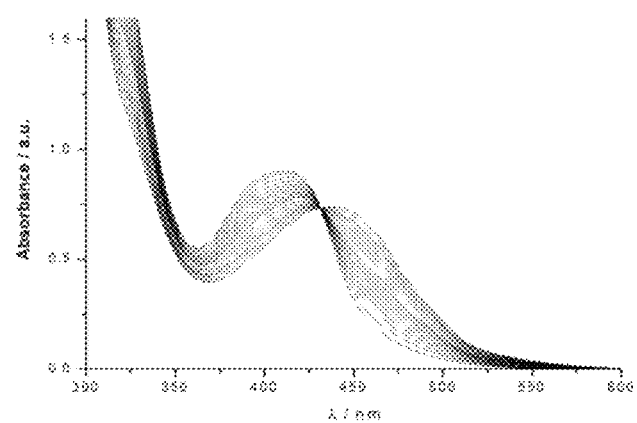
FIG. 28 shows the UV-Vis spectrum of the $[Ru(bpy)_2 (PMe_3)(2\text{-cyanophenol})]^{2+}$ complex. The spectrum corresponding to zero photolysis is the one with the maximum absorption peak furthest to the left. Photolysis products have their maxima to the right of the original compound.

For L$^2$=PMe$_3$; L$^1$=2-cyanophenol:

Starting from [Ru(bpy)$_2$(PPh$_3$)Cl]$^+$ 3 equivalents of 2-cyanophenol were added; the remaining of the reaction proceeded as for L$^2$=4-methylpyridine; L$^1$=benzonitrile. $^1$H NMR (acetone-D$_6$) δ=9.73 (1H, d, (bpy)), 9.45 (1H, d, (bpy)), 8.85 (2H, d, (bpy)), 8.76 (1H, d, (bpy)), 8.70 (1H, d, (bpy)), 8.41-8.44 (2H, m, (bpy)), 8.21 (1H, t, (bpy)), 8.16 (1H, t, (bpy)), 8.12 (1H, d, (bpy)), 8.00 (1H, t, (bpy)), 7.96 (1H, t, (bpy)), 7.78 (1H, d, (bpy)), 7.58 (1H, t), 7.47-7.54 (1H, m), 7.44 (1H, t), 7.38 (1H, d), 6.97 (1H, d), 6.77 (1H, t), 1.37 (9H, d, J$_{HP}$=9 Hz, PMe$_3$). The UV-vis spectrum of the [Ru(bpy)$_2$(PMe$_3$)(2-cyanophenol)]$^{2+}$ complex is shown in FIG. 28. The spectrum corresponding to zero photolysis is the one with the maximum absorption peak furthest to the left. In this case, photolysis products have their maxima to the right of the original compound.

Figure 29:
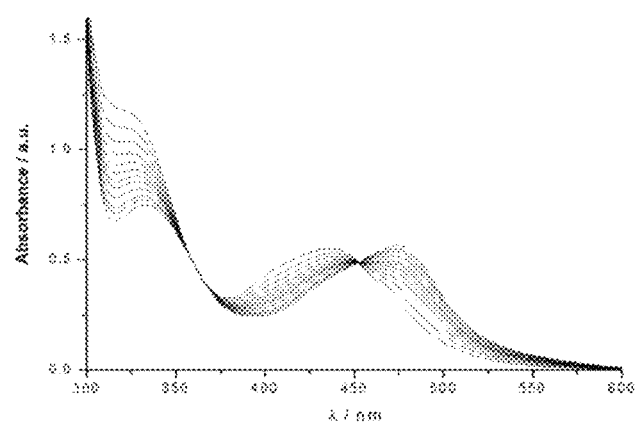
FIG. 29 shows the UV-Vis spectrum of the $[Ru(bpy)_2(4\text{-methylpyridine})(2\text{-cyanophenol})]^{2+}$ complex. The spectrum corresponding to zero photolysis is the one with the maximum absorption peak furthest to the left. Photolysis products have their maxima to the right of the original compound.

Analogously to the above procedures, the following complexes were also synthesized:

The UV-vis spectrum of the [Ru(bpy)$_2$(4-methylpyridine)(2-cyanophenol)]$^{2+}$ complex is shown in FIG. 29. The spectrum corresponding to zero photolysis is the one with the maximum absorption peak furthest to the left. In this case, photolysis products have their maxima to the right of the original compound.

Figure 30:
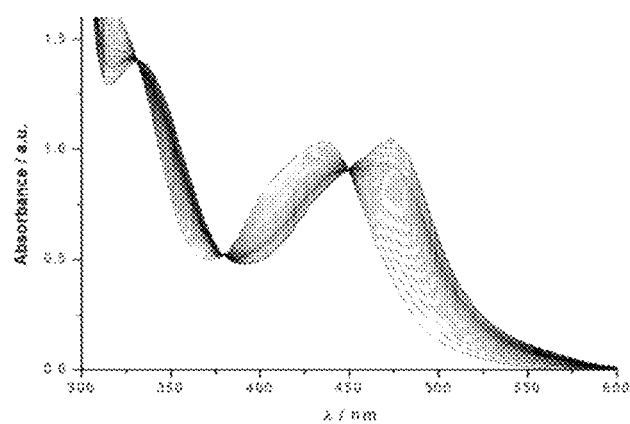
FIG. 30 shows the UV-Vis spectrum of the $[Ru(bpy)_2(4\text{-methylpyridine})(3\text{-butenenitrile})]^{2+}$ complex. The spectrum corresponding to zero photolysis is the one with the maximum absorption peak furthest to the left. Photolysis products have their maxima to the right of the original compound.

The UV-vis spectrum of the [Ru(bpy)$_2$(4-methylpyridine)(3-butenenitrile)]$^{2+}$ complex is shown in FIG. 30. The spectrum corresponding to zero photolysis is the one with the maximum absorption peak furthest to the left. In this case, photolysis products have their maxima to the right of the original compound.

Figure 31:
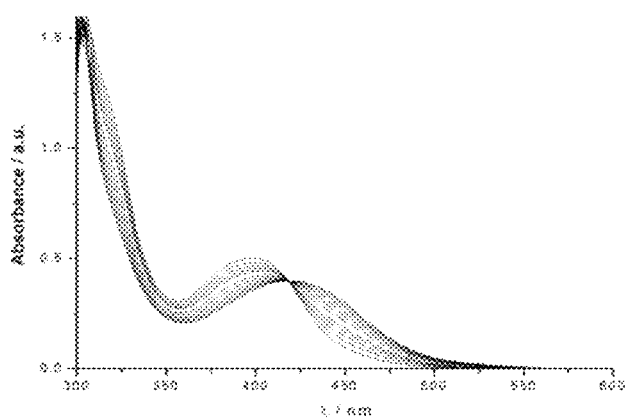
FIG. 31 shows the UV-Vis spectrum of the $[Ru(bpy)_2 (PPh_3)(2\text{-cyanophenol})]^{2+}$ complex. The spectrum corresponding to zero photolysis is the one with the maximum absorption peak furthest to the left. Photolysis products have their maxima to the right of the original compound.

The UV-vis spectrum of the [Ru(bpy)$_2$(PPh$_3$)(2-cyanophenol)]$^{2+}$ complex is shown in FIG. 31. The spectrum corresponding to zero photolysis is the one with the maximum absorption peak furthest to the left. In this case, photolysis products have their maxima to the right of the original compound.

It will be noted that, photolysis products to the right of the reactives is not a general rule. In some cases, photolysis absorption spectra may lie to the left of the reactant spectrum.

We claim:

1. A compound of Formula V:

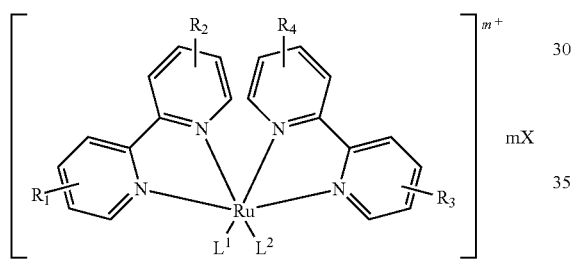

wherein:

each $L^1$ is independently an organic molecule having:
(a) a 5-membered monocyclic aromatic ring, one of the ring's members being a nitrogen atom that forms a bond with Ru;
(b) a 6-membered monocyclic aromatic ring, one of the ring's members being a nitrogen atom that forms a bond with Ru;
(c) an 8-10-membered bicyclic ring, one of the bicyclic rings being aromatic and having a nitrogen atom member that forms a bond with Ru;
(d) an —NH$_2$ group whose nitrogen atom forms a bond with Ru;
(e) a —COOH group, one of whose oxygen atoms forms a bond with Ru;
(f) a —PR$_2$ group whose phosphorus atom forms a bond with Ru, wherein R is independently —H, —C$_1$-C$_{18}$ alkyl, or aryl;
(g) an —SR group whose sulfur atom forms a bond with Ru, wherein R is independently —H, —C$_1$-C$_{18}$ alkyl, or aryl; or
(h) a —CN group whose nitrogen atom forms a bond with Ru;

$L^2$ is (R$^9$)$_3$P, or (R$^9$O)$_3$P and m is 2; or $L^2$ is a labeling molecule or an active derivative thereof connected to Ru through the phosphorous atom of (R$^9$)$_2$P or (R$^9$O)$_2$P and m is 2; or $L^2$ is a labeling molecule or an active derivative thereof connected to Ru through the nitrogen atom of: NHR$^9$, N(R$^9$)$_2$, pyridyl, C(R$^9$)=NH, C(R$^9$)=NR$^9$, cyclic aliphatic amine group or nitrile and m is 2;

wherein each R$^9$ is independently —C$_1$-C$_{18}$ alkyl, —C$_3$-C$_8$ cycloalkyl, or phenyl;

wherein when $L^2$ is P(phenyl)$_3$ or a labeling molecule or an active derivative thereof connected to Ru through the phosphorous atom of P(phenyl)$_2$, each phenyl is independently substituted with —C$_1$-C$_{18}$ alkyl, —(C$_1$-C$_{18}$ alkyl)-OH, aryl, —(C$_1$-C$_{18}$ alkyl)-oxy, —(C$_1$-C$_{18}$ alkyl)-amino, —(C$_1$-C$_{18}$ alkyl)-thio, —CO$_2$Y, —C(=O)Y, —C(=O)NY$_2$, —NH$_2$, —NO$_2$, —OH, or —SH, and R$^1$ to R$^4$ are independently —H, —C$_1$-C$_{18}$ alkyl; —NH$_2$, —(C$_1$-C$_{18}$ alkyl)-O—(C$_1$-C$_{18}$ alkyl), —OC(O)(C$_1$-C$_{18}$ alkyl), —(C$_1$-C$_{18}$ alkyl)-OH, aryl, —(C$_1$-C$_{18}$ alkyl)-oxy, —(C$_1$-C$_{18}$ alkyl)-amino, —(C$_1$-C$_{18}$ alkyl)-thio, —CO$_2$Y, —C(=O)Y, —C(=O)NY$_2$, —NO$_2$, or —SH, or R$^1$ and R$^2$ and/or R$^3$ and R$^4$ can combine to form a carbocyclic ring substituted by one or more oxo groups;

wherein when $L^2$ is not P(phenyl)$_3$, R$^1$ to R$^4$ are independently —H, —(C$_1$-C$_{18}$ alkyl)-OH, aryl, —(C$_1$-C$_{18}$ alkyl)-oxy, —(C$_1$-C$_{18}$ alkyl)-amino, —(C$_1$-C$_{18}$ alkyl)-thio, —CO$_2$Y, —C(=O)Y, —C(=O)NY$_2$, —NO$_2$, —OH, or —SH, or R$^1$ and R$^2$ and/or R$^3$ and R$^4$ can combine to form a carbocyclic ring substituted by one or more oxo groups, wherein at least one of R$^1$ to R$^4$ is not H;

X is Cl$^-$, F$^-$, Br$^-$, I$^-$, PF$_6^-$, CF$_3$SO$_3^-$, (C$_1$-C$_{18}$ alkyl)-CO$_2^-$, or (C$_1$-C$_{18}$ alkyl)-SO$_3^-$; and Y is selected from the group consisting of —H, —C$_1$-C$_{18}$ alkyl, aryl, —(C$_1$-C$_{18}$ alkyl)-aryl, —C$_3$-C$_8$ cycloalkyl, heteroaryl, and heterocyclyl.

2. The compound of claim 1, wherein the organic molecule is 4-aminopyridine.

3. The compound of claim 1, wherein the organic molecule is (RS)-(tetrazol-5-yl) glycine.

4. The compound of claim 1, wherein the organic molecule is (tetrazol-5-yl) AMPA.

5. The compound of claim 1, wherein the organic molecule is nicotine or caffeine.

6. The compound of claim 1, wherein the organic molecule is serotonin, epinephrine, norepinephrine, or dopamine.

7. The compound of claim 1, wherein the organic molecule is adenosine 5'-diphosphate ADP, adenosine 5'-triphosphate ATP, adenosine 5'-monophosphate AMP, cyclic adenosine 5'-diphosphate ribose, or adenosine 3',5'-cyclic monophosphate.

8. The compound of claim 1, wherein the organic molecule is aminobutyric acid or L-glutamic acid, or methyl-D-aspartic acid.

9. The compound of claim 1, wherein the organic molecule is methyl beta-D-1-thiogalactopyranoside.

10. The compound of claim 1, wherein the organic molecule is isopropyl beta-D-1-thiogalactopyranoside.

11. The compound of claim 1, wherein the organic molecule is mercaptopurine, thioguanine, doxorubicin, cytarabin, temozolomide or gentamicin.

12. The compound of claim 1, wherein the organic molecule is mercaptopurine.

13. The compound of claim 1, wherein the organic molecule is thioguanine.

14. The compound of claim 1, wherein the organic molecule is doxorubicin.

15. The compound of claim 1, wherein the organic molecule is cytarabin.

16. The compound of claim 1, wherein the organic molecule is temozolomide.

17. The compound of claim 1, wherein the organic molecule is gentamicin.

18. The compound of claim 1, wherein the organic molecule is benzonitrile, 3-butenenitrile or 2-cyanophenol.

19. A method for releasing an organic molecule from a Photolabile Compound, comprising:
exposing a compound of claim 1 to light under conditions sufficient to release the organic molecule.

20. The method of claim 19, wherein the light comprises a wavelength of about 300 to about 500 nm.

21. The method of claim 19, wherein the light comprises a wavelength of about 300 to about 360 nm.

22. The method of claim 19, wherein the light comprises a wavelength of about 450 to about 500 nm.

23. The method of claim 19, wherein the light comprises visible light or infrared light.

24. The method of claim 19, wherein the exposing occurs at a temperature from about 0° C. to about 150° C.

25. A method for making an organic molecule bioavailable to a subject, comprising:
(a) administering a compound of claim 1 to the subject; and
(b) exposing the compound to light under conditions sufficient to release the organic molecule from the compound, wherein the organic molecule has:
   a 5-membered monocyclic aromatic ring, one of the ring's members being a nitrogen atom that forms a bond with Ru;
   (ii) a 6-membered monocyclic aromatic ring, one of the ring's members being a nitrogen atom that forms a bond with Ru;
   (iii) an 8-10-membered bicyclic ring, one of the bicyclic rings being aromatic and having a nitrogen atom member that forms a bond with Ru;
   (iv) an —NH$_2$ group whose nitrogen atom forms a bond with Ru;
   (v) a —COOH group, one of whose oxygen atoms forms a bond with Ru;
   (vi) a —PR$_2$ group whose phosphorus atom forms a bond with Ru, wherein R is independently —H, —C$_1$-C$_{18}$ alkyl, or aryl;
   (vii) an —SR group whose sulfur atom forms a bond with Ru, wherein R is independently —H, —C$_1$-C$_{18}$ alkyl, or aryl; or
   (viii) a —CN group whose nitrogen atom forms a bond with Ru.

26. The method of claim 25, wherein the organic molecule has:
a 5-membered monocyclic aromatic ring, one of the ring's members being a nitrogen atom that forms a bond with Ru;
(ii) a 6-membered monocyclic aromatic ring, one of the ring's members being a nitrogen atom that forms a bond with Ru;
(iii) an 8-10-membered bicyclic ring, one of the bicyclic rings being aromatic and having a nitrogen atom member that forms a bond with Ru;
(iv) an —NH$_2$ group whose nitrogen atom forms a bond with Ru;
(v) a —COOH group, one of whose oxygen atoms forms a bond with Ru;

(vi) a —PR$_2$ group whose phosphorus atom forms a bond with Ru, wherein R is independently —H, —C$_1$-C$_{18}$ alkyl, or aryl; or
(vii) an —SR group whose sulfur atom forms a bond with Ru, wherein R is independently —H, —C$_1$-C$_{18}$ alkyl, or aryl.

27. The method of claim 25, wherein the light is sunlight, photo-optic light, or laser light.

28. The method of claim 25, wherein the light is visible light or infrared light.

29. The method of claim 25, wherein the exposing occurs at the site of a tumor, cancer, or neoplasm.

30. The method of claim 25, wherein the exposing occurs at the site of a blood dyscrasia.

31. The method of claim 25, wherein the administering occurs intravenously, topically, intradermally, intramuscularly, transdermally, subcutaneously, intranasally, parenterally, intrathecally, vaginally, rectally, colorectally, orally, intracranially, retroorbitally, intrasternally, or by injection.

32. The method of claim 25, wherein the administering is via a transdermal patch.

33. A composition comprising a compound of claim 1 and a physiologically acceptable carrier, vehicle, diluent, or excipient.

34. A vessel containing a compound of claim 1.

35. The vessel of claim 34, further containing a biological sample.

36. The vessel of claim 35, wherein the biological sample is an organ, tissue, cell, or hair sample.

37. The vessel of claim 36, wherein the tissue is neuronal tissue.

38. The vessel of claim 36, wherein the cell is a neuronal cell.

39. The vessel of claim 36, wherein the tissue or cell is a tumor, cancer, or neoplastic tissue or cell.

40. The vessel of claim 35, wherein the biological sample is a body fluid sample.

41. The vessel of claim 40, wherein the body fluid sample is blood, serum, plasma, lymph, saliva, sputum, tears, semen, or urine.

42. A kit comprising a compound of claim 1 and instructions for use of the compound.

43. A method for enhancing the solubility of an organic molecule, comprising
complexing an organic molecule to a photolabile caging group to form a compound of claim 1;
wherein exposing the compound to light under sufficient conditions releases the organic molecule from the compound, and wherein the organic molecule has:
(i) a 5-membered monocyclic aromatic ring, one of the ring's members being a nitrogen atom that forms a bond with Ru;
(ii) a 6-membered monocyclic aromatic ring, one of the ring's members being a nitrogen atom that forms a bond with Ru;
(iii) an 8-10-membered bicyclic ring, one of the bicyclic rings being aromatic and having a nitrogen atom member that forms a bond with Ru;
(iv) an —NH$_2$ group whose nitrogen atom forms a bond with Ru;
(v) a —COOH group, one of whose oxygen atoms forms a bond with Ru;
(vi) a —PR$_2$ group whose phosphorus atoms forms a bond with Ru, wherein R is independently —H, —C$_1$-C$_{18}$ alkyl, or aryl;

(vii) an —SR group whose sulfur atom forms a bond with Ru, wherein R is independently —H, —$C_1$-$C_{18}$ alkyl, or aryl; or
(viii) a —CN group whose nitrogen atom forms a bond with Ru.

44. The method of claim 43, wherein the organic molecule has:
(i) a 5-membered monocyclic aromatic ring, one of the ring's members being a nitrogen atom that forms a bond with Ru;
(ii) a 6-membered monocyclic aromatic ring, one of the ring's members being a nitrogen atom that forms a bond with Ru;
(iii) an 8-10-membered bicyclic ring, one of the bicyclic rings being aromatic and having a nitrogen atom member that forms a bond with Ru;
(iv) an —$NH_2$ group whose nitrogen atom forms a bond with Ru;
(v) a —COOH group, one of whose oxygen atoms forms a bond with Ru;
(vi) a —$PR_2$ group whose phosphorus atom forms a bond with Ru, wherein R is independently —H, —$C_1$-$C_{18}$ alkyl, or aryl; or
(vii) an —SR group whose sulfur atom forms a bond with Ru, wherein R is independently —H, —$C_1$-$C_{18}$ alkyl, or aryl.

45. A compound of Formula VI:

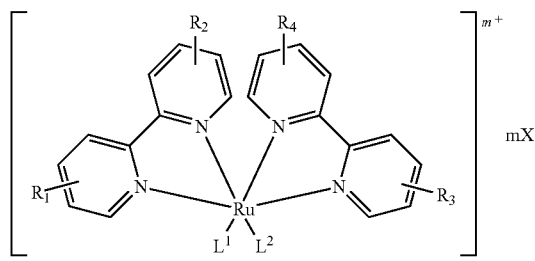

wherein:
each $L^1$ is independently an organic molecule having:
(a) a 5-membered monocyclic aromatic ring, one of the ring's members being a nitrogen atom that forms a bond with Ru;
(b) a 6-membered monocyclic aromatic ring, one of the ring's members being a nitrogen atom that forms a bond with Ru;
(c) an 8-10-membered bicyclic ring, one of the bicyclic rings being aromatic and having a nitrogen atom member that forms a bond with Ru;
(d) an —$NH_2$ group whose nitrogen atom forms a bond with Ru;
(e) a —COOH group, one of whose oxygen atoms forms a bond with Ru;
(f) a —$PR_2$ group whose phosphorus atom forms a bond with Ru, wherein R is independently —H, —$C_1$-$C_{18}$ alkyl, or aryl;
(g) an —SR group whose sulfur atom forms a bond with Ru, wherein R is independently —H, —$C_1$-$C_{18}$ alkyl, or aryl; or
(h) a —CN group whose nitrogen atom forms a bond with Ru;
$L^2$ is P(phenyl)$_3$, wherein each phenyl is independently substituted with —$C_1$-$C_{18}$ alkyl, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NH_2$, —$NO_2$, —OH, or —SH; or $L^2$ is a labeling molecule or an active derivative thereof connected to Ru through the phosphorous atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$, cyclic aliphatic amine group or nitrile and m is 2;
wherein each $R^9$ is independently —$C_1$-$C_{18}$ alkyl, —$C_3$-$C_8$ cycloalkyl, or phenyl;
$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;
X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and
Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

46. The compound of claim 45, wherein each $L^1$ is independently an organic molecule having:
(a) a 5-membered monocyclic aromatic ring, one of the ring's members being a nitrogen atom that forms a bond with Ru;
(b) a 6-membered monocyclic aromatic ring, one of the ring's members being a nitrogen atom that forms a bond with Ru;
(c) an 8-10-membered bicyclic ring, one of the bicyclic rings being aromatic and having a nitrogen atom member that forms a bond with Ru;
(d) an —$NH_2$ group whose nitrogen atom forms a bond with Ru;
(e) a —COOH group, one of whose oxygen atoms forms a bond with Ru;
(f) a —$PR_2$ group whose phosphorus atom forms a bond with Ru, wherein R is independently —H, —$C_1$-$C_{18}$ alkyl, or aryl; or
(g) an —SR group whose sulfur atom forms a bond with Ru, wherein R is independently —H, —$C_1$-$C_{18}$ alkyl, or aryl.

47. The compound of claim 45, wherein $L^2$ is P(phenyl)$_3$ and each phenyl is independently substituted at the 3 or 4 position.

48. The compound of claim 45, wherein $L^2$ is P(phenyl)$_3$ and at least one phenyl is substituted with —($C_1$-$C_{18}$ alkyl)-OH.

49. The compound of claim 45, wherein $L^2$ is P(phenyl)$_3$ and each phenyl is substituted with —($C_1$-$C_{18}$ alkyl)-OH.

50. The compound of claim 45, wherein $L^2$ is P(phenyl)$_3$ and at least one phenyl is substituted with —COOH.

51. The compound of claim 45, wherein $L^2$ is P(phenyl)$_3$ and each phenyl is substituted with —COOH.

52. The compound of claim 45, wherein $L^2$ is P(phenyl)$_3$ and at least one phenyl is substituted with —OH.

53. The compound of claim 45, wherein $L^2$ is P(phenyl)$_3$ and each phenyl is substituted with —OH.

54. The compound of claim 45, wherein $L^2$ is P(phenyl)$_3$ and at least one phenyl is substituted with —$NH_2$.

55. The compound of claim 45, wherein $L^2$ is P(phenyl)$_3$ and each phenyl is substituted with —$NH_2$.

56. A compound of Formula VII:

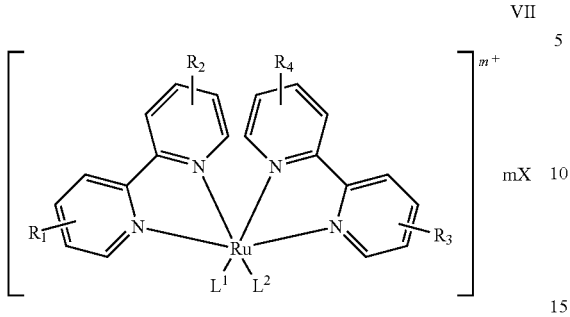

wherein:
each $L^1$ is independently an organic molecule having:
(a) a 5-membered monocyclic aromatic ring, one of the ring's members being a nitrogen atom that forms a bond with Ru;
(b) a 6-membered monocyclic aromatic ring, one of the ring's members being a nitrogen atom that forms a bond with Ru;
(c) an 8-10-membered bicyclic ring, one of the bicyclic rings being aromatic and having a nitrogen atom member that forms a bond with Ru;
(d) an —$NH_2$ group whose nitrogen atom forms a bond with Ru;
(e) a —COOH group, one of whose oxygen atoms forms a bond with Ru;
(f) a —$PR_2$ group whose phosphorus atom forms a bond with Ru, wherein R is independently —H, —$C_1$-$C_{18}$ alkyl, or aryl;
(g) an —SR group whose sulfur atom forms a bond with Ru, wherein R is independently —H, —$C_1$-$C_{18}$ alkyl, or aryl; or
(h) a —CN group whose nitrogen atom forms a bond with Ru;
$L^2$ is $(R^9)_3P$, $(R^9O)_3P$, m is 2, and $L^2$ is not $P(phenyl)_3$; or $L^2$ is a labeling molecule or an active derivative thereof connected to Ru through the phosphorus atom of $(R^9)_2P$ or $(R^9O)_2P$ and m is 2; or $L^2$ is a labeling molecule or an active derivative thereof connected to Ru through the nitrogen atom of: $NHR^9$, $N(R^9)_2$, pyridyl, $C(R^9)$=NH, $C(R^9)$=$NR^9$, cyclic aliphatic amine group or nitrile and m is 2;
wherein each $R^9$ is independently —$C_1$-$C_{18}$ alkyl, —$C_3$-$C_8$ cycloalkyl, or phenyl;
$R^1$ to $R^4$ are independently —H, —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, —OH, or —SH, or $R^1$ and $R^2$ and/or $R^3$ and $R^4$ can combine to form a carbocyclic ring substituted by one or more oxo groups, wherein at least one of $R^1$ to $R^4$ is not H;
X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and
Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

57. The compound of claim 56, wherein each $L^1$ is independently an organic molecule having:
(a) a 5-membered monocyclic aromatic ring, one of the ring's members being a nitrogen atom that forms a bond with Ru;
(b) a 6-membered monocyclic aromatic ring, one of the ring's members being a nitrogen atom that forms a bond with Ru;
(c) an 8-10-membered bicyclic ring, one of the bicyclic rings being aromatic and having a nitrogen atom member that forms a bond with Ru;
(d) an —$NH_2$ group whose nitrogen atom forms a bond with Ru;
(e) a —COOH group, one of whose oxygen atoms forms a bond with Ru;
(f) a —$PR_2$ group whose phosphorus atom forms a bond with Ru, wherein R is independently —H, —$C_1$-$C_{18}$ alkyl, or aryl; or
(g) an —SR group whose sulfur atom forms a bond with Ru, wherein R is independently —H, —$C_1$-$C_{18}$ alkyl, or aryl.

58. The compound of claim 56, wherein $L^2$ is P(methyl)(phenyl)$_2$.

59. The compound of claim 56, wherein $L^2$ is P(methyl)$_2$(phenyl).

60. A compound of Formula VIII:

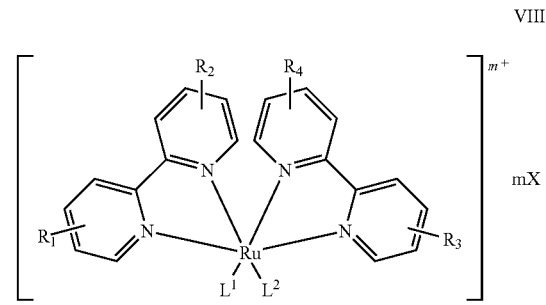

wherein:
each $L^1$ is independently a labeling molecule or an active derivative thereof connected to Ru through the phosphorous atom of $(R^9)_2P$ or $(R^9O)_2P$ and m is 2; or $L^1$ is a labeling molecule or an active derivative thereof connected to Ru through the nitrogen atom of: $NHR^9$, $N(R^9)_2$, pyridyl, $C(R^9)$=NH, $C(R^9)$=$NR^9$, cyclic aliphatic amine group or nitrile and m is 2;
wherein each $R^9$ is independently —$C_1$-$C_{18}$ alkyl, —$C_3$-$C_8$ cycloalkyl, or phenyl;
$L^2$ is Cl—, phosphine, $OH_2$, or pyridine and m is 2; or $L^2$ is —CN and m is 1;
$R^1$ to $R^4$ are independently —H, —$C_1$-$C_{18}$ alkyl; —$NH_2$, —($C_1$-$C_{18}$ alkyl)-O—($C_1$-$C_{18}$ alkyl), —OC(O)($C_1$-$C_{18}$ alkyl), —($C_1$-$C_{18}$ alkyl)-OH, aryl, —($C_1$-$C_{18}$ alkyl)-oxy, —($C_1$-$C_{18}$ alkyl)-amino, —($C_1$-$C_{18}$ alkyl)-thio, —$CO_2Y$, —C(=O)Y, —C(=O)$NY_2$, —$NO_2$, or —SH, or $R^1$ and $R^2$ and/or $R^3$ and $R^4$ can combine to form a carbocyclic ring substituted by one or more oxo groups;
X is $Cl^-$, $F^-$, $Br^-$, $I^-$, $PF_6^-$, $CF_3SO_3^-$, ($C_1$-$C_{18}$ alkyl)-$CO_2^-$, or ($C_1$-$C_{18}$ alkyl)-$SO_3^-$; and
Y is selected from the group consisting of —H, —$C_1$-$C_{18}$ alkyl, aryl, —($C_1$-$C_{18}$ alkyl)-aryl, —$C_3$-$C_8$ cycloalkyl, heteroaryl, and heterocyclyl.

61. The compound of claim 60, wherein the labeling molecule or an active derivative thereof contains a —CN group whose nitrogen atom forms a bond with Ru.

62. The compound of claim 60, wherein the labeling molecule or an active derivative thereof contains rhodamine.

63. The compound of claim 60, wherein the labeling molecule or an active derivative thereof contains fluorescein.

64. The compound of claim 60, wherein the labeling molecule or an active derivative thereof contains iodeosin.

65. A method for releasing a fluorescent molecule from a Photolabile Compound, comprising:
exposing a compound of claim 60 to light under conditions sufficient to release the fluorescent molecule.

66. The method of claim 65, wherein the light comprises a wavelength of about 300 to about 500 nm.

67. The method of claim 65, wherein the light comprises a wavelength of about 300 to about 360 nm.

68. The method of claim 65, wherein the light comprises a wavelength of about 450 to about 500 nm.

69. The method of claim 65, wherein the light comprises visible light or infrared light.

70. The method of claim 65, wherein the exposing occurs at a temperature from about 0° C. to about 150° C.

71. The method of any one of claims 1, 45, 56 or 60 wherein $L^2$ is a labeling molecule or a derivative thereof.

72. The method of claim 71, wherein $L^2$ is Rhodamine B-Methylaminopropionitrileamide (RhodB-MAPN), Rhodamine 6G-Methyl aminopropionitrileamide (Rhod6G-MAPN), RhodB-MAMePy, Rhod6G-MAMePy or a salt thereof.

73. A compound selected from the group consisting of: [Ru(bpy)$_2$(RhodB-MAPN)Cl]Cl, [Ru(bpy)$_2$(Rhod6G-MAPN)Cl]Cl, [Ru(bpy)$_2$(RhodB-MAMePy)Cl]Cl.

74. A compound selected from the group consisting of: [Ru(bpy)$_2$(RhodB-MAPN)Cl]Z, [Ru(bpy)$_2$(Rhod6G-MAPN)Cl]Z, [Ru(bpy)$_2$(RhodB-MAMePy)Cl]Z, wherein Z is an anion.

75. The compound of claim 45, wherein $L^2$ is P(phenyl)$_3$ and at least one phenyl is substituted with —NO$_2$.

76. The compound of claim 45, wherein $L^2$ is P(phenyl)$_3$ and each phenyl is substituted with —NO$_2$.

* * * * *

UNITED STATES PATENT AND TRADEMARK OFFICE
CERTIFICATE OF CORRECTION

PATENT NO.      : 9,744,236 B2
APPLICATION NO. : 13/336643
DATED           : August 29, 2017
INVENTOR(S)     : Rafael Yuste et al.

It is certified that error appears in the above-identified patent and that said Letters Patent is hereby corrected as shown below:

In the Specification

At Column 1, Line number 13, please delete "The work herein was supported in whole, or in part, by National Institute of Health Grant Nos. EYO11787 and EY013237. Thus, the United States Government has certain rights to the invention. This invention was made with government support under NYSTAR Contract No. C000082 awarded by NYSTAR. The government has certain rights in the invention." and insert --This invention was made with government support under grants EY013237 and EY011787 awarded by the NIH. The Government has certain rights in the invention.--

Signed and Sealed this
Seventh Day of November, 2017

Joseph Matal
*Performing the Functions and Duties of the
Under Secretary of Commerce for Intellectual Property and
Director of the United States Patent and Trademark Office*